United States Patent
Glossop et al.

(10) Patent No.: US 11,130,730 B2
(45) Date of Patent: Sep. 28, 2021

(54) COMPOUNDS AND THERAPEUTICS USES THEREOF

(71) Applicant: Centauri Therapeutics Limited (GB/GB), London (GB)

(72) Inventors: Melanie Glossop, Kent (GB); Christine Watson, Kent (GB)

(73) Assignee: CENTAURI THERAPEUTICS LIMITED (GB/GB), London (GB)

( * ) Notice: Subject to any disclaimer, the term of this patent is extended or adjusted under 35 U.S.C. 154(b) by 0 days.

(21) Appl. No.: 16/603,545

(22) PCT Filed: Apr. 6, 2018

(86) PCT No.: PCT/GB2018/050927
§ 371 (c)(1),
(2) Date: Oct. 7, 2019

(87) PCT Pub. No.: WO2018/185494
PCT Pub. Date: Oct. 11, 2018

(65) Prior Publication Data
US 2020/0231538 A1    Jul. 23, 2020

(30) Foreign Application Priority Data

Apr. 7, 2017 (GB) ..................................... 1705684

(51) Int. Cl.
C07C 235/20 (2006.01)
A61K 47/54 (2017.01)
C07H 21/02 (2006.01)
C07H 21/04 (2006.01)
A61P 35/00 (2006.01)
A61K 39/00 (2006.01)

(52) U.S. Cl.
CPC .... *C07C 235/20* (2013.01); *A61K 39/001169* (2018.08); *A61K 47/549* (2017.08); *A61P 35/00* (2018.01); *C07H 21/02* (2013.01); *C07H 21/04* (2013.01); *A61K 2039/627* (2013.01)

(58) Field of Classification Search
None
See application file for complete search history.

(56) References Cited

U.S. PATENT DOCUMENTS 8,263,082 B2 * 9/2012 Mullis ..................... A61P 37/04
424/178.1

OTHER PUBLICATIONS

G. E. Winter et al, Phthalimide conjugation as a strategy for in vivo target protein degradation, Science, vol. 348, No. 6241, Jun. 19, 2015, pp. 1376-1381.
Sascha A. Kristian et al, "Retargeting pre-existing human antibodies to a bacterial pathogen with an alpha-Gal conjugated aptamer", Journal of Molecular Medicine., vol. 93, No. 6, May 5, 2015, pp. 619-631.

* cited by examiner

*Primary Examiner* — Eric Olson
(74) *Attorney, Agent, or Firm* — Aura IP Law, PC

(57) ABSTRACT

The invention relates to novel compounds with the ability to link an immune response to a defined therapeutic target, to the use of said compounds in treating cancer and infectious diseases, to compositions containing said compounds, processes for their preparation and to novel intermediates used in said process.

20 Claims, 13 Drawing Sheets
Specification includes a Sequence Listing.

A

B

C

D

FIGURE 1 (ctd)

A

B

C

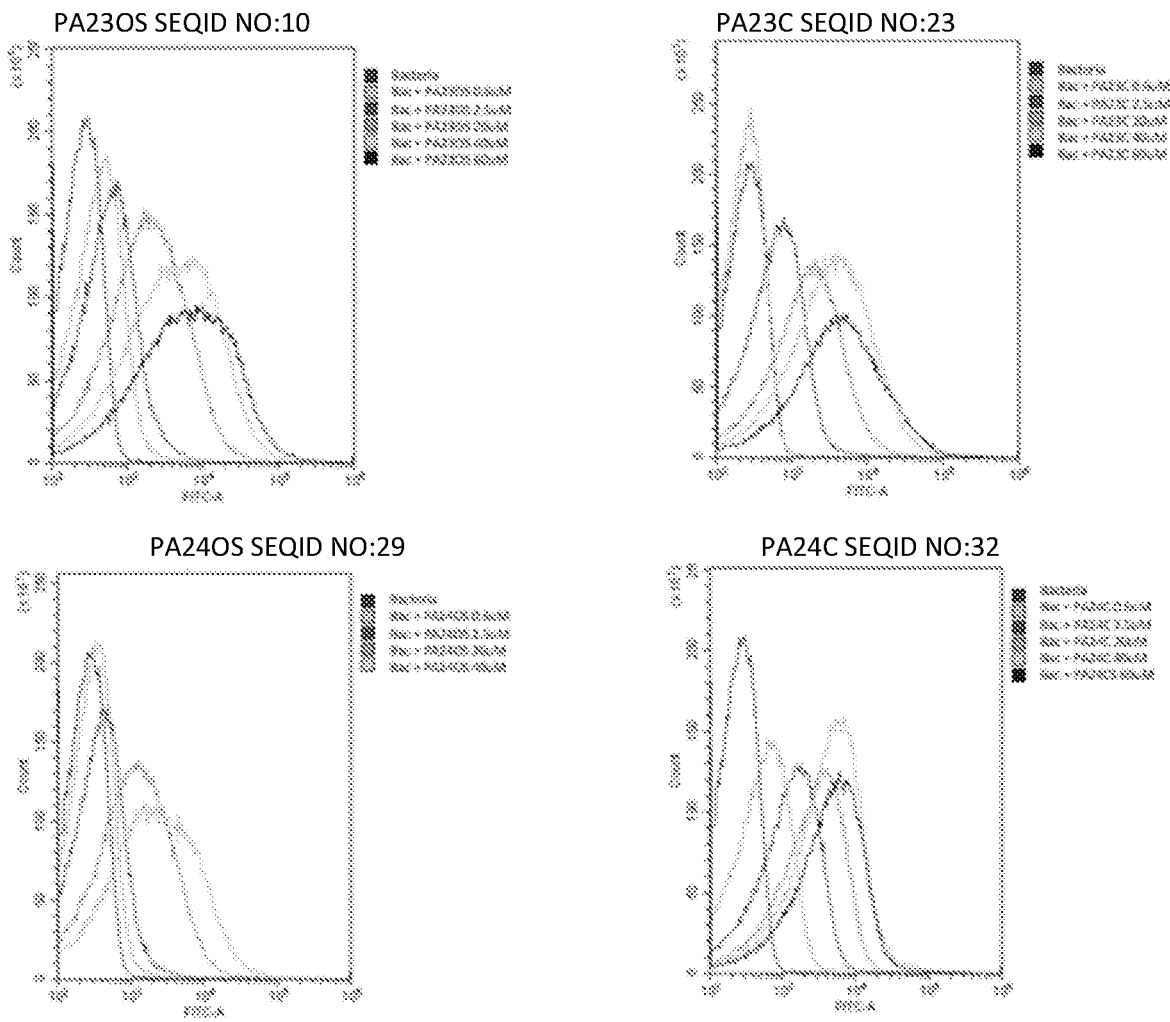
FIGURE 7 (ctd)

COMPOUNDS AND THERAPEUTICS USES THEREOF

CROSS-REFERENCE TO RELATED APPLICATIONS

The present application is a U.S. National Stage entry under 35 U.S.C. § 371 of International Application No. PCT/GB2018/050927 filed on Apr. 6, 2018, designating the United States of America and published in English on Nov. 10, 2018, which is hereby incorporated by reference in its entirety.

FIELD OF THE INVENTION

The invention relates to novel compounds with the ability to link an immune response to a defined therapeutic target, to the use of said compounds in treating cancer and infectious diseases, to compositions containing said compounds, processes for their preparation and to novel intermediates used in said process.

REFERENCE TO A SEQUENCE LISTING SUBMITTED ON COMPUTER

The content of ASCII text file of the sequence listing named "2019-10-03-Sequence Listing-SGTRS-016US0.txt" which was filed in PCT/GB2018/050927 on Apr. 6, 2018, downloaded from the WIPO database, is 20 kb in size with a created date of Oct. 3, 2019, and electronically submitted via EFS-Web herewith the application, is incorporated herein by reference in its entirety.

BACKGROUND OF THE INVENTION

There is a need to find novel ways to recruit an individual's immune system to fight disease. The human immune system continually surveys the body seeking foreign signals to identify potentially harmful pathogens or mutated human cells (that could become a cause of cancerous growth) and targets them for elimination. Natural antibodies exist that can be recruited to said pathogens or mutated human cells to drive the immune system to eliminate the threat.

Cancer is a group of diseases involving abnormal cell growth with the potential to invade or spread to other parts of the body. In 2012, cancer occurred in about 14.1 million people. It caused about 8.2 million deaths or 14.6% of all human deaths. The most common types of cancer in males are lung cancer, prostate cancer, colorectal cancer and stomach cancer. In females the most common types are breast cancer, colorectal cancer, lung cancer, and cervical cancer. It is well established that the immune response plays a vital role in the identification and elimination of cancerous cells. Drugs exist that fight cancer by boosting an individual's immune system to help fight the cancer. There is a need to be able to better target the immune response specifically to the cancer cell and to generate a broader range of the patient's own tumour associated antigens. Targeting pre-existing natural antibodies to the patient's own tumour could meet this need. There is an urgent need to identify novel ways of treating bacterial, viral and fungal infections. Antimicrobial drug resistance is becoming a major global health threat. For example, it is estimated that more than 2 million people in the US are infected with bacteria resistant to one class of antibiotics every year (Centers for Disease Control and Prevention, 2013).

An innovative approach to the treatment of infectious disease or cancer was disclosed in WO 2005/079423 which describes an immunity linker which contains two binding moieties. The first binding moiety is capable of binding to an immune response component of an individual. The second binding moiety is capable of binding to any compound or foreign material such as antigens, pathogens, chemicals, or endogenous materials such as altered cells found in cancer. The resultant effect of said immunity linker molecule is that the pre-existing immune response of the individual is diverted towards the target, i.e. the cancer cell. Examples of said first binding moieties include compounds or agents which are recognised by the immune system of said individual as foreign and which would therefore trigger an immune response. One example of a first binding moiety is a carbohydrate molecule capable of binding to a human serum antibody anti-alpha-galactosyl (i.e. galactosyl-alpha-1,3-galactosyl-beta-1,4-N-acetylglucosamine). Examples of said second binding moieties include nucleic acid aptamer molecules that bind to a specific target molecule. The principle of the method disclosed in WO 2005/079423 is that the second binding moiety (e.g. nucleic acid aptamer) of the linker molecule will bind to a cancer cell and the presence of the first binding moiety (i.e. the carbohydrate molecule capable of binding to a human anti-alpha-galactosyl antibody) on the linker molecule will divert an immune response to the cancer cell resulting in effective destruction of the cancer cell. A similar approach may be used in the treatment of diseases or disorders mediated and/or caused by an infective agent wherein the second binding moiety (i.e. nucleic acid aptamer) of the linker molecule will bind to the infective agent.

The epidermal growth factor receptor (EGFR), also known as ErbB-1 or HER1 in humans, is the cell-surface receptor for members of the epidermal growth factor family (EGF-family) of extracellular protein ligands. EGFR is a member of the ErbB family of receptors, a subfamily of four closely related receptor tyrosine kinases: EGFR (ErbB-1), HER2/c-neu (ErbB-2), Her 3 (ErbB-3) and Her 4 (ErbB-4).

Mutations affecting EGFR expression or activity could result in cancer. In particular, mutations that lead to EGFR overexpression (known as upregulation) or overactivity have been associated with a number of cancers, including lung cancer, anal cancers (such as colorectal cancer) and glioblastoma multiforme. These somatic mutations involving EGFR lead to its constant activation, which produces uncontrolled cell division. In glioblastoma a more or less specific mutation of EGFR, called EGFRvIII is often observed. Mutations, amplifications or misregulations of EGFR or family members are implicated in about 30% of all epithelial cancers.

Prostate-specific membrane antigen (PSMA) (also known as Glutamate carboxypeptidase II (GCPII), N-acetyl-L-aspartyl-L-glutamate peptidase I (NAALADase I) and NAAG peptidase) is an enzyme that in humans is encoded by the FOLH1 (folate hydrolase 1) gene. Human GCPII contains 750 amino acids and weighs approximately 84 kDa.

Human PSMA is highly expressed in the prostate, roughly a hundred times greater than in most other tissues. In some prostate cancers, PSMA is the second-most upregulated gene product, with an 8- to 12-fold increase over levels in noncancerous prostate cells. Because of this high expression, PSMA is being developed as a potential biomarker for therapy and imaging of some cancers. In human prostate cancer, the higher expressing tumors are associated with quicker time to progression and a greater percentage of patients suffering relapse.

*Pseudomonas aeruginosa* (*P. aeruginosa*) is a gram-negative pathogen which is characterised by an innate resistance to clinically used antibiotics and is associated with severe infections, particularly in compromised patients in the hospital environment. The Infectious Disease Society of America has included *P. aeruginosa* in its list of 'ESKAPE' pathogens. These 'ESKAPE' bacteria pose the greatest threat to public health threat due to their increasing prevalence and the ineffectiveness of existing antibacterial agents (Clin. Infect Dis. 2009, 1).

There is therefore a great need for linker molecules which contain spacer groups which have been optimised to control the number and position of first binding moieties (i.e. the carbohydrate molecule capable of binding to a human anti-alpha-galactosyl antibody) relative to the position of the second binding moiety (i.e. the nucleic acid aptamer). Such linker molecules are designed to attract natural antibodies in such a way as to be able to maximise the efficacy of immune recruitment while minimising potential side effects and therefore have great utility in the provision of effective anti-cancer therapies and therapies against infective agents.

SUMMARY OF THE INVENTION

According to a first aspect of the invention, there is provided a compound of formula (I) or a pharmaceutically acceptable salt thereof:

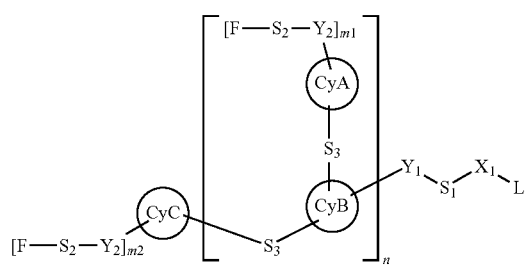

(I)

wherein:
L represents a binding moiety selected from a nucleic acid aptamer;
$S_1$ represents a spacer selected from a —$(CH_2)_a$— or —$(CH_2)_b$—$(CH_2$—$CH_2$—$O)_c$—$(CH_2)_d$— group, wherein one to five of said —$CH_2$— groups may optionally be substituted by one or more groups selected from —O—, —C(O)NH— and —NHC(O)— and phenyl;
a represents an integer selected from 1 to 35;
b represents an integer selected from 0 to 5;
c represents an integer selected from 1 to 20;
d represents an integer selected from 1 to 20;
$S_2$ represents a spacer selected from a —$(CH_2)_e$— or —$(CH_2)_f$—$(CH_2$—$CH_2$—$O)_g$—$(CH_2)_h$— group, wherein one to three of said —$CH_2$— groups may optionally be substituted by one or more groups selected from —N(H)—, —C(O)NH— and —NHC(O)—;
e represents an integer selected from 1 to 15;
f represents an integer selected from 1 to 10;
g represents an integer selected from 1 to 20;
h represents an integer selected from 1 to 5;
$S_3$ represents a spacer selected from a —$(CH_2)_q$— or —$(CH_2)_r$—$(CH_2$—$CH_2$—$O)_s$—$(CH_2)_t$— group, wherein one to ten of said —$CH_2$— groups may optionally be substituted by one or more groups selected from —N(H)—, —C(O)NH—, —NHC(O)— and —O—;

q represents an integer selected from 1 to 25;
r represents an integer selected from 1 to 10;
s represents an integer selected from 1 to 20;
t represents an integer selected from 1 to 10;
$X_1$ represents —O—;
$Y_1$ and $Y_2$ independently represent a bond, —O—, —S—, —NH—, —NHC(O)—, —C(O)NH—, —OC(O)—, —C(O)O—, —SC(O)—, —C(O)S—, —NHSO$_2$—, —SO$_2$NH— or —NHC(O)NH— group;
F represents a carbohydrate molecule capable of binding to a human anti-alpha-galactosyl antibody;
m1 and m2 independently represent an integer selected from 1 to 5;
n represents an integer selected from 1 or 2; and
CyA, CyB and CyC independently represent biphenyl or triphenyl.

BRIEF DESCRIPTION OF THE FIGURES

FIG. 2 demonstrates a difference in recruitment of anti-galactosyl antibodies to the human cancer cell line A431 by Examples 2-4.

FIG. 11 demonstrates a dose related increase in recruitment of anti-galactosyl IgG antibodies to the human cancer cell line A431 by Example 1.

FIG. 12 demonstrates a dose related increase in recruitment of anti-galactosyl IgM antibodies to the human cancer cell line A431 by Example 1.

FIG. 13 demonstrates a dose dependent increase in C3b deposition in the presence of normal human serum and Example 1. The shift in fluorescence intensity (PE) occurs due to the recruitment of C3b from serum to the A431 cells' surface.

DETAILED DESCRIPTION OF THE INVENTION

Figure 1:
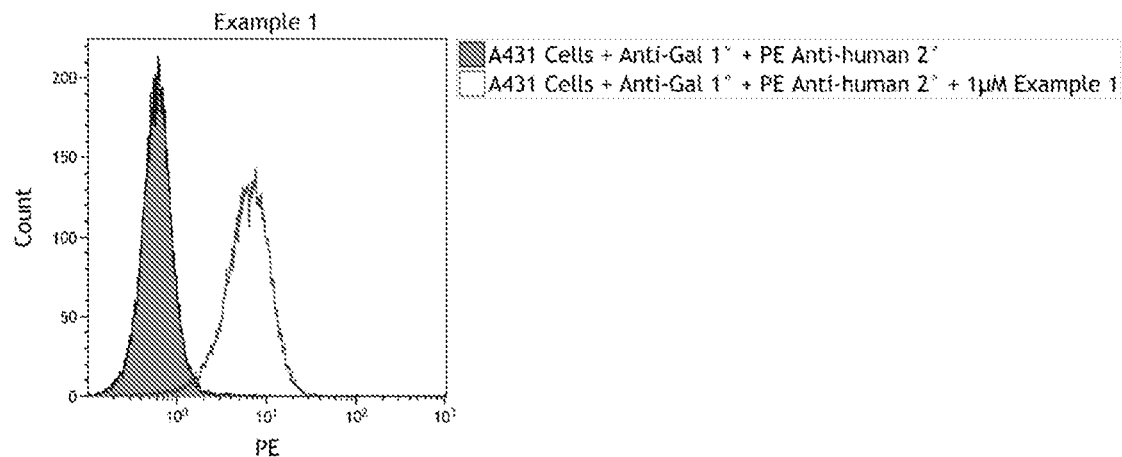
FIG. 1: demonstrates the capture of anti-alpha galactosyl IgG antibodies to the cell surface using Example 1 (FIG. 1A), Example 2 (FIG. 1B), Example 3 (FIG. 1C) and Example 4 (FIG. 1D).
Figure 1:
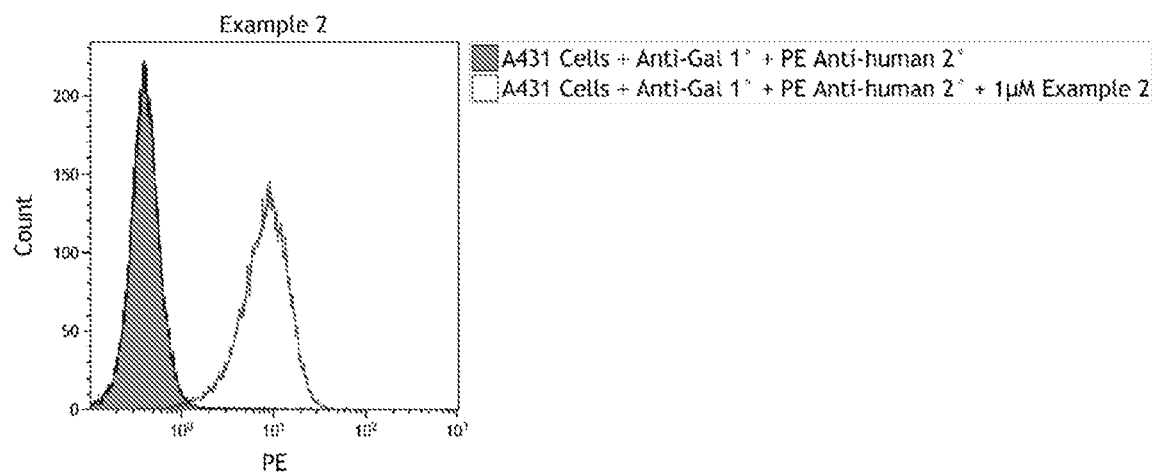
Figure 1:
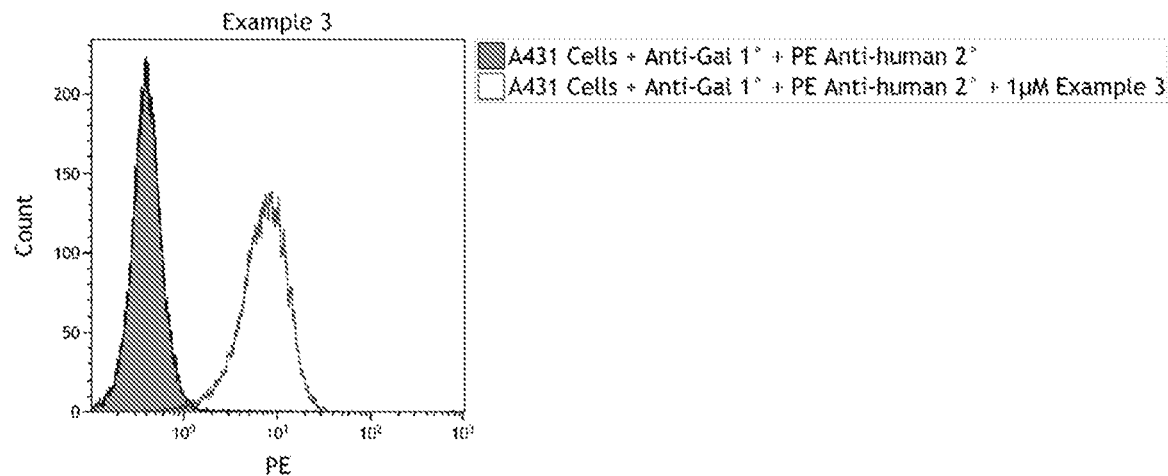

The compounds of the present invention comprise linker molecules which have been optimised to control and display the number and position of F groups (i.e. the carbohydrate molecule capable of binding to a human anti-alpha-galactosyl antibody) relative to the position of the binding moiety L (i.e. the nucleic acid aptamer). For example, a rigid cyclic group has the advantage of providing a scaffold for the optimal positioning of one or more F groups relative to L. It will be appreciated that the exact number and orientation of F groups relative to L will vary depending on the nature of the L group. Furthermore, the presence of the cyclic group, which contains a single phenyl ring, a biphenyl ring or a triphenyl ring provides the significant advantage of presenting multiple F groups (i.e. the carbohydrate molecule capable of binding to a human anti-alpha-galactosyl antibody) to enhance the resultant immune response from the host. Chemical presentation of multiple binding groups was previously known in the art, however, this has been achieved using one or more amino acid groups (for example see WO 2014/178878) or branching linker groups (for example see US 2014/0112975) by contrast to the present invention which uses either a single 6 membered ring system (i.e. phenyl), two 6 membered ring systems joined by a bond (biphenyl) or three membered ring systems joined by 2 bonds (triphenyl). The technical effect of this distinction is that the compounds of the present invention may be prepared more easily than the linkers previously known in art, advantageously avoid the presence of chiral centres and are less liable to protease degradation. Synthesis of the compounds of the present invention also do not make use of resins and therefore provide the advantage of being suitable for scaling for large scale pharmaceutical manufacture. Therefore, the compounds of the invention are not only therapeutically effective but provide the advantage of enhancing the immune response from the host and ease and efficiency of synthesis in high yields with scalability. In addition, the linkers of the present invention are not labile, therefore, do not typically comprise "cleavable linker" components as required by many compounds previously known in the art (see U.S. Pat. No. 8,828,956 for example). Furthermore, the linkers of the present invention allow the person skilled in the art to choose specific left and right hand combinations of groups with synthetic ease and efficiency to enable the optimal number of F groups per aptamer.

In one embodiment, $S_1$ represents a spacer selected from:
—$(CH_2)_a$—, wherein one to four of said —$CH_2$— groups are optionally substituted by one or more groups selected from —C(O)NH— and —NHC(O)— (such as —$(CH_2)_2$—, —$CH_2$—CONH—$(CH_2)_2$—, —$CH_2$—NHCO—$(CH_2)_4$—CONH—$(CH_2)_2$—, —$(CH_2)_6$—, —$(CH_2)_5$—CONH—$(CH_2)_5$—CONH—$(CH_2)_6$— or —$(CH_2)_5$—CONH—$(CH_2)_5$—CONH—$(CH_2)_5$—CONH—$(CH_2)_5$—CONH— $(CH_2)_6$—); or
—$(CH_2)_b$—$(CH_2$—$CH_2$—O$)_c$—$(CH_2)_d$—, wherein one to five of said —$CH_2$— groups are optionally substituted by one or more groups selected from —O—, —C(O)NH—, —NHC(O)— and phenyl (such as —$(CH_2)_2$—NHCO—$(CH_2CH_2O)_{12}$—$(CH_2)_2$—, —$(CH_2)_2$—NHCO—$(CH_2CH_2O)_4$—$(CH_2)_2$—NHCO—$CH_2$—O-phenyl-CONH—$(CH_2)_6$—, —$(CH_2)_2$—NHCO—$(CH_2CH_2O)_{12}$—$(CH_2)_2$—NHCO—$CH_2$—O-phenyl-CONH—$(CH_2)_6$— or —$(CH_2CH_2O)_4$—$(CH_2)_2$—CONH—$(CH_2)_2$—).

In a further embodiment, S represents a spacer selected from —$(CH_2)_a$—, wherein one or two of said —$CH_2$— groups are optionally substituted by a —C(O)NH— or —NHC(O)— group (such as —$(CH_2)_2$—, —$CH_2$—CONH—$(CH_2)_2$—, —$CH_2$—NHCO—$(CH_2)_4$—CONH—$(CH_2)_2$— or —$(CH_2)_6$—) or —$(CH_2)_b$—$(CH_2$—$CH_2$—O$)_c$—$(CH_2)_d$—, wherein one or two of said —$CH_2$— groups are optionally substituted by a —C(O)NH— or —NHC(O)— group (such as —$(CH_2)_2$—NHCO—$(CH_2CH_2O)_{12}$—$(CH_2)_2$—).

In a yet further embodiment, S represents a spacer selected from:
—$(CH_2)_a$—, wherein two or four of said —$CH_2$— groups are optionally substituted by —C(O)NH— (such as —$(CH_2)_6$—, —$(CH_2)_5$—CONH—$(CH_2)_5$—CONH—$(CH_2)_6$— or —$(CH_2)_5$—CONH—$(CH_2)_5$—CONH—$(CH_2)_5$—CONH—$(CH_2)_5$—CONH—$(CH_2)_6$—); or
—$(CH_2)_b$—$(CH_2$—$CH_2$—O$)_c$—$(CH_2)_d$—, wherein five of said —$CH_2$— groups are optionally substituted by one or more groups selected from —O—, —C(O)NH—, —NHC(O)— and phenyl (such as —$(CH_2)_2$—NHCO—$(CH_2CH_2O)_4$—$(CH_2)_2$—NHCO—$CH_2$—O-phenyl-CONH—$(CH_2)_6$— or —$(CH_2)_2$—NHCO—$(CH_2CH_2O)_{12}$—$(CH_2)_2$—NHCO—$CH_2$—O-phenyl-CONH—$(CH_2)_6$—).

In a still yet further embodiment, S represents a spacer selected from:
—$(CH_2)_a$— (such as —$(CH_2)_6$—).

It will be appreciated that a, b, c, d, e, f, g, h, q, r, s and t are selected to maintain a suitable linker length between groups F and L. Examples of suitable linker lengths between F and L range from about 5 Å to about 50 Å or more in length, about 6 Å to about 45 Å, about 7 Å to about 40 Å, about 8 Å to about 35 Å, about 9 Å to about 30 Å, about 10 Å to about 25 Å, about 11 Å to about 20 Å, about 12 Å to about 15 Å. Thus, in one embodiment, a, b, c, d, e, f, g, h, q, r, s and t represent a total integer of no more than 45, such as between 5 and 45, such as between 7 and 42, such as no more than 30, such as between 5 and 30, such as between 7 and 29.

In one embodiment, a represents an integer selected from 1 to 30. In a further embodiment, a represents an integer selected from 2 to 30. In a further embodiment, a represents an integer selected from 2, 4, 6, 9, 18 or 30. In a further embodiment, a represents an integer selected from 6 to 30. In a further embodiment, a represents an integer selected from 6, 18 or 30. In a further embodiment, a represents an integer selected from 1 to 10. In a further embodiment, a represents an integer selected from 2 to 9. In a yet further embodiment, a represents an integer selected from 2, 4, 6 or 9. In a still yet further embodiment, a represents an integer selected from 6.

In one embodiment, b represents an integer selected from 0 to 3. In a further embodiment, b represents an integer selected from 0 or 3. In a further embodiment, b represents an integer selected from 1 to 3. In a further embodiment, b represents an integer selected from 2 or 3. In a yet further embodiment, b represents an integer selected from 3.

In one embodiment, c represents an integer selected from 1 to 15. In a further embodiment, c represents an integer selected from 1 to 12. In a further embodiment, c represents an integer selected from 4 to 12. In a yet further embodiment, c represents an integer selected from 4 or 12. In a yet further embodiment, c represents an integer selected from 4.

In one embodiment, d represents an integer selected from 1 to 15. In a further embodiment, d represents an integer selected from 2 to 13. In a further embodiment, d represents an integer selected from 2, 5 or 13. In a further embodiment, d represents an integer selected from 13.

In one embodiment, $Y_1$ represents a bond, —C(O)NH— or —O—. In a further embodiment, $Y_1$ represents —C(O)NH—.

In one embodiment, $S_2$ represents a spacer selected from:
—$(CH_2)_e$—, wherein one or two of said —$CH_2$— groups are optionally substituted by one or two groups selected from —N(H)—, —C(O)NH— and —NHC(O)— (such as —$(CH_2)_3$—NHCO—$CH_2$—, —$(CH_2)_3$—, —$(CH_2)_3$—NHCO—$(CH_2)_4$—CONH—$CH_2$—, —$(CH_2)_3$—NH—$CH_2$— or —$(CH_2)_3$—NHCO—$(CH_2)_3$—NHCO—$CH_2$—); or
—$(CH_2)_f$—$(CH_2$—$CH_2$—$O)_g$—$(CH_2)_h$—, wherein one to three of said —$CH_2$— groups are optionally substituted by one to three —NHC(O)— groups (such as —$(CH_2)_3$—NHCO—$(CH_2CH_2O)_4$—$(CH_2)_2$—NHCO—$CH_2$—, —$(CH_2)_3$—NHCO—$(CH_2CH_2O)_{12}$—$(CH_2)_2$—NHCO—$CH_2$— or —$(CH_2)_3$—NHCO—$(CH_2)_3$—NHCO—$(CH_2CH_2O)_4$—$(CH_2)_2$—NHCO—$CH_2$—).

In a further embodiment, $S_2$ represents a spacer selected from —$(CH_2)_e$—, wherein one or two of said —$CH_2$— groups are optionally substituted by a —C(O)NH— or —NHC(O)— group (such as —$(CH_2)_3$—NHCO—$CH_2$—, —$(CH_2)_3$—NHCO—, —$(CH_2)_3$—, —$(CH_2)_3$—NHCO—$(CH_2)_4$—CONH—$CH_2$— or —$(CH_2)_3$—NH—$CH_2$—) or —$(CH_2)_f$—$(CH_2$—$CH_2$—$O)_g$—$(CH_2)_h$—, wherein one or two of said —$CH_2$— groups are optionally substituted by a —C(O)NH— or —NHC(O)— group (such as —$(CH_2)_3$—NHCO—$(CH_2)_2$—$(OCH_2CH_2)_4$—NHCO—$CH_2$— or —$(CH_2)_4$—NHCO—$(CH_2)_2$—$(OCH_2CH_2)_4$—NHCO—$CH_2$—).

In a yet further embodiment, $S_2$ represents a spacer selected from:
—$(CH_2)_e$—, wherein one or two of said —$CH_2$— groups are optionally substituted by one or two —NHC(O)— groups (such as —$(CH_2)_3$—NHCO—$CH_2$— or —$(CH_2)_3$—NHCO—$(CH_2)_3$—NHCO—$CH_2$—); or
—$(CH_2)_f$—$(CH_2$—$CH_2$—$O)_g$—$(CH_2)_h$—, wherein one to three of said —$CH_2$— groups are optionally substituted by one to three —NHC(O)— groups (such as —$(CH_2)_3$—NHCO—$(CH_2CH_2O)_4$—$(CH_2)_2$—NHCO—$CH_2$—, —$(CH_2)_3$—NHCO—$(CH_2CH_2O)_{12}$—$(CH_2)_2$—NHCO—$CH_2$— or —$(CH_2)_3$—NHCO—$(CH_2)_3$—NHCO—$(CH_2CH_2O)_4$—$(CH_2)_2$—NHCO—$CH_2$—).

In a still yet further embodiment, $S_2$ represents a spacer selected from:
—$(CH_2)_e$—, wherein one or two of said —$CH_2$— groups are optionally substituted by one or two groups selected from —N(H)—, —C(O)NH— and —NHC(O)— (such as —$(CH_2)_3$—NHCO—$CH_2$—); or
—$(CH_2)_f$—$(CH_2$—$CH_2$—$O)_g$—$(CH_2)_h$—, wherein one to three of said —$CH_2$— groups are optionally substituted by one to three —NHC(O)— groups (such as —$(CH_2)_3$—NHCO—$(CH_2CH_2O)_4$—$(CH_2)_2$—NHCO—$CH_2$—.

In one embodiment, e represents an integer selected from 1 to 10. In a further embodiment, e represents an integer selected from 3 to 10. In a further embodiment, e represents an integer selected from 3, 5, 9 or 10. In a further embodiment, e represents an integer selected from 5 to 9. In a further embodiment, e represents an integer selected from 5 or 9. In a further embodiment, e represents an integer selected from 4 to 10. In a yet further embodiment, e represents an integer selected from 4, 5 or 10. In a still yet further embodiment, e represents an integer selected from 5.

In one embodiment, f represents an integer selected from 1 to 8. In a further embodiment, f represents an integer selected from 2 to 8. In a further embodiment, f represents an integer selected from 2 to 6. In a yet further embodiment, f represents an integer selected from 4 to 8. In a yet further embodiment, f represents an integer selected from 4 or 8. In a still yet further embodiment, f represents an integer selected from 4.

In one embodiment, g represents an integer selected from 1 to 15. In a further embodiment, g represents an integer selected from 4 to 12. In a further embodiment, g represents an integer selected from 4 or 12. In a further embodiment, g represents an integer selected from 1 to 5. In a further embodiment, g represents an integer selected from 1 to 4. In a yet further embodiment, g represents an integer selected from 4.

In one embodiment, h represents an integer selected from 1 to 4. In a further embodiment, h represents an integer selected from 4.

In one embodiment, $Y_2$ represents a bond, —O— or —NHC(O)—. In a further embodiment, $Y_2$ represents a bond or —O—. In a yet further embodiment, $Y_2$ represents —O—.

In one embodiment, $S_3$ represents a spacer selected from:
—$(CH_2)_q$—, wherein one to five of said —$CH_2$— groups are optionally substituted by one to five groups selected from —C(O)NH—, —NHC(O)— and —O— (such as —CONH—$(CH_2)_2$—NHCO—$CH_2$—O— or —CONH—$(CH_2)_5$—CONH—$(CH_2)_5$—CONH—$(CH_2)_2$—NHCO—$CH_2$—O—); or
—$(CH_2)_r$—$(CH_2$—$CH_2$—$O)_s$—$(CH_2)_t$—, wherein one to four of said —$CH_2$— groups are optionally substituted by one to four groups selected from —C(O)NH—, —NHC(O)— and —O— (such as —CONH—$(CH_2)_2$—NHCO—$(CH_2CH_2)_4$—$(CH_2)_2$—NHCO—$CH_2$—O—).

In one embodiment, q represents an integer selected from 1 to 20. In a further embodiment, q represents an integer selected from 5 to 20. In a further embodiment, q represents an integer selected from 6 to 18. In a further embodiment, q represents an integer selected from 6 or 18. In a further embodiment, q represents an integer selected from 6. In a yet further embodiment, q represents an integer selected from 18.

In one embodiment, r represents an integer selected from 1 to 8. In a further embodiment, r represents an integer selected from 2 to 8. In a further embodiment, r represents an integer selected from 2 to 6. In a yet further embodiment, r represents an integer selected from 4 to 8. In a yet further embodiment, r represents an integer selected from 4 or 8. In a still yet further embodiment, r represents an integer selected from 4.

In one embodiment, s represents an integer selected from 1 to 15. In a further embodiment, s represents an integer selected from 4 to 12. In a further embodiment, s represents an integer selected from 4 or 12. In a further embodiment, s represents an integer selected from 1 to 5. In a further embodiment, s represents an integer selected from 1 to 4. In a yet further embodiment, s represents an integer selected from 4.

In one embodiment, t represents an integer selected from 1 to 5. In a further embodiment, t represents an integer selected from 5.

In one embodiment, m1 represents an integer selected from 1 to 4. In a further embodiment, m1 represents an integer selected from 3 or 4. In a further embodiment, m1 represents an integer selected from 1 to 3. In a yet further embodiment, m1 represents an integer selected from 2 or 3. In a yet further embodiment, m1 represents an integer selected from 1 or 2. In a yet further embodiment, m1 represents an integer selected from 1. In a yet further embodiment, m1 represents an integer selected from 2. In a yet further embodiment, m1 represents an integer selected from 3. In a yet further embodiment, m1 represents an integer selected from 4.

In one embodiment, m2 represents an integer selected from 1 to 4. In a further embodiment, m2 represents an integer selected from 1, 3 or 4. In a further embodiment, m2 represents an integer selected from 1 or 3. In a yet further embodiment, m2 represents an integer selected from 3 or 4. In a yet further embodiment, m2 represents an integer selected from 1. In a yet further embodiment, m2 represents an integer selected from 3. In a yet further embodiment, m2 represents an integer selected from 4.

In one embodiment, n represents an integer selected from 1.

In one embodiment, CyA, CyB and CyC each represent biphenyl; or CyA and CyC both represent triphenyl and CyB represents biphenyl; or CyA and CyB both represent biphenyl and CyC represents triphenyl; or CyA and CyB both represent triphenyl and CyC represents biphenyl.

According to a further aspect of the invention, there is provided a compound of formula (I)$^a$ or a pharmaceutically acceptable salt thereof:

$$\left[ \begin{array}{c} [F-S_2-Y_2]_{m1} \\ | \\ CyA \\ | \\ S_3 \\ | \\ CyC-S_3-CyB \\ | \\ [F-S_2-Y_2]_{m2} \end{array} \quad Y_1\diagdown S_1\diagdown X_1\diagdown L \right]_n \quad (I)^a$$

wherein:
L represents a binding moiety selected from a nucleic acid aptamer;
$S_1$ represents a spacer selected from a —$(CH_2)_a$— group;
a represents an integer selected from 6;
$S_2$ represents a spacer selected from a —$(CH_2)_e$— or —$(CH_2)_f$—$(CH_2$—$CH_2$—$O)_g$—$(CH_2)_h$— group, wherein one or two of said —$CH_2$— groups may optionally be substituted by one or two —NHC(O)— groups;
e represents an integer selected from 5;
f represents an integer selected from 4;
g represents an integer selected from 4;
h represents an integer selected from 4;
$S_3$ represents a spacer selected from a —$(CH_2)_q$— or —$(CH_2)_r$—$(CH_2$—$CH_2$—$O)_s$—$(CH_2)_t$— group, wherein one to five of said —$CH_2$— groups may optionally be substituted by one to five groups selected from —C(O)NH—, —NHC(O)— and —O—;
q represents an integer selected from 6 or 18;
r represents an integer selected from 4;
s represents an integer selected from 4;
t represents an integer selected from 5;
$X_1$ represents —O—;
$Y_1$ and $Y_2$ independently represent a —O— or —C(O)NH— group;
F represents a carbohydrate molecule capable of binding to a human anti-alpha-galactosyl antibody;
m1 and m2 independently represent an integer selected from 1 to 4;
n represents an integer selected from 1; and
CyA, CyB and CyC independently represent biphenyl or triphenyl.

References herein to the term "carbohydrate molecule capable of binding to a human anti-alpha-galactosyl antibody" include sugar (i.e. carbohydrate) moieties capable of binding to an immune response component (i.e. an anti-alpha-galactosyl antibody) of said human and consequently eliciting an immune response in a human. In one embodiment, said anti-alpha-galactosyl antibody is an anti-alpha-galactosyl IgG antibody or an anti-alpha-galactosyl IgM antibody. Examples of such carbohydrate molecules include alpha-galactosyl compounds and modified derivatives thereof. Further examples of suitable carbohydrate molecules include the alpha-gal epitopes listed in US 2012/0003251 as being suitable for use in the selective targeting and killing of tumour cells, the epitopes of which are herein incorporated by reference. In one embodiment, F is selected from galactosyl-alpha-1,3-galactosyl-beta-1,4-N-acetylglucosamine, alpha1-3 galactobiose, alpha1-3-beta1-4-galactotriose or galilipentasaccharide.

In one particular embodiment, F has a structure as shown in one of the following formulae:

wherein $S_2$ refers to the point of attachment to the $S_2$ group.

In one particular embodiment, F has a structure as shown in the following formula:

wherein $S_2$ refers to the point of attachment to the $S_2$ group.

References herein to "nucleic acid aptamer" refer to an oligonucleotide molecule that binds to a specific target molecule, such as a therapeutic target molecule. Nucleic acid aptamers are typically identified by selecting them from a large random sequence pool. In one embodiment, the nucleic acid aptamer is a DNA aptamer, an RNA aptamer or a nucleic acid analogue aptamer. In a further embodiment, the nucleic acid aptamer is an RNA aptamer. In one embodiment, the nucleic acid aptamer is an oligonucleotide comprising more than 5 but less than 100 nucleic acid molecules. It will be appreciated that the nucleic acid aptamer may contain natural and non-natural nucleotides, such as modified nucleotides which may have a fluorine or methoxy substituent at the 2' position. Examples of suitable non-natural nucleotides are described in Table 9.6.1 of Stovall et al (2014). *In Vitro Selection Using Modified or Unnatural Nucleotides*. doi:10.1002/0471142700.nc0906s56, the non-natural nucleotides of which are herein incorporated by reference.

L typically represents the following structure:

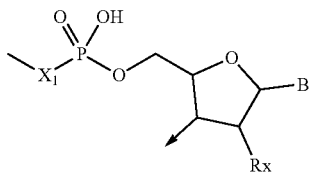

wherein B represents a natural base (i.e. adenine, thymine/uracil, guanine or cytosine) or non-natural base, the arrow represents the next nucleotide in the aptamer sequence, Rx represents hydrogen, a hydroxyl group or a 2' modification such as fluorine or methoxy and $X_1$ refers to the point of attachment to the $X_1$ group which is required by the invention to be —O—.

It will be apparent to the skilled person that a nucleic acid aptamer directed to a specific therapeutic target may easily be prepared in accordance with known procedures, such as Selective systematic Evolution of Ligands by EXponential enrichment (SELEX).

In one embodiment, the nucleic acid aptamer is an EGFR binding nucleic acid aptamer. EGFR is well known to be over-expressed in several human cancer types. In one embodiment, the EGFR binding nucleic acid aptamer is an aptamer which binds to any of the EGFR subfamily selected from: EGFR (ErbB-1), HER2/c-neu (ErbB-2), Her 3 (ErbB-3) and Her 4 (ErbB-4).

Examples of suitable EGFR binding nucleic acid aptamers include those described in Li et al (2011) PLoS One 6(6), 1-9 which describes a series of anti-EGFR aptamers, including E07. A dissertion was presented by Viswatej Avutu in 2011:
(https://repositories.lib.utexas.edu/bitstream/handle/2152/13407/Avutu-Bioch_10.pdf?sequence=2)
which describes a minimised variant of E07 known as MinE07 which has the following sequence:
5'-rGrGrA fCrGrG rAfUfU fUrArA fUfCrG fCfCrG fUrArG rArArA rArGfC rAfUrG fUfCrA rArArG fCfCrG rGrArA fCfCrG fUfCfC-3' (SEQ ID NO: 5), wherein "r" represents a natural 2'-OH (RNA) nucleotide and "f" represents a modified 2'-fluoro nucleotide. Thus, in one embodiment, the EGFR binding nucleic acid aptamer comprises an aptamer having the sequence of SEQ ID NO: 5 or a sequence having at least 90% sequence identity to said sequence (such as at least 95, 96, 97, 98 or 99% sequence identity). In a further embodiment, the EGFR binding nucleic acid aptamer comprises an aptamer having the sequence of SEQ ID NO: 5.

Examples of further suitable EGFR binding nucleic acid aptamers include the nucleic acid aptamers of SEQ ID NOS: 1 to 84 described in International Patent Application No. PCT/GB2015/051812. In one embodiment, the nucleic acid aptamer is selected from SEQ ID NO: 79 described in International Patent Application No. PCT/GB2015/051812 which has the following sequence:

```
                                         (SEQ ID NO: 6)
5'-mGmGmG mAfUfU fUAA fUfCmG fCfCmG fUmAmG AmAmA

AmGfC mAfUmG fUfCmA AAmG fCfCmG mGmAA fCfCfC-3';
``` wherein m is 2'-OMe and f is 2'-F. Thus, in one embodiment, the EGFR binding nucleic acid aptamer comprises an aptamer having the sequence of SEQ ID NO: 6 or a sequence having at least 90% sequence identity to said sequence (such as at least 95, 96, 97, 98 or 99% sequence identity). In a further embodiment, the EGFR binding nucleic acid aptamer comprises an aptamer having the sequence of SEQ ID NO: 6.

In a further embodiment, the nucleic acid aptamer comprises a 5' and 3' modified derivative of SEQ ID NO: 6 having the following sequence:
$H_2N$—$(CH_2)_6$-5'-(SEQ ID NO: 6)-3'-idT (hereinafter referred to as SEQ ID NO: 1) or a sequence having at least 90% sequence identity to said sequence (such as at least 95, 96, 97, 98 or 99% sequence identity).

In a further embodiment, the EGFR binding nucleic acid aptamer comprises an aptamer having the sequence of SEQ ID NO: 1.

In an alternative embodiment, the nucleic acid aptamer is a PSMA binding nucleic acid aptamer. Prostate Specific Membrane Antigen (PSMA) is an integral membrane protein with NAALADase enzymatic activity. It is highly expressed on prostate epithelial cells, and known to be upregulated throughout progression of prostate cancer.

In one embodiment, the PSMA binding nucleic acid aptamer is an aptamer which binds with high affinity and specificity to the extra cellular domain of human PSMA. In some embodiments, the PSMA binding nucleic acid aptamer modulates the function of PSMA. In some embodiments, the PSMA binding nucleic acid aptamer modulates NAALADase activity.

Examples of suitable PSMA binding nucleic acid aptamers include those described in Lupold et al (Cancer Res. 2002, Jul. 15; 62(14):4029-33) which describes a series of PSMA binding aptamers of 70 nucleotides in length (A9), and Giangrande et al (WO 2013/012921) which describes suitable truncation of A9 to sequences of down to 41 nucleotides in length whilst maintaining effective binding activity, including the minimised variant of A9 known as A9g which has the following sequence:

```
                                         (SEQ ID NO: 7)
5'-GrGrGrArCfCfGrArArAr ArArGrArCfCfUfGrArCf

UfUfCfUfArUfArCfUfAr ArGrUfCfUfArCfGrUfUf

CfCfCf-3'
``` wherein "r" represents a natural 2'-OH (RNA) nucleotide and "f" represents a modified 2'-fluoro nucleotide. Thus, in one embodiment, the PSMA binding nucleic acid aptamer comprises an aptamer having the sequence of SEQ ID NO: 7 or a sequence having at least 90% sequence identity to said sequence (such as at least 95, 96, 97, 98 or 99% sequence identity). In a further embodiment, the PSMA binding nucleic acid aptamer comprises an aptamer having the sequence of SEQ ID NO: 7.

Examples of further suitable PSMA binding nucleic acid aptamers may be found in US 2009/0105172 and US 2007/0041901. One such example is ARC-2037 described in US 2009/0105172 and having the following sequence:

```
                                              (SEQ ID NO: 8)
5'-CmGmGmAmCfCfGmArArAr ArAmGmAmCmCfUfGrArCf

UfUfCfUfArUfArCfUfArAr GmUmCmUmArCfGmUfUmCm

CmGm-3'
``` wherein "r" represents a natural 2'-OH (RNA) nucleotide, "f" represents a modified 2'-fluoro nucleotide and "m" represents a modified 2'-Omethyl nucleotide.

In a further embodiment, the nucleic acid aptamer comprises a 5' and 3' modified derivative of SEQ ID NO: 8 having the following sequence:

```
    H2N-(CH2)6-5'-(SEQ ID NO: 8)-3'-idT.
```

In a further embodiment, the nucleic acid aptamer comprises a 5' and 3' modified derivative of SEQ ID NO: 7 having the following sequence:

```
    H2N-(CH2)6-5'-(SEQ ID NO: 7)-3'-idT
       (hereinafter referred to as SEQ ID NO: 2)
``` or a sequence having at least 90% sequence identity to said sequence (such as at least 95, 96, 97, 98 or 99% sequence identity). In a further embodiment, the PSMA binding nucleic acid aptamer comprises an aptamer having the sequence of SEQ ID NO: 2.

In an alternative embodiment, the nucleic acid aptamer is a *Pseudomonas aeruginosa* (PA) binding nucleic acid aptamer.

In a further embodiment, the *Pseudomonas aeruginosa* (PA) binding nucleic acid aptamer is selected from a sequence of SEQ ID NO: 9-36 as described in Table 1:

TABLE 1

All oligonucleotides contain the following composition: 2'F-Guanine, 2'methoxy Cytosine, 2'methoxy Uracil, 2'methoxy Adenine.

| Sequence ID | Sequence Origin | Sequence 5' to 3' | No. of nucleosides |
|---|---|---|---|
| SEQ ID NO: 11 | PA21OS | GUGCAGAUAAACGGGAAGGGGUCGGGAA AAAGGGCAAUAUCAAGCGCAAUCUUGU | 55 |
| SEQ ID NO: 12 | PA21CL | GGGGCAGAUAAACGGGAAGGGGUCGGGA AAAAGGGCAAUAUCAAGCGCAAUCUUGU CCC | 59 |
| SEQ ID NO: 13 | PA21C | GUGCAGAUCGGGAAGGUCGGGAAAAGGG CUAUCGCGCAAUCUUGU | 45 |
| SEQ ID NO: 14 | PA21M | GUGCAGAUAAGCGGGAAGGGUUCGGGAA AUUGGGCCUUAUCCCGCUCUAUCUCGU | 55 |
| SEQ ID NO: 9 | PA22OS | GUGCAGAUCCGGGUAUAAUGGGUAGUGG AGGGUUUCGGGCUAUACCAGAUCUUGU | 55 |
| SEQ ID NO: 15 | PA22CL | GGGGCAGAUCCGGGUAUAAUGGGUAGUG GAGGGUUUCGGGCUAUACCAGAUCUUGU CCC | 59 |
| SEQ ID NO: 16 | PA22C | GUGCAGCCGGGAUAAUGUAGUGGAGGGU UUCGGCAUCCAGCUUGU | 45 |
| SEQ ID NO: 17 | PA22M | GUGCUGAUCCGGGUAUCAUGGGUGGUCG AGGGUUUGGCGCGAUACCCGAUCGUGC | 55 |
| SEQ ID NO: 18 | PA22CM | GUGCAGCCGGGAUAAUGGAAACGUGGGA AUGAUCAUCCAGCUUGC | 45 |
| SEQ ID NO: 19 | PA22MC | GUGCUGCCGGGAUCAUGUGGUCGAGGGU UUCGGGAUCCCGCUGC | 45 |
| SEQ ID NO: 20 | PA22CMS | GCCGGGAUAAUGGAAACGUGGGAAUGAU CAUCCAGC | 36 |
| SEQ ID NO: 21 | PA22MCS | GCCGGGAUCAUGUGGUCGAGGGUUUCGG GAUCCCGC | 36 |
| SEQ ID NO: 10 | PA23OS | GUGCAGAUUGGAAAAGGGUAGUGGAUUU GGGAAGGGUUUAGGGUUUCAAUCUUGU | 55 |
| SEQ ID NO: 22 | PA23CL | GGGGCAGAUUGGAAAAGGGUAGUGGAUU UGGGAAGGGUUUAGGGUUUCAAUCUUGU CCC | 59 |
| SEQ ID NO: 23 | PA23C | GUGCAGAUGAAAGGGUAGUAUUGGGAA GGUAGGGUUCAUCUUGU | 45 |
| SEQ ID NO: 24 | PA23M | GUGCGGAUUGGAACAGGGUCUAGGAUUU GGGAAGGUUUUAGGGUUUCAAUCCUGC | 55 |
| SEQ ID NO: 25 | PA23CM | GUGCAGAUGAAAGGGUAGUGUUGGGAA GGCAGGGUUCAUCUUGC | 45 |
| SEQ ID NO: 26 | PA23MC | GUGCGGAUGAACAGGGUCUAAUUGGGAA GGUAGGGUUCAUCUUGC | 45 |
| SEQ ID NO: 27 | PA23MCS | GAUGAAAGGGUAGUGUUGGGAAGGCAG GGUUCAUC | 36 |
| SEQ ID NO: 28 | PA23CMS | GAUGAACAGGGUCUAAUUGGGAAGGUAG GGUUCAUC | 36 |
| SEQ ID NO: 29 | PA24OS | GUGCAGAGUUACACGCCAUGGGAUUUAG GGGAAGGAAGUGGGGGUCGUGUUCUUGU | 56 |
| SEQ ID NO: 30 | PA24CL | GGGGCAGAGUUACACGCCAUGGGAUUUA GGGGAAGGAAGUGGGGGUCGUGUUCUUG UCCC | 60 |
| SEQ ID NO: 31 | PA24M | GUGCUCUGUUACACGCCACGGGAUUGAA GGCAAGAAAGUGGAGGACGUGUUCAAGC | 56 |
| SEQ ID NO: 32 | PA24C | GUGCAGAGUUACGCAUGGGAUUAGGGGA AGGAAUGGGGUCGUUCUUGU | 48 |
| SEQ ID NO: 33 | PA21FL | GGAAGAGGAAAGAAGUGCAGAUAAACGG GAAGGGUCGGGAAAAAGGGCAAUAUCA AGCGCAAUCUUGUGCUCGCGAGGCAAUC A | 85 |

TABLE 1-continued

All oligonucleotides contain the following composition: 2'F-Guanine, 2'methoxy Cytosine, 2'methoxy Uracil, 2'methoxy Adenine.

| Sequence ID | Sequence Origin | Sequence 5' to 3' | No. of nucleosides |
|---|---|---|---|
| SEQ ID NO: 34 | PA22FL | GGAAGAGGAAAGAAGUGCAGAUCCGGGU AUAAUGGGUAGUGGAGGGUUUCGGGCUA UACCAGAUCUUGUGCUCGCGAGGCAAUC A | 85 |
| SEQ ID NO: 35 | PA23FL | GGAAGAGGAAAGAAGUGCAGAUUGGAAA AGGGUAGUGGAUUUGGGAAGGGUUUAGG GUUUCAAUCUUGUGCUCGCGAGGCAAUC A | 85 |
| SEQ ID NO: 36 | PA24FL | GGAAGAGGAAAGAAGUGCAGAGUUACAC GCCAUGGGAUUUAGGGGAAGGAAGUGGG GGUCGUGUUCUUGUGCUCGCGAGGCAAU CA | 86 |

In one embodiment, the *Pseudomonas aeruginosa* (PA) binding nucleic acid aptamer is selected from a sequence of SEQ ID NO: 9 or SEQ ID NO: 10:

```
                              (PA22OS, SEQ ID NO: 9)
5'-GfUmGfCmAmGfAmUmCmCm GfGfGfUmAmUmAmAmUmGf

GfGfUmAmGfUmGfGfAmGf GfGfUmUmUmCmGfGfGfCm

UmAmUmAmCmCmAmGfAmUm CmUmUmGfUm-3';
or
                              (PA23OS, SEQ ID NO: 10)
5'-GfUmGfCmAmGfAmUmUmGf GfAmAmAmAmGfGfGfUmAm

GfUmGfGfAmUmUmGfGf GfAmAmGfGfGfUmUmAm

GfGfGfUmUmCmAmAmUm CmUmUmGfUm-3'
``` wherein "r" represents a natural 2'-OH (RNA) nucleotide, "f" represents a modified 2'-fluoro nucleotide and m represents a modified 2'-methoxy nucleotide. Thus, in one embodiment, the PA binding nucleic acid aptamer comprises an aptamer having the sequence of SEQ ID NO: 9 or SEQ ID NO: 10, or a sequence having at least 90% sequence identity to said sequence (such as at least 95, 96, 97, 98 or 99% sequence identity). In a further embodiment, the PA binding nucleic acid aptamer comprises an aptamer having the sequences of SEQ ID NO: 9 or SEQ ID NO: 10.

In a further embodiment, the nucleic acid aptamer comprises a 5' and 3' modified derivative of SEQ ID NO: 3 or SEQ ID NO: 4 having the following sequence:

```
H2N-(CH2)6-5'-(SEQ ID NO: 9)-3'-idT
(hereinafter referred to as SEQ ID NO: 3)
or H2N-(CH2)6-5'-(SEQ ID NO: 10)-3'-idT
(hereinafter referred to as SEQ ID NO: 4)
``` or a sequence having at least 90% sequence identity to said sequence (such as at least 95, 96, 97, 98 or 99% sequence identity). In a further embodiment, the PA binding nucleic acid aptamer comprises an aptamer having the sequence of SEQ ID NO: 3 or SEQ ID NO: 4.

In a further embodiment, the invention provides a compound of formula (I) which comprises a compound of Examples 1-9 or a pharmaceutically acceptable salt thereof.

It will be appreciated that:
the compounds of Examples 1-4 have specific therapeutic utility in the treatment of cancer;
the compounds of Examples 5-7 have specific therapeutic utility in the treatment of a disease or disorder mediated by PSMA; and
the compounds of Example 8-9 have specific therapeutic utility in the treatment of a disease or disorder mediated and/or caused by *Pseudomonas aeruginosa*;
which can be inferred from the approach demonstrated for nucleic acid aptamers directed to group A *Streptococcus* (GAS) bacteria described in Kristian et al (2015) J. Mol. Med. (2015) 93, 619-631.

In one embodiment, the compound of formula (I) is other than Example 8 and/or Example 9.

A reference to a compound of formula (I) and sub-groups thereof also includes ionic forms, salts, solvates, isomers (including geometric and stereochemical isomers), tautomers, N-oxides, esters, isotopes and protected forms thereof, for example, as discussed below; preferably, the salts or tautomers or isomers or N-oxides or solvates thereof; and more preferably, the salts or tautomers or N-oxides or solvates thereof, even more preferably the salts or tautomers or solvates thereof. Hereinafter, compounds and their ionic forms, salts, solvates, isomers (including geometric and stereochemical isomers), tautomers, N-oxides, esters, isotopes and protected forms thereof as defined in any aspect of the invention (except intermediate compounds in chemical processes) are referred to as "compounds of the invention".

Compounds of formula (I) can exist in the form of salts, for example acid addition salts or, in certain cases salts of organic and inorganic bases such as carboxylate, sulfonate and phosphate salts. All such salts are within the scope of this invention, and references to compounds of formula (I) include the salt forms of the compounds. In one embodiment, the compound of formula (I) exists as the phosphate salt.

The salts of the present invention can be synthesized from the parent compound that contains a basic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt. Another particular salt is the hydrogensulfate salt, also known as a hemisulfate salt.

Salts further include, by way of example only, sodium, potassium, calcium, magnesium, ammonium, tetraalkylammonium, and the like.

It will be appreciated that when the target binding moiety represents a nucleic acid aptamer that the compound of formula (I) will desirably be present as a salt free form to avoid any potential degradation of the nucleic acid aptamer. Thus, in a further embodiment, the invention provides a compound of formula (I) which is the free base of a compound of Examples 1-9.

Where the compounds of formula (I) contain an amine function, these may form quaternary ammonium salts, for example by reaction with an alkylating agent according to methods well known to the skilled person. Such quaternary ammonium compounds are within the scope of formula (I).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salts forms, which may be useful, for example, in the purification or separation of the compounds of the invention, also form part of the invention.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Pharmaceutically acceptable solvates of the compound of the invention are within the scope of the invention.

Compounds of formula (I) containing an amine function may also form N-oxides. A reference herein to a compound of formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (mCPBA), for example, in an inert solvent such as dichloromethane.

It will be appreciated by those skilled in the art that certain protected derivatives of compounds of formula (I), which may be made prior to a final deprotection stage, may not possess pharmacological activity as such, but may, in certain instances, be administered orally or parenterally and thereafter metabolised in the body to form compounds of the invention which are pharmacologically active. Such derivatives may therefore be described as "prodrugs". All such prodrugs of compounds of the invention are included within the scope of the invention. Examples of pro-drug functionality suitable for the compounds of the present invention are described in Drugs of Today, Volume 19, Number 9, 1983, pp 499-538 and in Topics in Chemistry, Chapter 31, pp 306-316 and in "Design of Prodrugs" by H. Bundgaard, Elsevier, 1985, Chapter 1 (the disclosures in which documents are incorporated herein by reference). It will further be appreciated by those skilled in the art, that certain moieties, known to those skilled in the art as "pro-moieties", for example as described by H. Bundgaard in "Design of Prodrugs" (the disclosure in which document is incorporated herein by reference) may be placed on appropriate functionalities when such functionalities are present within compounds of the invention.

Also included within the scope of the compound and various salts of the invention are polymorphs thereof.

Compounds of formula (I) may exist in a number of different geometric isomeric, and tautomeric forms and references to compounds of formula (I) include all such forms. For the avoidance of doubt, where a compound can exist in one of several geometric isomeric or tautomeric forms and only one is specifically described or shown, all others are nevertheless embraced by formula (I).

The present invention includes all pharmaceutically acceptable isotopically-labeled compounds of the invention, i.e. compounds of formula (I), wherein one or more atoms are replaced by atoms having the same atomic number, but an atomic mass or mass number different from the atomic mass or mass number usually found in nature.

Examples of isotopes suitable for inclusion in the compounds of the invention comprise isotopes of hydrogen, such as $^2$H (D) and $^3$H (T), carbon, such as $^{11}$C, $^{13}$C and $^{14}$C, fluorine, such as $^{18}$F, nitrogen, such as $^{13}$N and $^{15}$N, oxygen, such as $^{15}$O, $^{17}$O and $^{18}$O.

Certain isotopically-labelled compounds of formula (I), for example, those incorporating a radioactive isotope, are useful in drug and/or substrate tissue distribution studies. The compounds of formula (I) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^3$H (T), and carbon-14, i.e. $^{14}$C, are particularly useful for this purpose in view of their ease of incorporation and ready means of detection.

Substitution with heavier isotopes such as deuterium, i.e. $^2$H (D), may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining target occupancy.

Isotopically-labeled compounds of formula (I) can generally be prepared by conventional techniques known to those skilled in the art or by processes analogous to those described in the accompanying Examples and Preparations using appropriate isotopically-labeled reagents in place of the non-labeled reagent previously employed.

Methods for the Preparation of Compounds of Formula (I)

In this section, as in all other sections of this application unless the context indicates otherwise, references to formula (I) also include all other sub-groups and examples thereof as defined herein.

The compounds pertaining to the invention described herein may be prepared in a stepwise synthetic sequence as illustrated in the Processes and Schemes below. The syntheses involve the preparation of various central constructs which then enable the choice of branching and length of linker with which to connect the two binding moieties. Compounds of the formula (I) can be prepared in accordance with synthetic methods well known to the skilled person. For example, one skilled in the art will appreciate that the chemical steps and choice of protecting groups may be managed in any order to enable synthetic success.

According to a further aspect of the invention there is provided a process for preparing a compound of formula (I) as hereinbefore defined which comprises:

(a) preparing a compound of formula (I) wherein $Y_1$ represents —CONH— (i.e. a compound of formula (IA)) by reacting a compound of formula (II) with a compound of formula (III):

with either phosphate containing reagents, triazine-based reagents or carbodiimide containing reagents in the presence of an organic base in an organic solvent. Alternatively the carboxylic acid may be activated with N-hydroxysuccinimide. Preferred conditions comprise DMTMM (4-(4,6-dimethoxy-1,3,5-triazin-2-yl)-4-methylmorpholin-4-ium tetrafluoroborate salt) with an inorganic base in a solvent such as DMF, or using a combination of N-hydroxysuccinimide with N,N-diisopropylcarbodiimide in an organic solvent with an aqueous solution of an inorganic base.

Process (b) typically comprises interconversion procedures known by one skilled in the art. For example, in compounds of formula (I), a first substituent may be converted by methods known by one skilled in the art into a second, alternative substituent. A wide range of well known functional group interconversions are known by a person skilled in the art for converting a precursor compound to a compound of formula (I) and are described in *Advanced Organic Chemistry* by Jerry March, 4$^{th}$ Edition, John Wiley & Sons, 1992. For example possible metal catalysed functionalisations such as using organo-tin reagents (the Stille reaction), Grignard reagents and reactions with nitrogen nucleophiles are described in 'Palladium Reagents and Catalysts' [Jiro Tsuji, Wiley, ISBN 0-470-85032-9] and Handbook of OrganoPalladium Chemistry for Organic Synthesis [Volume 1, Edited by Ei-ichi Negishi, Wiley, ISBN 0-471-31506-0].

If appropriate, the reactions previously described in processes (a) and (b) are followed or preceded by one or more reactions known to the skilled of the art and are performed in an appropriate order to achieve the requisite substitutions defined above to afford other compounds of formula (I).

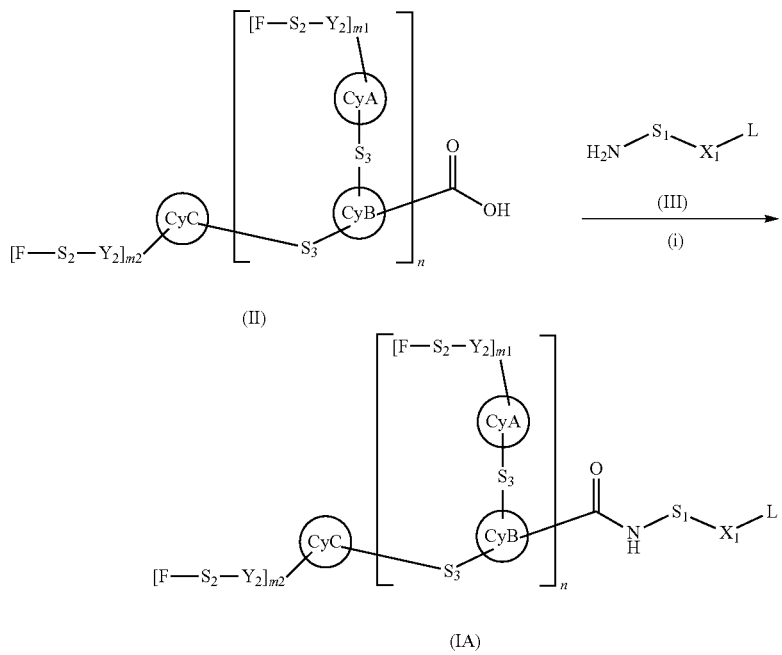

wherein $S_2$, $S_3$, $Y_2$, m1, m2, n, CyA, CyB, CyC, $S_1$, $X_1$, L and F are as defined hereinbefore; and/or (b) interconversion of a compound of formula (I) or protected derivative thereof to a further compound of formula (I) or protected derivative thereof.

Process (a) typically comprises an amide bond formation reaction which comprises activation of the carboxylic acid Non-limiting examples of such reactions whose conditions can be found in the literature include:
protection of reactive functions,
deprotection of reactive functions,
halogenation,
dehalogenation,
dealkylation, alkylation and arylation of amine, aniline, alcohol and phenol,
Mitsunobu reaction on hydroxyl groups,
cycloaddition reactions on appropriate groups,
reduction of nitro, esters, cyano, aldehydes,
transition metal-catalyzed coupling reactions,
acylation,
sulfonylation/introduction of sulfonyl groups,
saponification/hydrolysis of ester groups,
amidification or transesterification of ester groups,
esterification or amidification of carboxylic groups,
halogen exchange,
nucleophilic substitution with amine, thiol or alcohol,
reductive amination,
oxime formation on carbonyl and hydroxylamine groups,
S-oxidation,
N-oxidation,
salification.

Compounds of formula (II) (wherein $S_3$ contains a —CONH— group) may be prepared according to the methods described in Scheme 1 from compounds of formula (III) and (IV), gation between compounds of formula (V) and compounds of formula (IV).

Compounds of formula (II) may be prepared from compounds of formula (IV) and (V) according to process steps (ii) and (iii), an amide bond formation step comprising activation of the carboxylic acid with either phosphate containing reagents, triazine-based reagents, peptide coupling reagents (such as hydroxy-azabenzotriazole containing reagents) or carbodiimide containing reagents in the presence of an organic base in an organic solvent as described for process (a) hereinbefore, followed by a suitable deprotection reaction. Preferred conditions for the amide bond formation step comprise HATU in DMF with an organic base such as triethylamine. Wherein PG comprises benzyl, the deprotection reaction may be mediated by catalytic hydrogenation. Preferred conditions comprise 10% Pd/C in MeOH/EtOH or water or any combination thereof under an atmosphere of hydrogen (from between 15-70 psi). Alternatively, deprotection may be mediated by a phase transfer reaction. Preferred conditions comprise triethylamine and water at room temperature for 16 hours.

Scheme 1

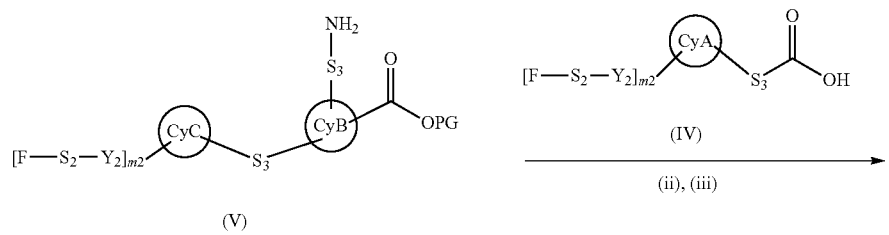

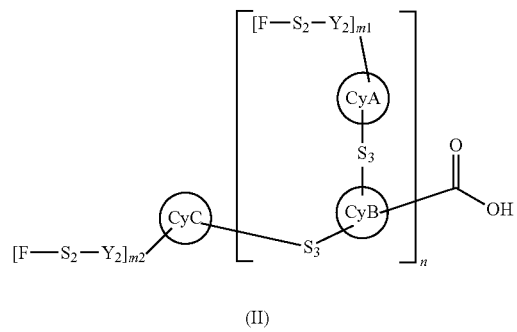

wherein m1, m2, CyA, CyB, CyC, $S_2$, $Y_2$ and F are as defined hereinbefore, n is 1, PG is a protecting group comprising benzyl and $S_3$ is terminated with either a carboxylic acid or an amine to enable an amide bond conju- Compounds of formula (II) (wherein $S_5$ contains a —CONH— group) may also be prepared according to the methods described in Scheme 2 from compounds of formula (VI) and (IV),

Scheme 2

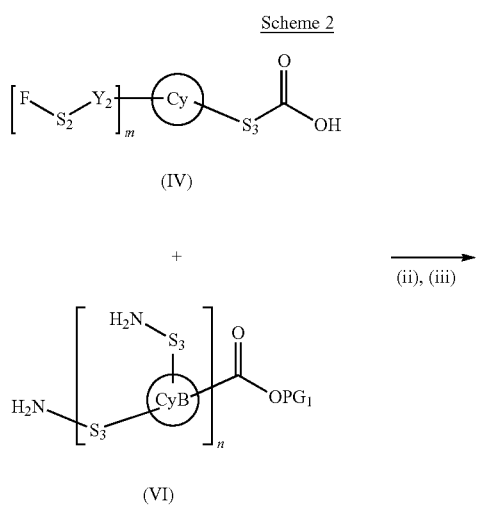

(IV)

+

(VI)

→ (ii), (iii)

wherein m1, m2, CyA, CyB, CyC, $S_2$, $Y_2$ and F are as defined hereinbefore, $PG_1$ is a protecting group comprising benzyl and $S_3$ is terminated with either a carboxylic acid or an amine to enable an amide bond conjugation between compounds of formula (VI) and compounds of formula (IV).

Compounds of formula (II) may be prepared from compounds of formula (IV) and (VI) according to process steps (ii) and (iii), an amide bond formation step followed by a suitable deprotection step as described hereinbefore in Scheme 1.

Compounds of formula (V) (wherein Cy may be CyA or CyC, and $S_3$ contains a —CONH— group) may be prepared according to the methods described in Scheme 3 from compounds of formula (IV) and (VII),

Scheme 3

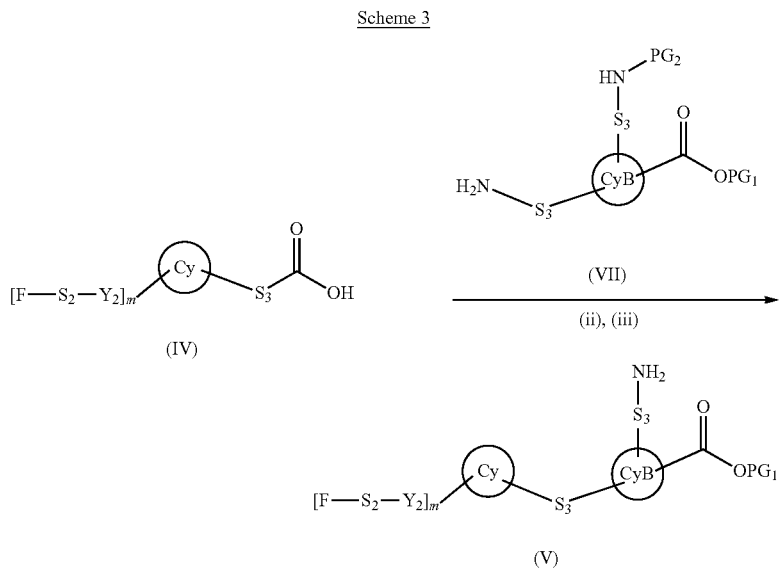

(IV)

(VII)

→ (ii), (iii)

(V)

-continued

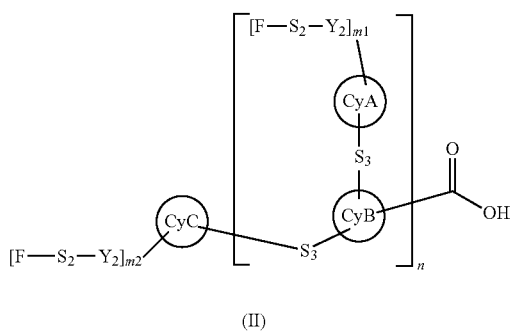

(II)

wherein m, Cy, $S_2$, $Y_2$ and F are as defined hereinbefore, PG is a protecting group comprising benzyl, $PG_2$ is a protecting group comprising monomethoxytrityl (MMTr) and $S_3$ is terminated with either a carboxylic acid or an amine to enable an amide bond conjugation between compounds of formula (IV) and compounds of formula (VII).

Compounds of formula (V) may be prepared from compounds of formula (IV) and (VII) according to process steps (ii) and (iii), an amide bond formation step followed by a suitable deprotection step as described hereinbefore in Scheme 1. Wherein $PG_2$ is MMTr, preferred deprotection conditions comprise 0.2M aqueous HCl (pH=3-4) at room temperature.

Compounds of formula (IV) may also be prepared according to the methods described in Scheme 4 from compounds of formula (XI), (VI) and (XII) or (XI), (VIII) and (VI).

Scheme 4

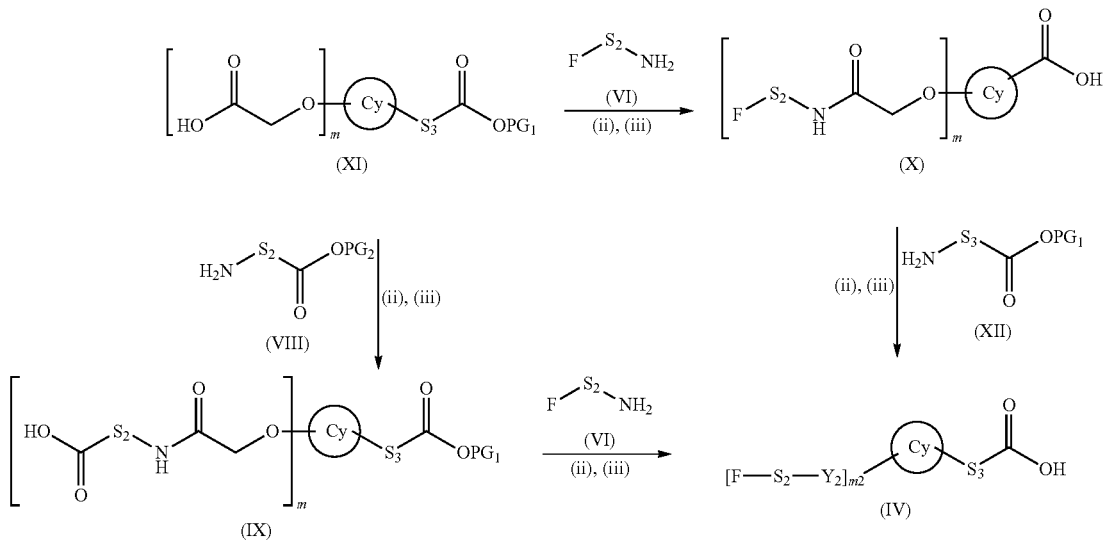

wherein m1, Cy, $S_2$, $S_3$ and F are as defined hereinbefore, $PG_1$ is a protecting group comprising benzyl and $PG_2$ is an orthogonal protecting group comprising tert-butyl.

Compounds of formula (IV) may be prepared from compounds of formula (X) and (XII) according to process steps (ii) and (iii), an amide bond formation step as described in Scheme 1 hereinbefore, followed by a suitable deprotection reaction. Wherein $PG_1$ comprises benzyl, the deprotection reaction is mediated by catalytic hydrogenation. Preferred conditions comprise 10% Pd/C in MeOH/EtOH or water or any combination thereof under an atmosphere of hydrogen (from between 15-70 psi). Alternatively, deprotection may be mediated by a phase transfer reaction. Preferred conditions comprise TEA and water at room temperature for 16 hours.

Compounds of formula (IV) may also be prepared from compounds of formula (IX) and (VI) according to process steps (ii) and (iii), an amide bond formation step as described in Scheme 1 hereinbefore, followed by a suitable deprotection reaction as described hereinbefore.

Compounds of formula (X) may be prepared from compounds of formula (XI) and (VI) according to process steps (ii) and (iii) as described for Scheme 1 hereinbefore and employing suitable deprotection conditions as described above.

Compounds of formula (IX) may be prepared from compounds of formula (VIII) and (XI) according to process steps (ii) and (iii) as described for Scheme 1 hereinbefore and employing suitable deprotection conditions as described above. Wherein $PG_2$ comprises tert-butyl, an acid mediated deprotection reaction is employed. Preferred conditions comprise TFA, 4M HCl in dioxane, or 37% HCl in water with a co-solvent of DCM or water as necessary.

Compounds of formula (XI) may be prepared according to the methods described in Scheme 5 from compounds of formula (XIV) and (XIII).

Scheme 5

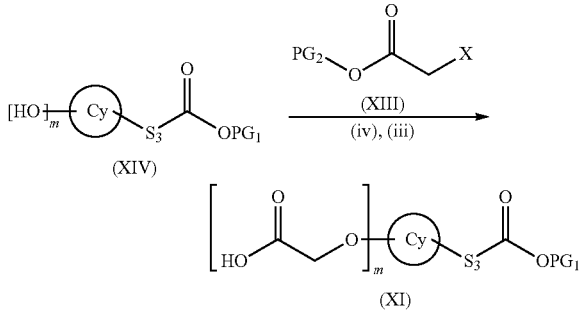

wherein m, Cy and $S_3$ are as defined hereinbefore, $PG_1$ is a protecting group comprising benzyl, $PG_2$ is an orthogonal protecting group comprising tert-butyl and X is Cl, Br or I.

Compounds of formula (XI) may be prepared from compounds of formula (XIII) and (XIV) according to process step (iv), an alkylation reaction followed by a suitable deprotection reaction. Typical alkylation conditions comprise an inorganic base in a polar organic solvent at room temperature. Preferred conditions comprise potassium carbonate in DMF. Wherein $PG_2$ is tert-butyl, suitable deprotection conditions are as described hereinbefore for Scheme 1.

When Cy is bi-phenyl, or triphenyl, compounds of formulae (VI), (VII) or (XIV) may be prepared by employment of a Suzuki reaction to construct the bi/tri-phenyl unit. Preferred conditions comprise tetrakistriphenyl phosphine palladium (0) or [1,1'-bis(diphenylphosphino)ferrocene]dichloropalladium (II) complex with dichloromethane with sodium carbonate, potassium acetate or sodium bicarbonate in dioxane and water at 100-110° C. When suitable required protecting groups are employed, such as TBS, such protecting groups may be deprotected using a fluoride mediated deprotection. Preferred conditions comprise TBAF in THF at room temperature.

Compounds of formula (III), (VI), (VII), (XII), (VIII), (XIV) or (XIII) are either commercially available or prepared according to the methods described herein.

It will be appreciated that certain intermediates described herein represent novel compounds not previously known in the art. Thus, according to a further aspect of the invention there is provided an intermediate compound selected from a compound of formula (II) and (VII) as defined hereinbefore.

One skilled in the art will appreciate that one may choose the appropriate combination of steps described in processes (a) and (b) or Schemes 1 to 5 to generate the highest yields for the Examples and Preparations described herein, or to generate Examples wherein n>1.

Pharmaceutical Compositions

While it is possible for the compound of formula (I) to be administered alone, it is preferable to present it as a pharmaceutical composition (e.g. formulation).

Thus, according to a further aspect, the invention provides a pharmaceutical composition, and methods of making a pharmaceutical composition comprising (e.g admixing) at least one compound of the invention together with one or more pharmaceutically acceptable excipients and optionally other therapeutic or prophylactic agents, as described herein.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity (i.e. generally recognised as safe (GRAS)), irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing compounds of the invention can be formulated in accordance with known techniques, see for example, Remington's Pharmaceutical Sciences, Mack Publishing Company, Easton, Pa., USA.

The pharmaceutical compositions can be in any form suitable for parenteral, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, inter alia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and prefilled syringes, and may be stored in a freeze-dried (lyophilised) condition requiring only the addition of the sterile liquid carrier, for example water for injections, immediately prior to use.

The pharmaceutical formulation can be prepared by lyophilising a compound of the invention. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use.

Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening or coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various anti-bacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminium monostearate and gelatin.

In one preferred embodiment of the invention, the pharmaceutical composition is in a form suitable for i.v. administration, for example by injection or infusion. For intravenous or subcutaneous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for subcutaneous (s.c.) administration.

The compound of the invention may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. Aug. 1, (2006) 5, 1909.

The pharmaceutical compositions typically comprise from approximately 1% (w/w) to approximately 95% (w/w) active ingredient and from 99% (w/w) to 5% (w/w) of a pharmaceutically acceptable excipient or combination of excipients. Preferably, the compositions comprise from approximately 20% (w/w) to approximately 90% (w/w) active ingredient and from 80% (w/w) to 10% of a pharmaceutically acceptable excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, tablets or capsules.

The pharmaceutically acceptable excipient(s) can be selected according to the desired physical form of the formulation and can, for example, be selected from diluents (e.g solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral or subcutaneous formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions. One example of a patient pack includes a prefilled syringe. Such pre-filled syringes already contain the drug substance. The front end portion of a pre-filled syringe to which a needle is to be attached is sealed with a nozzle cap. Prior to injection, the nozzle cap is removed from the front end portion and a needle is attached thereto. A gasket is then slid by pushing a plunger rod toward the front end portion so that the drug is expelled.

Compositions for nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Solutions of the active compound may also be used for rectal administration.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compound of the invention will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams to 1 gram, e.g. 50 milligrams to 500 milligrams), or 1 microgram to 20 milligrams (for example 1 microgram to 10 milligrams, e.g. 0.1 milligrams to 2 milligrams of active ingredient).

The active compound will be administered to a patient in need thereof (for example a human or animal patient) in an amount sufficient to achieve the desired therapeutic effect.

Therapeutic Uses

According to a further aspect of the invention, there is provided a compound of formula (I) as defined herein for use in therapy.

It will be appreciated that the therapeutic use of the compounds of the invention is determined by the selection of the nucleic acid aptamer. For example, in the embodiment when the nucleic acid aptamer is an EGFR binding nucleic acid aptamer, the compound of formula (I) is for use in the treatment of cancer.

In addition, in the embodiment when the nucleic acid aptamer is PSMA binding nucleic acid aptamer, the compound of formula (I) is for use in the treatment of a disease or disorder mediated by PSMA.

Furthermore, in the embodiment when the nucleic acid aptamer is a *Pseudomonas aeruginosa* (PA) binding nucleic acid aptamer, the compound of formula (I) is for use in the treatment of a disease or disorder mediated by *Pseudomonas aeruginosa*.

According to a further aspect of the invention, there is provided a compound of formula (I) as defined herein wherein L represents an EGFR binding nucleic acid aptamer for use in the treatment of cancer.

According to a further aspect of the invention, there is provided a method of treating cancer which comprises administering to an individual in need thereof a compound of formula (I) as defined herein wherein L represents an EGFR binding nucleic acid aptamer.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and premalignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenousleukemia [AML], chronic myelogenousleukemia [CML], chronic myelomonocyticleukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocyticleukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcomaprotuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

In one embodiment, the cancer is selected from lung, head and neck as well as colorectal cancer.

Examples of other anticancer therapeutic agents or treatments that may be administered together (whether concurrently or at different time intervals) with the compound of the invention include but are not limited to:

Topoisomerase I inhibitors;
Antimetabolites;
Tubulin targeting agents;
DNA binder and topoisomerase II inhibitors;
Alkylating Agents;
Monoclonal Antibodies;
Anti-Hormones;
Signal Transduction Inhibitors;
Proteasome Inhibitors;
DNA methyl transferases;
Cytokines and retinoids;
Chromatin targeted therapies;
Radiotherapy; and
Other therapeutic or prophylactic agents, such as immunotherapy agents.

The compound of the invention may also be administered in conjunction with non-chemotherapeutic treatments such as radiotherapy, photodynamic therapy, gene therapy; surgery and controlled diets.

For use in combination therapy with another chemotherapeutic agent, the compound of the invention and one, two, three, four or more other therapeutic agents can be, for example, formulated together in a dosage form containing two, three, four or more therapeutic agents i.e. in a unitary pharmaceutical composition containing all components. In an alternative embodiment, the individual therapeutic agents may be formulated separately and presented together in the form of a kit, optionally with instructions for their use.

According to a further aspect of the invention, there is provided a compound of formula (I) as defined herein wherein L represents a PSMA binding nucleic acid aptamer for use in the treatment of a disease or disorder mediated by PSMA.

According to a further aspect of the invention, there is provided a method of treating a disease or disorder mediated by PSMA which comprises administering to an individual in need thereof a compound of formula (I) as defined herein wherein L represents a PSMA binding nucleic acid aptamer.

In one embodiment, the PSMA is mammalian PSMA. In a further embodiment, the mammalian PSMA is human PSMA.

In one embodiment, the disease or disorder mediated by PSMA is selected from: cancer, neuropathic and inflammatory pain, head injury, stroke, schizophrenia, diabetic neuropathy, drug addiction, amyotrophic lateral sclerosis and neurodegenerative diseases such as Parkinson's disease and Huntington's disease.

In a further embodiment, the disease or disorder mediated by PSMA is selected from cancer as defined hereinbefore. In a yet further embodiment, the disease or disorder mediated by PSMA is selected from prostate cancer, such as castrate-resistant prostate cancer (CRPC) and hormone-refractory prostate cancer (HRPC).

According to a further aspect of the invention, there is provided a compound of formula (I) as defined herein wherein L represents a *Pseudomonas aeruginosa* (PA) binding nucleic acid aptamer for use in the treatment of a disease or disorder mediated by *Pseudomonas aeruginosa*.

According to a further aspect of the invention, there is provided a method of treating a disease or disorder mediated by *Pseudomonas aeruginosa* which comprises administering to an individual in need thereof a compound of formula (I) as defined herein wherein L represents a *Pseudomonas aeruginosa* (PA) binding nucleic acid aptamer.

According to a further aspect of the invention, there is provided a method for preventing or treating a *P. aeruginosa* infection. In certain embodiments, the infection is a lung infection, a burn infection, a wound infection, an ocular infection, a bone infection, a blood infection or a skin infection, or a combination of said infections. According to a further aspect of the invention, there is provided a method for treating a patient suffering from hospital acquired pneumonia (HAP), ventilator associated pneumonia (VAP), burn injury, cystic fibrosis, corneal infection or a combination thereof.

According to a further aspect of the invention, there is provided a method for preventing or treating a *P. aeruginosa* infection which comprises administering to an individual in need thereof a compound of formula (I) as defined herein wherein L represents a *Pseudomonas aeruginosa* (PA) binding nucleic acid aptamer. In certain embodiments, the infection is a lung infection, a burn infection, a wound infection, an ocular infection, a bone infection, a blood infection or a skin infection, or a combination of said infections. According to a further aspect of the invention, there is provided a method for treating a patient suffering from hospital acquired pneumonia (HAP), ventilator associated pneumonia (VAP), burn injury, cystic fibrosis, corneal infection or a combination thereof which comprises administering to an individual in need thereof a compound of formula (I) as defined herein wherein L represents a *Pseudomonas aeruginosa* (PA) binding nucleic acid aptamer.

The compound of the invention is generally administered to a subject in need of such administration, for example a human or animal patient, preferably a human.

The compound of the invention will typically be administered in amounts that are therapeutically or prophylactically useful and which generally are non-toxic. However, in certain situations (for example in the case of life threatening diseases), the benefits of administering a compound of the invention may outweigh the disadvantages of any toxic effects or side effects, in which case it may be considered desirable to administer a compound of the invention in amounts that are associated with a degree of toxicity.

The compound of the invention may be administered over a prolonged term (i.e. chronic administration) to maintain beneficial therapeutic effects or may be administered for a short period only (i.e. acute administration). Alternatively they may be administered in a continuous manner or in a manner that provides intermittent dosing (e.g. a pulsatile manner).

A typical daily dose of the compound of the invention can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the invention can either be administered on a daily basis or on a repeat basis every 2, or 3, or 4, or 5, or 6, or 7, or 10 or 14, or 21, or 28 days for example. Alternatively, the compound of the invention can be administered by infusion, multiple times per day.

The compound of the invention may be administered in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound of the invention may be administered once or more than once each day. The compound of the invention can be administered continuously (i.e. taken every day without a break for the duration of the treatment regimen). Alternatively, the compound of the invention can be administered intermittently (i.e. taken continuously for a given period such as a week, then discontinued for a period such as a week and then taken continuously for another period such as a week and so on throughout the duration of the treatment regimen). Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient will be given an infusion of a compound of the invention for periods of one hour daily for up to ten days in particular up to five days for one week, and the treatment repeated at a desired interval such as two to four weeks, in particular every three weeks.

More particularly, a patient may be given an infusion of a compound of the invention for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, and in particular a continuous infusion of 24 hours to 72 hours.

Ultimately, however, the quantity of compound of the invention administered and the type of composition used will be commensurate with the nature of the disease or physiological condition being treated and will be at the discretion of the physician.

It will be appreciated that the compound of the invention can be used as a single agent or in combination with other therapeutic agents. Combination experiments can be performed, for example, as described in Chou T C, Talalay P. Quantitative analysis of dose-effect relationships: the combined effects of multiple drugs or enzyme inhibitors. Adv Enzyme Regulat 1984; 22: 27-55.

Where the compound of the invention is administered in combination therapy with one, two, three, four or more other therapeutic agents (preferably one or two, more preferably one), the agents can be administered simultaneously or sequentially. In the latter case, the two or more agents will be administered within a period and in an amount and manner that is sufficient to ensure that an advantageous or synergistic effect is achieved. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s). These dosages may be administered for example once, twice or more per course of treatment, which may be repeated for example every 7, 14, 21 or 28 days.

It will be appreciated that the preferred method and order of administration and the respective dosage amounts and regimes for each component of the combination will depend on the particular other medicinal agent and compound of the invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound of the invention and the one or more other therapeutic agent(s) when given as a combination may be determined by the person skilled in the art. Said ratio and the exact dosage and frequency of administration depends on the particular compound of the invention and the other therapeutic agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compound of present invention. A particular weight ratio for the compound of the invention and another therapeutic agent may range from 1/10 to 10/1, more in particular from 1/5 to 5/1, even more in particular from 1/3 to 3/1.

EXAMPLES

The invention will now be illustrated, but not limited, by reference to the specific embodiments described in the following examples. Compounds are named using an automated naming package such as AutoNom (MDL) or ChemDraw or are as named by the chemical supplier.

The following synthetic procedures are provided for illustration of the methods used; for a given preparation or step the precursor used may not necessarily derive from the individual batch synthesised according to the step in the description given.

Analytical Methods

LCMS

System 1: LCMS Agilent 1100 (quaternary pump); mass spectrometer: Waters Micromass ZQ
  Column: XBridge C18 4.6×50 mm, 5 µm.
  Solvent: A=water; B=acetonitrile, C=10 mm ammonium formate in water; D=0.05% formic acid in acetonitrile
  Column temperature: 25° C., injection volume: 5 µL LCMS Method A: 4.5 Minute Acidic Run

| Time (mins) | A (%) | B (%) | C (%) | D (%) | Flow (mL/min) |
|---|---|---|---|---|---|
| 0 | 95 | 0 | 0 | 5 | 2.0 |
| 3.5 | 0 | 95 | 0 | 5 | 2.0 |
| 4.5 | 0 | 95 | 0 | 5 | 2.0 |
| 4.6 | 95 | 0 | 0 | 5 | 2.0 |

LCMS Method B: 4.5 Minute Buffered Run

| Time (mins) | A (%) | B (%) | C (%) | D (%) | Flow (mL/min) |
|---|---|---|---|---|---|
| 0 | 0 | 5 | 95 | 0 | 2.0 |
| 3.5 | 0 | 95 | 5 | 0 | 2.0 |
| 4.5 | 0 | 95 | 5 | 0 | 2.0 |
| 4.6 | 0 | 5 | 95 | 0 | 2.0 |

LCMS Method C: 8 Minute Acidic Run

| Time (mins) | A (%) | B (%) | C (%) | D (%) | Flow (mL/min) |
|---|---|---|---|---|---|
| 0 | 95 | 0 | 0 | 5 | 2.0 |
| 3.5 | 5 | 90 | 0 | 5 | 2.0 |
| 8.0 | 5 | 90 | 0 | 5 | 2.0 |
| 8.10 | 95 | 0 | 0 | 5 | 2.0 |

LCMS Method D: 4.5 Minute Acidic Run

System 2: LCMS Agilent 1100 (quaternary pump); mass spectrometer: PE SCIEX API 2000 MS/MS
  Column: Agilent Poroshell 120 column, SB-C18, 4.6 mm×30 mm, 2.7 µm
  Solvent: A=water; B=0.1% formic acid in acetonitrile
  Column temperature: 20° C., injection volume: 5 µL

| Time (mins) | A (%) | B (%) | C (%) | D (%) | Flow (mL/min) |
|---|---|---|---|---|---|
| 0.5 | 95 | 5 | 0 | 5 | 2.0 |
| 1.5 | 0 | 100 | 0 | 5 | 2.0 |
| 4.0 | 0 | 100 | 0 | 5 | 2.0 |
| 4.3 | 95 | 5 | | | |
| 4.5 | 95 | 5 | 0 | 5 | 2.0 |

NMR

NMR details were recorded on an Oxford Instruments AS400 or Bruker Avance III Ultrashield plus 400 MHz.

Abbreviations

Wherein the following abbreviations have been used, the following meanings apply:
AcOH is acetic acid;
aq. is aqueous;
Bn is benzyl;
Boc is tert-butyloxycarbonyl;
br s is broad singlet;
b is chemical shift in ppm;
d is doublet;
dd is doublet of doublets;
DCM is dichloromethane;
DMF is dimethylformamide;
DMT is dimercaptotriazine;
DMTMM is 4-(4,6-Dimethoxy-1,3,5-triazin-2-yl)-4-methylmorpholinium chloride or tetrafluoroborate;
DMSO is dimethylsulphoxide;
DMSO-$d_6$ is perdeuterated dimethylsulphoxide NMR solvent;
EDC is N-(3-dimethylaminopropyl)-N'-ethylcarbodiimide;
Eq is equivalents;
EtOAc is ethyl acetate;
HATU is O-(7-azabenzotriazol-1-yl)-N,N,N',N'-tetramethyluronium hexafluorophosphate;
HCl is hydrogen chloride
HFIP is hexafluoroisopropanol;
HOBt is hydroxybenzotriazole;
HPLC is high pressure liquid chromatography;
[Ir(OMe)(COD)]$_2$ is (1,5-cyclooctadiene)(methoxy)iridium (I) dimer;
$K_2CO_3$ is potassium carbonate;
p is micro;
m is multiplet;
MeCN is acetonitrile;
MeOH is methanol;
mins is minutes;
mL is millilitre;
MMTr is monomethoxytrityl;
MS is mass spectrometry;
$MgSO_4$ is magnesium sulfate;
NaOH is sodium hydroxide;
$NH_3$ or $NH_4OH$ is ammonia or ammonium hydroxide (28% aqueous solution);
NMR is nuclear magnetic resonance;
Pd/C is (typically 5%-10%) palladium on charcoal hydrogenation catalyst (water-wet);

Pd(dppf)Cl$_2$ is [1,1'-bis(diphenylphosphino)ferrocene]dichloropalladium (11);
Pd(PPh$_3$)$_4$ is tetrakis triphenylphosphine palladium (0);
ppm is parts per million;
q is quartet;
RNA is ribonucleic acid;
Rt is retention time;
s is singlet;
t is triplet;
TBAF is tetra-n-butylammonium fluoride;
TBME is tert-butyl methyl ether;
tBu is tert-butyl;
TEA is triethylamine;
TEAA is triethylammonium acetate;
TBS is tert-butyldimethylsilyloxy;
TFA is trifluoroacetic acid;
TFAA is trifluoroacetic anhydride; and
THF is tetrahydrofuran Wherein alpha-Gal is referred to, the following intermediate applies: 3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl) tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amine

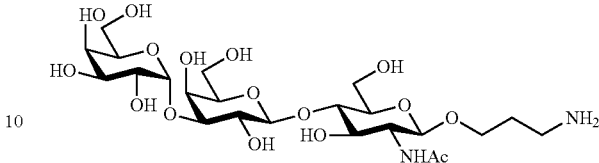

This intermediate may be prepared according to the methods described by Bovin et al (Mendeleev Communications (2002), (4), 143-145).

Preparations 1-51 describe the methods used to prepare intermediates from the key linker clusters required for conjugation into the Examples, as described by Processes (a) and (b) and Schemes 1-5 as described hereinbefore.

Preparation 1
Double Cluster 1

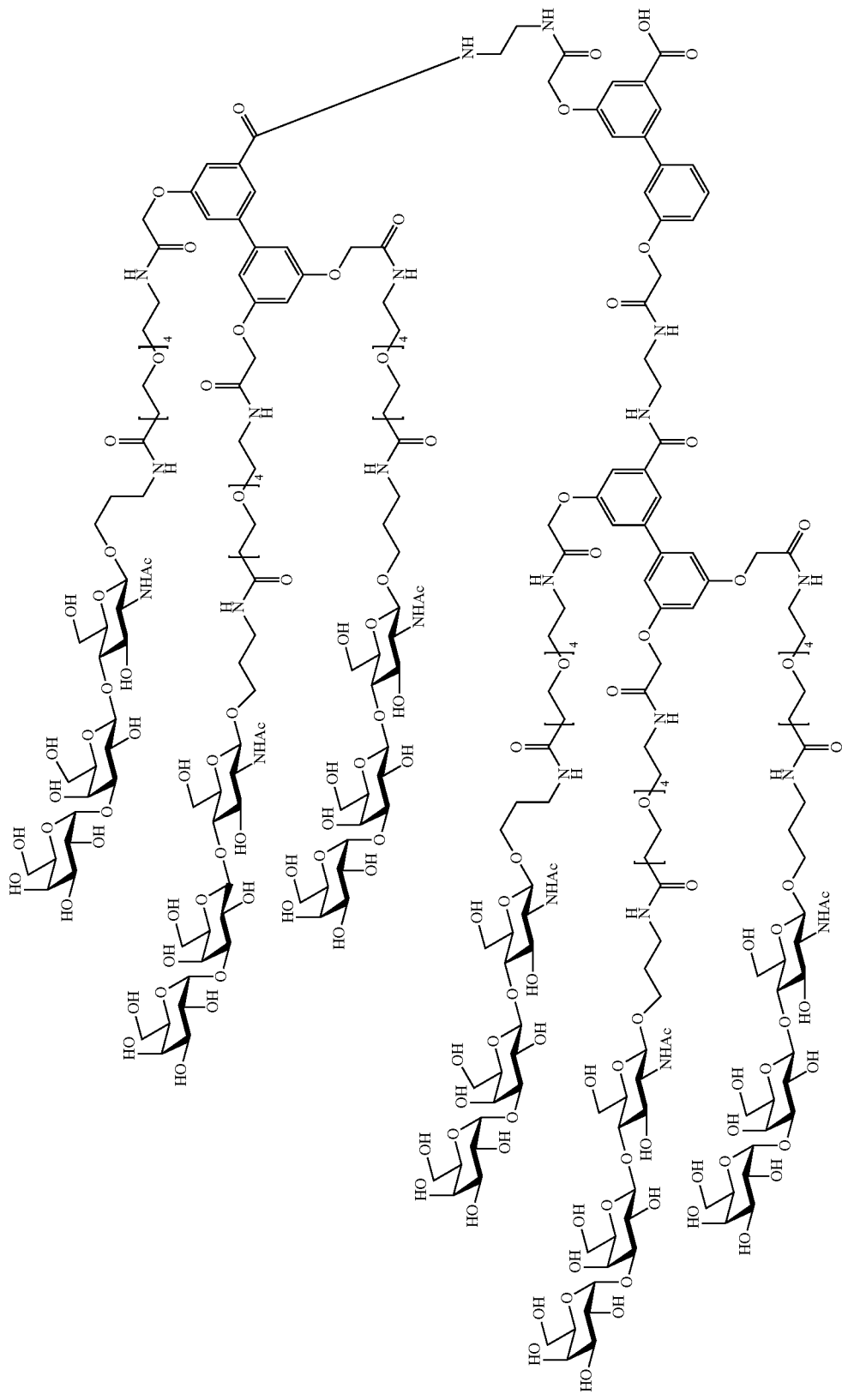

Step 1

To a solution of Preparation 3 (51.3 mg, 17.6 µmol) in a mixture of DMSO (500 µL) and DMF (3.5 mL) residue was added triethylamine (5.10 µL, 36.5 µmol) followed by a solution of Preparation 2 (50 mg, 14.6 µmol) in DMSO (500 µL). HATU (6.69 mg, 17.6 µL) was added and the reaction was stirred at room temperature for 30 minutes. The reaction was concentrated in vacuo and purified using reverse phase column chromatography eluting with 5-40% MeCN in water with 0.1% ammonia to afford the benzyl intermediate residue (39 mg, 42%).

LCMS Method B: Rt=1.79 minutes, ES MS m/z 1579.9 [M+4H]$^+$/4, theoretical mass: 6315

Step 2

The residue from Step 1 was dissolved in water (1.5 mL) and treated with triethylamine (1.5 mL). The biphasic mixture was stirred at room temperature for overnight before concentrating to low volume (0.5 mL). The residue was purified using reverse phase column chromatography eluting with 5-40% MeCN in water with 0.1% ammonia to afford the title compound as a colourless solid (31 mg, 81%).

LCMS Method B: Rt=1.59 mins, ES$^+$ MS m/z 1556.6 [M+4H]$^+$/4, theoretical mass: 6224.6

Preparation 2

Precursor to Double Cluster 1

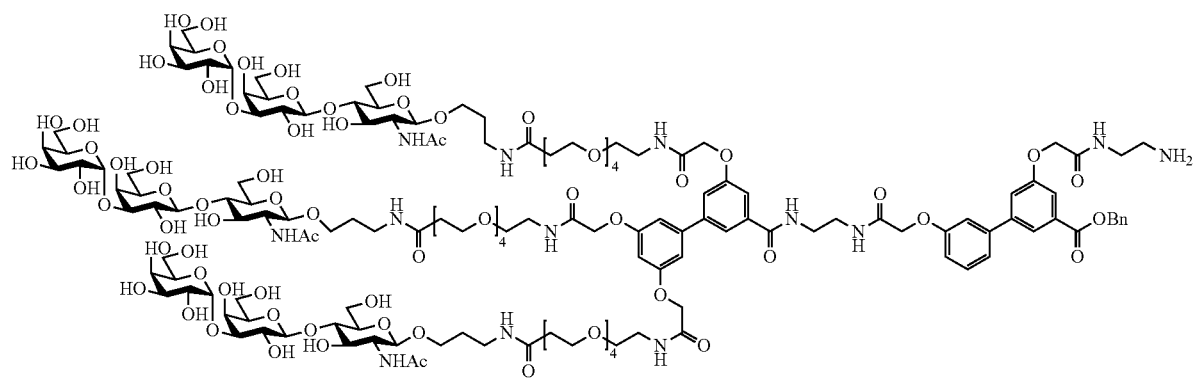

Step 1

To a solution of Preparation 3 (60 mg, 20.6 µmol) in a mixture of DMSO (500 µL) and DMF (3.5 mL) was added triethylamine (7.18 µL, 51.5 µmol) followed by a solution of Preparation 12 (19.6 mg, 24.7 µmol) in DMF (500 µL). HATU (9.39 mg, 24.7 µL) was added and the reaction was stirred at room temperature for 1 hour.

Step 2

0.2M HCl (aq) was added dropwise to pH 3-4 and the reaction was allowed to stir at room temperature overnight. The reaction was concentrated in vacuo and purified using reverse phase column chromatography eluting with 5-40% MeCN in water with 0.1% ammonia to afford the title compound as a colourless solid (53.9 mg, 77%).

LCMS Method B: Rt=1.92 mins, ES$^-$ MS m/z 1709.70 [M−2H]$^-$/2, theoretical mass: 3421.4 Alternatively, Step 2 may be achieved by treating the residue from Step 1 with 0.5M AcOH to pH 4 and stirring at room temperature until completion.

Preparation 3

3',5,5'-Tris((22-((((2R,3R,4R,5S,6R)-3-acetamido-5-
(((2S,3R,4S,5S,6R)-3,5-di hydroxy-6-(hydroxym-
ethyl)-4-(((2R,3R,4S,5R,6R)-3,4,5-trihydroxy-6-
(hydroxymethyl)tetrahydro-2H-pyran-2-yl)oxy)
tetrahydro-2H-pyran-2-yl)oxy)-4-hydroxy-6-
(hydroxymethyl)tetrahydro-2H-pyran-2-yl)oxy)-2,
18-dioxo-6,9,12,15-tetraoxa-3,19-diazadocosyl)
oxy)-[1,1'-biphenyl]-3-carboxylic Acid

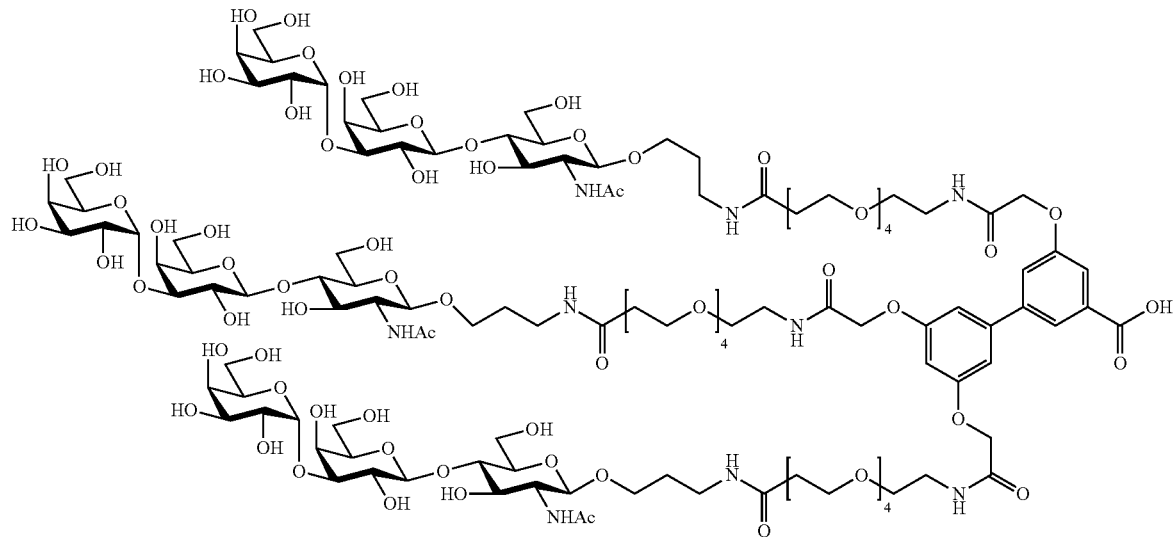

Step 1

To 1,1',1''-((5'-((benzyloxy)carbonyl)-[1,1'-biphenyl]-3,3',5-triyl)tris(oxy))tris(2-oxo-6,9,12,15-tetraoxa-3-azaoctadecan-18-oic acid) (Preparation 4, 48.0 mg, 38.3 µmol) in DMF (4 mL) was added TEA (48.1 µL, 345 µmol) followed by alpha-Gal (92.4 mg, 153 µmol) in DMSO (500 µL). HATU (58.3 mg, 153 µmol) was added and the reaction was left to stir for 1 hour under nitrogen at room temperature. The reaction was concentrated in vacuo and purified using reverse phase column chromatography eluting with 5-40% MeCN/water with 0.1% $NH_3$.

Step 2 Method 1

To the residue (94.0 mg, 31.3 µmol) dissolved in MeOH/water (1:1 v/v, 10 mL) was added Pd/C (10%, 10 mg). The reaction was put under an atmosphere of hydrogen (50 psi) and stirred for 3 hours at room temperature. The catalyst was removed by filtration through a syringe filter and the reaction was concentrated in vacuo to afford the title compound as a colourless solid (92 mg, 81% over two steps).

LCMS Method A: Rt=1.58 mins, ES⁻ MS m/z 1457.2 [M−2H]⁻/2, theoretical mass: 2915.9

Step 2 Method 2

Alternatively Step 2 may also be achieved by dissolving the residue from Step 1 in water (350 mg in 10 mL) and treating with triethylamine (10 mL) with vigorous stirring until reaction completion. Concentration in vacuo and purification using reverse phase column chromatography eluting with 5-40% MeCN in water with 0.1% ammonia affords the title compound (239 mg, 67%).

Preparation 4

1,1',1''-((5'-((Benzyloxy)carbonyl)-[1,1'-biphenyl]-3,3',5-triyl)tris(oxy))tris(2-oxo-6,9,12,15-tetraoxa-3-azaoctadecan-18-oic Acid)

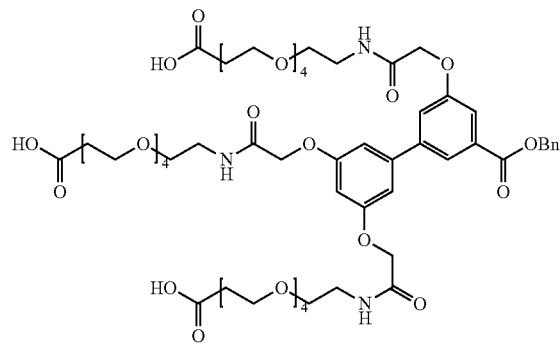

Step 1

To 2,2',2''-((5'-((benzyloxy)carbonyl)-[1,1'-biphenyl]-3,3',5-triyl)tris(oxy))triacetic acid (Preparation 5, 750 mg, 1.47 mmol) dissolved in DMF (30 mL) was added TEA (1.84 mL, 13.2 mmol) and tert-butyl 1-amino-3,6,9,12-tetraoxapentadecan-15-oate (1.89 g, 5.88 mmol). HATU (2.23 g, 5.88 mmol) was added and the reaction was stirred at room temperature under nitrogen for 2 hours. The reaction was concentrated in vacuo and the residue was purified using reverse phase column chromatography eluting with 20-80% MeCN/water with 0.1% $NH_3$.

Step 2

The residue was dissolved in DCM/TFA/water (10:10:1 v/v/v, 24 mL) and allowed to stir at room temperature for 2 hours. The reaction was concentrated in vacuo, azeotroped with dioxane/toluene (1:1 v/v, 3×24 mL) and purified using reverse phase column chromatography eluting with 5-40% MeCN/water with 0.1% formic acid to afford the title compound as a colourless gum (1.11 g, 60%).

LCMS Method A: Rt=2.36 mins, ES$^-$ MS m/z 1250.8 [M−H]$^-$ $^1$H NMR (400 MHz, DMSO-d$_6$): δ ppm 12.20 (3H, br s), 8.25 (1H, t), 8.15-8.10 (2H, m), 7.80 (1H, s), 7.55-7.45 (4H, m), 7.45-7.30 (3H, m), 6.90 (2H, d), 6.65-6.60 (1H, m), 5.40 (2H, s), 4.65 (2H, s), 4.55 (4H, s), 3.55 (6H, t), 3.50-3.40 (42H, m), 3.30-3.25 (6H, m), 2.40 (6H, t).

Preparation 5

2,2',2''-((5'-((Benzyloxy)carbonyl)-[1,1'-biphenyl]-3,3',5-triyl)tris(oxy))triacetic acid

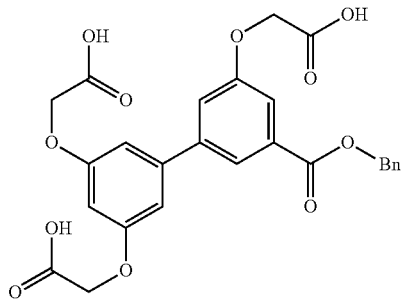 [SMILES: O=C(O)COc1cc(OCC(=O)O)cc(-c2cc(OCC(=O)O)cc(C(=O)OCc3ccccc3)c2)c1]

A solution of tri-tert-butyl 2,2',2''-((5'-((benzyloxy)carbonyl)-[1,1'-biphenyl]-3,3',5-triyl)tris(oxy))triacetate (Preparation 6, 100 mg, 147 µmol) dissolved in DCM/TFA/water (10:10:1 v/v/v, 5 mL) was stirred for 16 hours at room temperature. The reaction was concentrated in vacuo, dissolved in MeOH (1 mL) and precipitated with water (10 mL). The precipitate was collected by filtration, washed with water and dried under vacuum to afford the title compound as a colourless solid (57.8 mg, 77%).

LCMS Method A: Rt=2.48 mins, ES$^-$ MS m/z 509.3 [M−H]$^-$ $^1$H NMR (400 MHz, DMSO-d$_6$): δ ppm 13.05 (3H, br s), 7.90 (1H, s), 7.55-7.45 (3H, m), 7.45-7.30 (4H, m), 6.80 (2H, d), 6.50 (1H, t), 5.40 2H, s), 4.85 (2H, s). 4.75 (4H, s).

Preparation 6

Tri-tert-butyl 2,2',2''-((5'-((benzyloxy)carbonyl)-[1,1'-biphenyl]-3,3',5-triyl)tris(oxy))triacetate

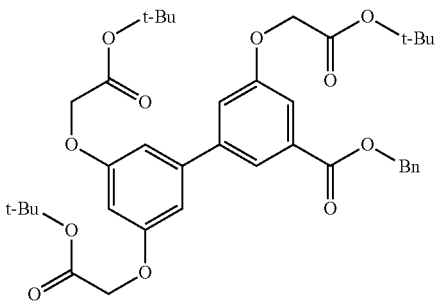 [SMILES: CC(C)(C)OC(=O)COc1cc(OCC(=O)OC(C)(C)C)cc(-c2cc(OCC(=O)OC(C)(C)C)cc(C(=O)OCc3ccccc3)c2)c1]

To benzyl 3',5,5'-trihydroxy-[1,1'-biphenyl]-3-carboxylate (Preparation 7, 356 mg, 1.06 mmol) dissolved in DMF (10 mL) was added tert-butyl bromoacetate (625 µL, 4.23 µmol) and potassium carbonate (1.17 g, 8.47 mmol). The resulting suspension was stirred for 16 hours under nitrogen before concentration in vacuo. The resulting residue was dissolved in water (10 mL) and extracted with EtOAc (2×10 mL). The combined organic layers were washed with brine (10 mL), 2M aqueous NaOH (10 mL), dried over MgSO$_4$ and concentrated in vacuo. The residue was purified using silica gel column chromatography eluting with 7-60% EtOAc/heptane to afford the title compound as a clear colourless gum (618 mg, 86%).

LCMS Method C: Rt=4.34 mins, no mass ion observed $^1$H NMR (400 MHz, CDCl$_3$): δ ppm 7.85 (1H, s), 7.55-7.50 (1H, m), 7.45-7.25 (6H, m), 6.70 (2H, d), 6.45-6.40 (1H, m), 5.35 (2H, s), 4.55 (2H, s), 4.50 (4H, s), 1.45 (27H, s)

Preparation 7

Benzyl 3',5,5'-trihydroxy-[1,1'-biphenyl]-3-carboxylate

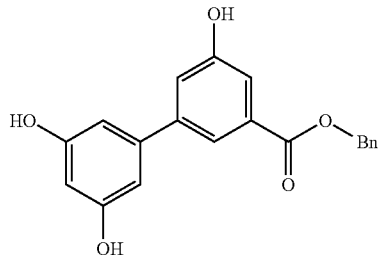 [SMILES: O=C(OCc1ccccc1)c1cc(O)cc(-c2cc(O)cc(O)c2)c1]

To a solution of crude benzyl 3',5'-bis((tert-butyldimethylsilyl)oxy)-5-hydroxy-[1,1'-biphenyl]-3-carboxylate (Preparation 8, 1.27 g, 2.46 mmol) dissolved in THF (12 mL) was added TBAF solution (1M in THF, 6.15 mL, 6.15 mmol) dropwise. The reaction was stirred at room temperature under nitrogen for 90 minutes before diluting with EtOAc (100 mL). The organic phase was washed with water (2×50 mL), dried over MgSO$_4$ and concentrated in vacuo. The residue was purified using silica gel column chromatography eluting with 5% MeOH in DCM to afford the title compound as a pale brown solid (356 mg, 43% over 3 steps).

LCMS Method A: Rt=2.66 mins, ES$^-$ MS m/z 335.3 [M−H]$^-$ $^1$H NMR (400 MHz, CD$_3$OD): δ ppm 7.60 (1H, t), 7.45-7.40 (2H, m), 7.40-20 (4H, m), 7.15-7.10 (1H, m), 6.45 (2H, d), 6.20 (1H, t), 5.30 (2H, s).

Preparation 8

Benzyl 3',5'-bis((tert-butyldimethylsilyl)oxy)-5-hydroxy-[1,1'-biphenyl]-3-carboxylate

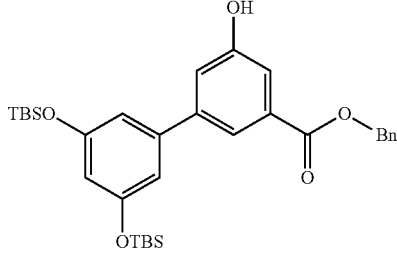 [SMILES: CC(C)(C)[Si](C)(C)Oc1cc(O[Si](C)(C)C(C)(C)C)cc(-c2cc(O)cc(C(=O)OCc3ccccc3)c2)c1]

A mixture of benzyl 3-bromo-5-hydroxybenzoate (Preparation 9, 755 mg, 2.46 mmol), sodium carbonate (912 mg, 8.60 mmol) and ((5-(4,4,5,5-tetramethyl-1,3,2-dioxaborolan-2-yl)-1,3-phenylene)bis(oxy))bis(tert-butyldimethylsilane) (Preparation 10, 1.87 g, 2.95 mmol) dissolved in dioxane/water (30 mL, 5:1 v/v) was degassed for 30 minutes with nitrogen. Pd(PPh$_3$)$_4$ (284 mg, 246 µmol) was added and the reaction heated to 100° C. for 90 minutes under nitrogen. After cooling to room temperature, EtOAc (100 mL) and water (50 mL) were added. The layers were separated and the aqueous phase was backwashed with EtOAc (2×25 mL). The combined organic phases were dried over MgSO$_4$ and concentrated in vacuo. The residue was treated with heptane (100 mL) and the resulting mixture sonicated for 5 minutes, before filtering to remove the solid. The filtrate was concentrated in vacuo to afford the crude title compound as a clear brown oil (1.27 g) that was used directly in the next step.

LCMS Method C: Rt=5.47 mins, ES$^+$ MS m/z 565.4 [M+H]$^+$

Preparation 9

Benzyl 3-bromo-5-hydroxybenzoate

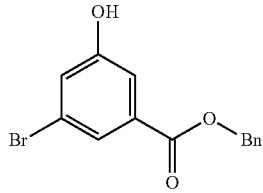 [SMILES: O=C(OCc1ccccc1)c1cc(O)cc(Br)c1]

To a solution of 3-bromo-5-hydroxybenzoic acid (4.08 g, 18.8 mmol) dissolved in DMF (25 mL) was added K$_2$CO$_3$ (2.60 g, 18.8 mmol). The suspension was stirred for 5 minutes before benzyl bromide (2.24 mL, 18.8 mmol) was added dropwise over 10 minutes. The reaction was stirred at room temperature under nitrogen for 16 hours overnight. Additional K$_2$CO$_3$ (520 mg, 3.76 mmol) and benzyl bromide (450 µL, 3.79 mmol) were added and the reaction stirred for 3 hours. The reaction was concentrated in vacuo and the residue was partitioned between EtOAc (30 mL) and water (30 mL). The aqueous layer was extracted with EtOAc (2×20 mL) and the combined organic layers washed with brine (30 mL). The organic layer was dried over MgSO$_4$ and concentrated in vacuo. The residue was purified by silica gel column chromatography eluting with 5% EtOAc in heptane to afford the title compound as a colourless solid (3.88 g, 67%).

LCMS Method A: Rt=3.36 mins, ES$^-$ MS m/z 307.2 [M−H]$^-$ $^1$H NMR (400 MHz, CDCl$_3$): δ ppm 7.75 (1H, t), 7.50-7.45 (1H, m), 7.45-7.30 (5H, m), 7.20 (1H, t), 5.30 (2H, s), 5.30 (1H, br s).

Preparation 10

((5-(4,4,5,5-Tetramethyl-1,3,2-dioxaborolan-2-yl)-1,3-phenylene)bis(oxy))bis(tert-butyldimethylsilane)

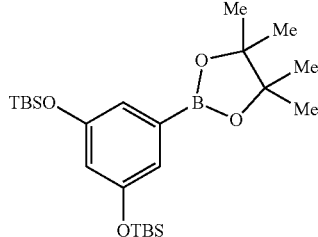 [SMILES: CC1(C)OB(c2cc(O[Si](C)(C)C(C)(C)C)cc(O[Si](C)(C)C(C)(C)C)c2)OC1(C)C]

A solution of 1,3-bis((tert-butyldimethylsilyl)oxy)benzene (Preparation 11, 1.00 g, 2.95 mmol and bis(pinacolato)diboron (750 mg, 2.95 mmol) dissolved in isohexane (15 mL) were degassed for 1 hour using nitrogen. [Ir(OMe)(COD)]$_2$ (19.6 mg, 59.1 µmol) and 4,4'-di-tert-butyl-2,2'-bipyridine (15.9 mg, 59.0 µmol) were added and the reaction sealed and heated to 110° C. for 16 hours. The reaction was cooled, concentrated in vacuo and used directly in the next step (1.87 g).

LCMS Method C: Rt=6.19 mins, ES$^+$ MS m/z 465.4 [M+H]$^+$ $^1$H NMR (400 MHz, CDCl$_3$): δ ppm 6.85 (2H, d), 6.40 (1H, t), 1.25 (12H, s), 0.95 (18H, s), 0.15 (12H, s).

Preparation 11

1,3-Bis((tert-butyldimethylsilyl)oxy)benzene

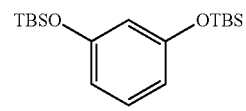 [SMILES: CC(C)(C)[Si](C)(C)Oc1cccc(O[Si](C)(C)C(C)(C)C)c1]

To resorcinol (2.00 g, 18.2 mmol) and imidazole (3.71 g, 54.5 mmol) dissolved in DCM (40 mL) was added tert-butyldimethylchlorosilane (8.21 g, 54.5 mmol). A precipitate formed and further DCM (40 mL) was added, before stirring for 16 hours at room temperature under nitrogen. The reaction was filtered and the filtrate was concentrated in vacuo. The residue was purified using silica gel column chromatography eluting with 0-10% EtOAc in heptanes to afford the title compound as a colourless oil (6.18 g, >100%).

LCMS Method C: Rt=5.39 mins, ES$^+$ MS m/z 339.3 [M+H]$^+$ $^1$H NMR (400 MHz, CDCl$_3$): δ ppm 6.95 (1H, t), 6.35 (2H, dd), 6.25 (1H, t), 1.85 (18H, s), 0.10 (12H, s).

Preparation 12

Benzyl 3'-(2-((2-aminoethyl)amino)-2-oxoethoxy)-5-(2-((2-(((4-methoxyphenyl)diphenylmethyl)amino) ethyl)amino)-2-oxoethoxy)-[1,1'-biphenyl]-3-carboxylate

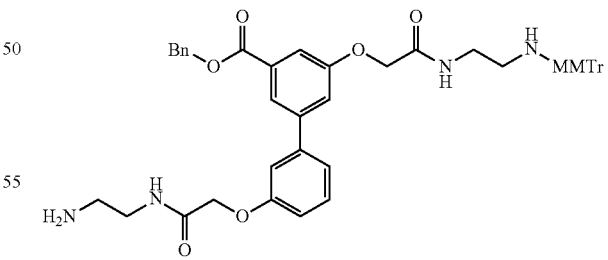

To a solution of benzyl 5-(2-((2-(((4-methoxyphenyl)diphenylmethyl)amino)ethyl) amino)-2-oxoethoxy)-3'-(2-oxo-2-((2-(2,2,2-trifluoroacetamido)ethyl)amino)ethoxy)-[1,1'-biphenyl]-3-carboxylate (Preparation 13, 230 mg, 0.259 mmol) in dioxane 3.0 mL) was added ammonium hydroxide (1.5 mL) and the reaction was stirred at room temperature for 18 hours. The reaction was concentrated in vacuo the residue purified using silica gel column chromatography eluting with 5-10% MeOH in DCM followed by 90:10:0.5 DCM:MeOH:NH$_4$OH to afford the title compound (135 mg, 66%).

LCMS Method B: Rt=3.57 mins, ES$^+$ MS m/z 793.2 [M+H]$^+$ $^1$H NMR (400 MHz, CDCl$_3$): δ ppm 7.89 (d, 1H), 7.63-7.53 (m, 2H), 7.47-7.20 (m, 21H), 7.20-7.10 (m, 4H), 6.83 (dd, 1H), 6.74 (dd, 2H), 5.33 (s, 2H), 4.62 (s, 2H), 4.45 (s, 2H), 3.72 (s, 3H), 3.59-3.48 (m, 2H), 3.47-3.38 (m, 2H), 3.08-2.99 (m, 2H), 2.49-2.30 (m, 2H).

Preparation 13

Benzyl 5-(2-((2-(((4-methoxyphenyl)diphenylmethyl)amino)ethyl)amino)-2-oxoethoxy)-3'-(2-oxo-2-((2-(2,2,2-trifluoroacetamido)ethyl)amino)ethoxy)-[1,1'-biphenyl]-3-carboxylate

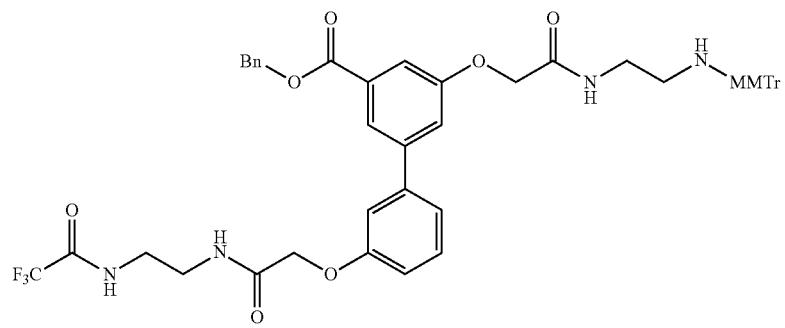

A suspension of benzyl 3-bromo-5-(2-((2-(((4-methoxyphenyl)diphenylmethyl) amino)ethyl)amino)-2-oxoethoxy)benzoate (Preparation 14, 515 mg, 0.758 mmol), bispinacolatodiboron (289 mg, 1.137 mmol) and potassium acetate (223 mg, 2.274 mmol) in dioxane (10 mL) was degassed with nitrogen, and Pd(dppf)Cl$_2$ (62 mg, 0.076 mmol) was added. The mixture was heated at 100° C. for 18 hours. To the cooled reaction mixture was added 2-(3-bromophenoxy)-N-[2-(2,2,2-trifluoroacetamido)ethyl]acetamide (Preparation 17, 280 mg, 0.758 mmol), 1M aq. sodium bicarbonate (2.3 mL) and Pd(dppf)Cl$_2$ (62 mg, 0.076 mmol). The mixture was heated to 100° C. for 18 hours under nitrogen before cooling to room temperature. The reaction mixture was diluted with EtOAc (100 mL) and washed with brine (100 mL). The organic layer was dried over magnesium sulphate and concentrated in vacuo. The residue was purified using silica gel column chromatography eluting with 50-75% EtOAc in heptanes to afford the title compound as a yellow oil (277 mg, 41%).

LCMS Method B: Rt=3.88 mins, ES$^+$ MS m/z 889.4 [M+H]$^+$ $^1$H NMR (400 MHz, CDCl$_3$): δ ppm 8.00-7.85 (m, 2H), 7.64 (d, 1H), 7.48-7.10 (m, 23H), 7.06 (d, 1H), 6.88 (dd, 1H), 6.78 (dd, 2H), 5.39 (s, 2H), 4.63 (s, 2H), 4.46 (s, 2H), 3.72 (s, 3H), 3.62-3.50 (m, 4H), 3.49-3.41 (m, 2H), 2.43-2.32 (m, 2H).

Preparation 14

Benzyl 3-bromo-5-(2-((2-(((4-methoxyphenyl)diphenylmethyl)amino)ethyl)amino)-2-oxoethoxy)benzoate

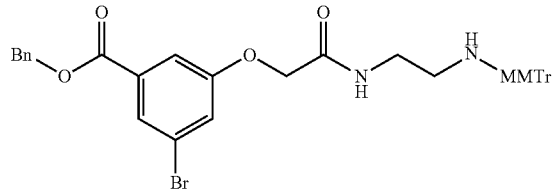

To a solution of 2-{3-[(benzyloxy)carbonyl]-5-bromophenoxy}acetic acid (Preparation 15, 1.658 g, 4.54 mmol) in DCM (16 mL) was added triethylamine (1.39 mL, 9.98 mmol) followed by a solution of N'-[(4-methoxyphenyl)diphenylmethyl]-1,2-ethanediamine (PCT 2013024052, 1.659 g, 4.99 mmol) in DCM (16 mL). To the mixture was added EDC.HCl (1.44 g, 7.49 mmol) and HOBt hydrate (1.01 g, 7.49 mmol). The reaction was stirred at room temperature for 18 hours. The reaction was diluted with DCM (20 mL) and washed with 10% aqueous potassium carbonate solution (50 mL) and brine (50 mL). The organic layer was dried over magnesium sulphate and concentrated in vacuo. The residue was purified using silica gel column chromatography eluting with 0-2% MeOH in DCM to afford the title compound as a yellow foam (2.13 g, 69%).

LCMS Method B: Rt=4.19 mins, ES$^+$ MS m/z 681.0 [M+H]$^+$ $^1$H NMR (400 MHz, CDCl$_3$): δ ppm 7.86 (s, 1H), 7.58 (s, 1H), 7.44-7.25 (m, 15H), 7.24-7.21 (m, 2H), 7.07-7.00 (m, 1H), 6.80 (d, 2H), 5.37 (s, 2H), 4.56 (s, 2H), 3.77 (s, 3H), 3.49-3.40 (m, 2H), 2.38 (t, 2H).

Preparation 15

2-{3-[(benzyloxy)carbonyl]-5-bromophenoxy}acetic acid

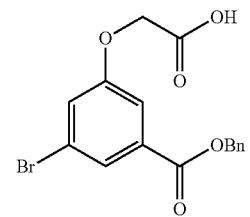 [SMILES: O=C(O)COc1cc(Br)cc(C(=O)OCc2ccccc2)c1]

To a solution of benzyl 3-bromo-5[2-(tertbutoxy)-2-oxo-ethoxy]benzoate (5.2 g, 12.3 mmol) in DCM (20 mL) was slowly added a mixture of TFA (20 mL) and water (2 mL). The solution was stirred at room temperature overnight before concentrating in vacuo. The residue was azeotroped with toluene to afford the title compound as a white solid (4.3 g, 95%).

LCMS Method B: Rt=3.16 mins, ES+ MS m/z 383.9 [M+NH4]+ and m/z 365.0 [M-H]-

$^1$H NMR (400 MHz, CDCl$_3$): δ ppm 7.88 (1H, d), 7.52 (1H, d), 7.45-7.31 (5H, m), 7.23 (1H, s), 5.35 (2H, s), 4.72 (2H, s).

Preparation 16

Benzyl 3-bromo-5[2-(tertbutoxy)-2-oxoethoxy]benzoate

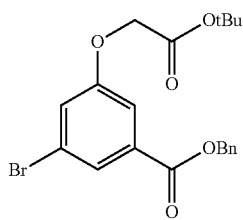 [SMILES: CC(C)(C)OC(=O)COc1cc(Br)cc(C(=O)OCc2ccccc2)c1]

To a solution of benzyl 3-bromo-5-hydroxybenzoate (Preparation 9, 10.4 g, 33.86 mmol) in anhydrous DMF (50 mL) was added potassium carbonate (5.62 g, 40.63 mmol) followed by tert-butylbromoacetate (7.41 g, 37.25 mmol). The suspension was stirred at room temperature for 48 hours. The reaction was quenched by the addition of water (50 mL) and extracted into EtOAc (2×100 mL). The combined organic extracts were washed with brine (thrice) concentrated in vacuo and purified using silica gel column chromatography eluting with 5-10% EtOAc in heptane to afford the title compound as an oil (14.30 g, >100%).

LCMS Method B: Rt=4.07 mins, ES+ MS m/z 439.9 [M+NH4]+

$^1$H NMR (400 MHz, CDCl$_3$): δ ppm 7.82 (s, 1H), 7.49 (s, 1H), 7.40 (m, 5H), 7.25 (s, 1H), 5.34 (s, 2H), 4.54 (s, 2H), 1.47 (s, 9H).

Preparation 17

2-(3-bromophenoxy)-N-[2-(2,2,2-trifluoroacetamido)ethyl]acetamide

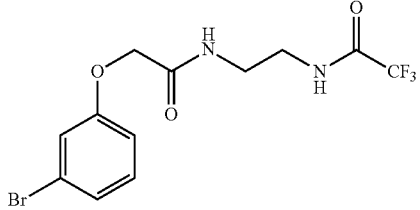 [SMILES: O=C(COc1cccc(Br)c1)NCCNC(=O)C(F)(F)F]

To a suspension of N-(2-aminoethyl)-2-(3-bromophenoxy)acetamide hydrochloride (Preparation 18, 4.72 g, 15.2 mmol) in MeOH (50 mL) was added a solution of triethylamine (6.17 g, 60.1 mmol) in MeOH (10 mL) and the mixture was stirred at room temperature for 20 minutes. To the resulting solution was added ethyl trifluoroacetate (4.33 g, 30.5 mmol) dropwise, with further stirring at room temperature for 3 hours. The reaction was concentrated in vacuo, and the solid residue was partitioned between 1:1 EtOAc:H$_2$O (150 mL). The organic extract was collected, dried over magnesium sulfate and concentrated in vacuo to afford the title compound as an off-white solid (5.0 g, 89%).

LCMS Method B: Rt=2.74 mins, ES+ MS m/z 370.9 [M+H]+ and 369.0 [M-H]-, Br isotopes observed.

$^1$H NMR (400 MHz, CDCl$_3$): δ ppm 7.60 (1H, br.s), 7.19-7.11 (2H, m), 7.24 (1H, d), 6.92 (1H, br.s), 6.82-6.76 (1H, m), 4.44 (2H, s), 3.58-3.48 (4H, m).

Preparation 18

N-(2-Aminoethyl)-2-(3-bromophenoxy)acetamide Hydrochloride

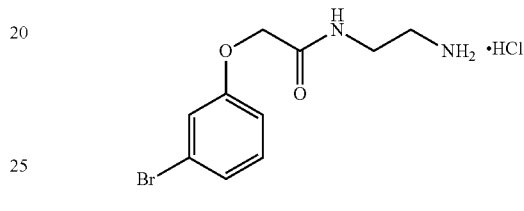

To a solution of tert-butyl N-{2-[2-(3-bromophenoxy)acetamido]ethyl}carbamate (Preparation 19, 17.4 g, 46.62 mmol) in dioxane (104 mL) was added 4M HCl in dioxane (70 mL) and the reaction was stirred at room temperature for 72 hours. TBME (250 mL) was added and the mixture stirred for a further 18 hours. The resulting white precipitate was filtered, washed with TBME (100 mL) and dried under vacuum to afford the title compound as the hydrochloride salt (12.6 g, 87%).

LCMS Method B: Rt=1.91 mins, ES+ MS m/z 273 [M+H]+

$^1$H NMR (400 MHz, CDCl$_3$): δ ppm 8.46-8.38 (m, 1H), 8.09 (br s, 3H), 7.33-7.20 (m, 2H), 7.19-7.14 (m, 1H), 7.08-6.99 (m, 1H), 4.52 (s, 2H), 3.44-3.32 (m, 2H), 2.97-2.81 (m, 2H).

Preparation 19

Tert-butyl N-{2-[2-(3-bromophenoxy)acetamido]ethyl}carbamate

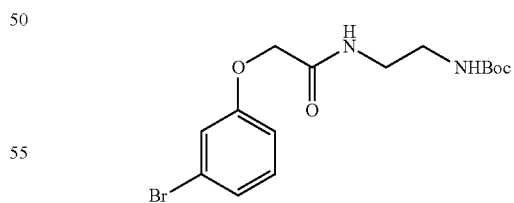

To a solution of 2-(3-bromophenoxy)acetic acid (Preparation 20, 13.4 g, 58 mmol) in DCM (200 mL) and triethylamine (16.2 mL, 116 mmol) was added a solution of Boc-ethylenediamine (10.22 g, 63.81 mmol) in DCM (68 mL) followed by EDC.HCl (16.68 g, 87 mmol) and HOBt (13.32 g, 87.02 mmol) and the reaction was stirred at room temperature for 18 hours. The mixture was washed with brine (150 mL), dried over MgSO$_4$ and concentrated in vacuo. The residue was purified using silica gel column chromatography eluting with 50% EtOAc in Heptanes to afford the title compound as a white solid (17.4 g, 80%).

LCMS Method A: Rt=2.63 mins, ES+ MS m/z 274.9 [M−Boc+H]+

$^1$H NMR (400 MHz, CDCl$_3$): δ ppm 7.39-7.30 (m, 1H), 7.22-7.12 (m, 3H), 6.92-6.83 (m, 1H), 4.88 (br s, 1H), 4.48 (s, 2H), 3.52-3.43 (m, 2H), 3.39-3.22 (m, 2H), 1.46 (s, 9H).

Preparation 20

2-(3-Bromophenoxy)acetic acid

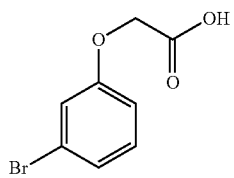 [SMILES: O=C(O)COc1cccc(Br)c1]

The title compound was prepared according to the method described for Preparation 15 using tert-butyl 2-(3-bromophenoxy)acetate (Preparation 21).

LCMS Method A: Rt=1.47 mins, ES+ MS m/z 231 [M+H]+

$^1$H NMR (400 MHz, CDCl$_3$): δ ppm 7.23-7.16 (m, 2H), 7.14-7.08 (m, 1H), 6.91-6.83 (m, 1H), 4.68 (s, 2H).

Preparation 21

Tert-butyl 2-(3-bromophenoxy)acetate

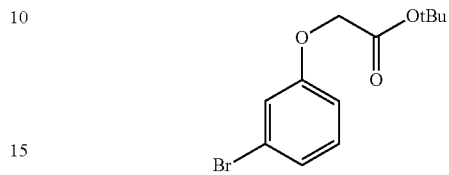

The title compound was prepared according to the method described for Preparation 16 using 3-bromophenol and tert-butylbromoacetate.

LCMS Method B: Rt=3.59 mins, no ionisation observed $^1$H NMR (400 MHz, CDCl$_3$): δ ppm 7.19-7.10 (m, 2H), 7.06 (d, 1H), 6.88-6.80 (m, 1H), 4.50 (s, 2H), 1.51 (s, 9H).

Preparation 22

Double Cluster 2

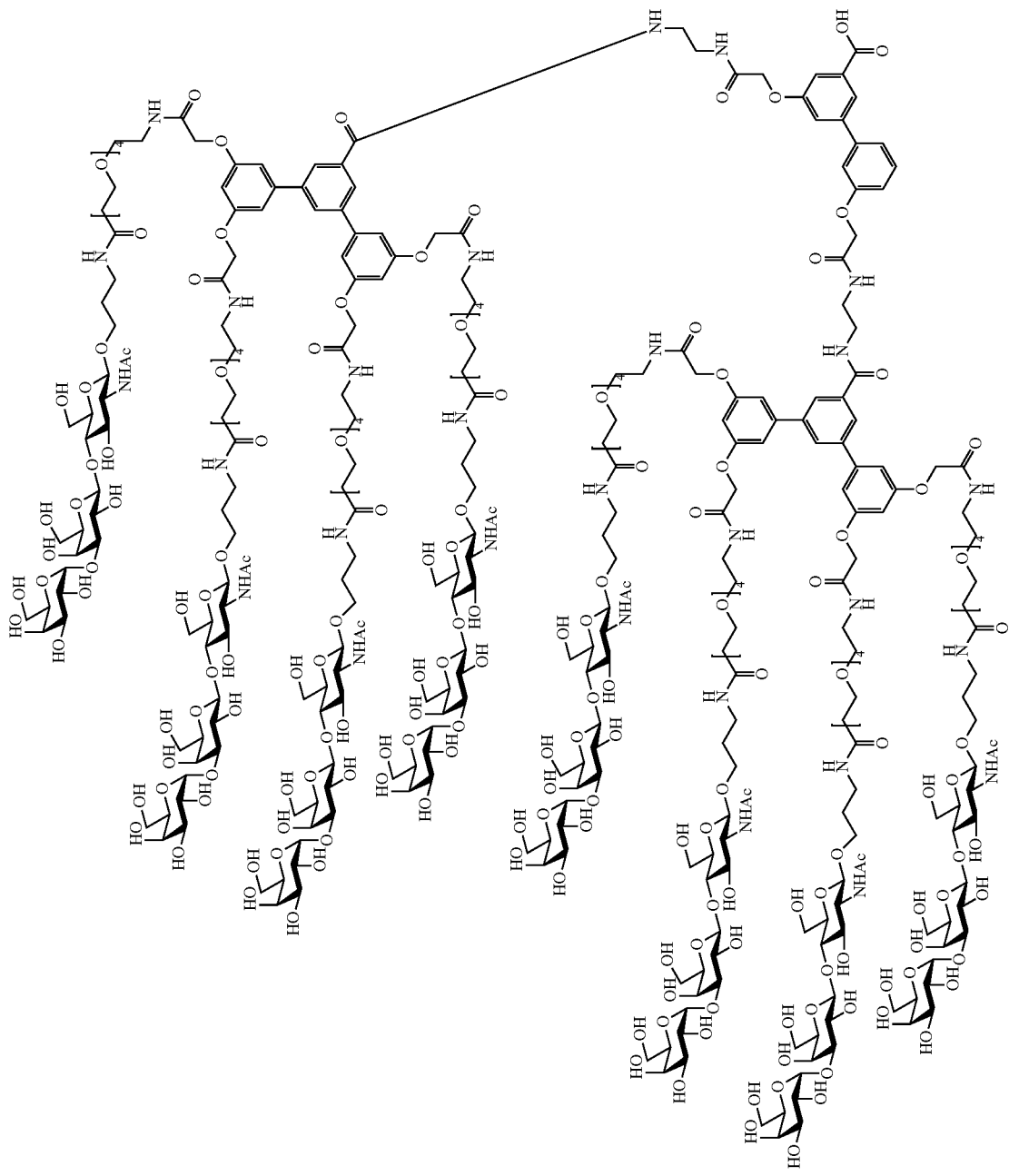

The title compound was prepared according to the method described for Preparation 1 using Preparation 23 and Preparation 24.

LCMS Method B: Rt=1.61 mins, ES$^+$ MS m/z 1640.7 [M+5H]$^+$/5, theoretical mass: 8190.2

Preparation 23

Precursor to Double Clusters 2 and 3

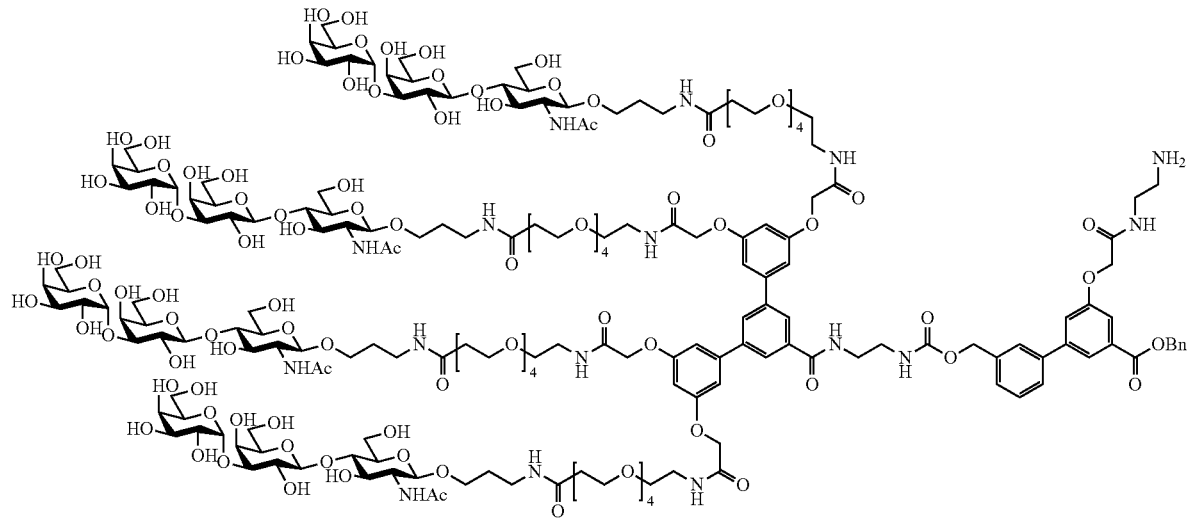

The title compound was prepared according to the method described for Preparation 2 using Preparation 12 and Preparation 24.

LCMS Method B: Rt=1.86 mins, ES$^+$ MS m/z 1468.0 [M+3H]$^+$/3, theoretical mass: 4400.4

Preparation 24

3,3″,5,5″-Tetrakis((22-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)-2,18-dioxo-6,9,12,15-tetraoxa-3,19-diazadocosyl)oxy)-[1,1′:3′,1″-terphenyl]-5′-carboxylic Acid

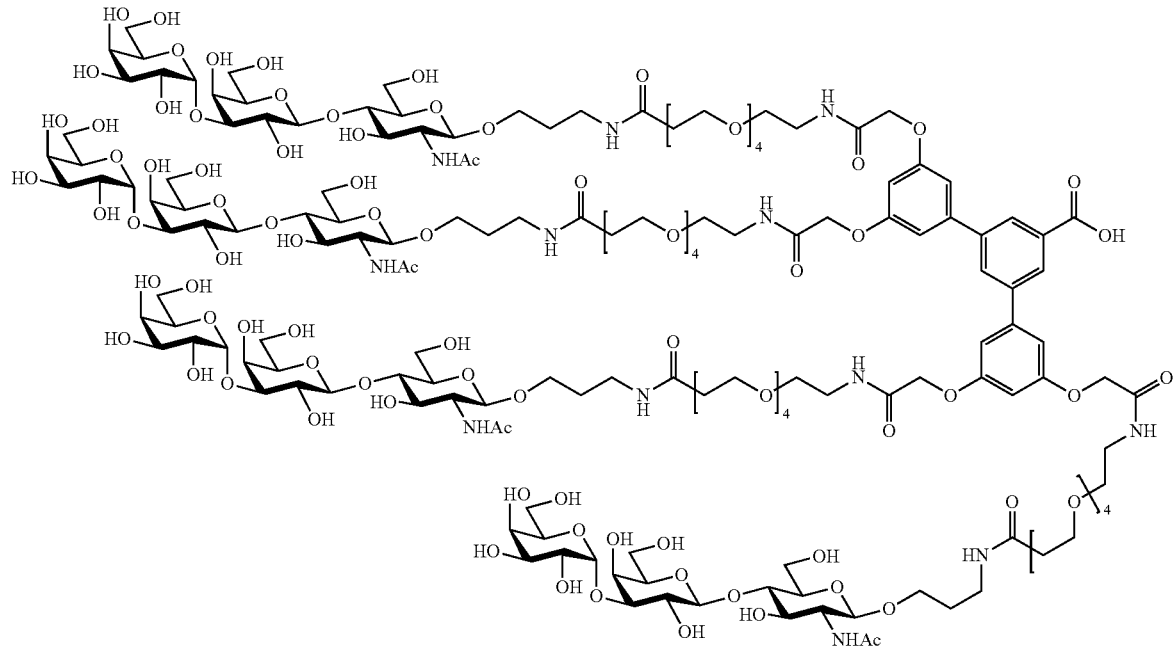

The title compound was prepared according to Preparation 3 using alpha Gal (6 eq), TEA (13 eq), HATU (6 eq) and Preparation 25. Deprotection with TEA/water.

Purification after Step 1: reverse phase preparative HPLC eluting with 7-60% MeCN in water with 0.1% NH$_3$ Purification after Step 2: reverse phase preparative HPLC eluting with 5-40% MeCN in water with 0.1% NH$_3$ LCMS Method B: Rt=1.41 mins, ES$^+$ MS m/z 1300.8 [M+3H]$^+$/3, theoretical mass: 3897.9

Preparation 25

1,1',1'',1'''-((5'-((Benzyloxy)carbonyl)-[1,1':3',1''-terphenyl]-3,3'',5,5''-tetrayl)tetrakis(oxy))tetrakis(2-oxo-6,9,12,15-tetraoxa-3-azaoctadecan-18-oic Acid)

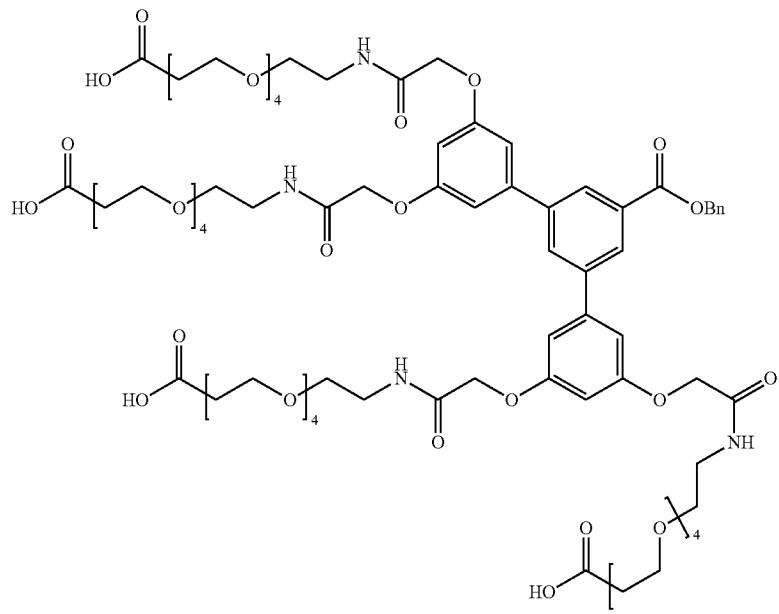

The title compound was prepared according to Preparation 4 using tert-butyl 1-amino-3,6,9,12-tetraoxapentadecan-15-oate (5 eq), TEA (11 eq), HATU (5 eq) and Preparation 26.

Purification after Step 1: reverse phase preparative HPLC eluting with 12-100% MeCN/water with 0.1% NH$_3$).

Purification after Step 2: reverse phase preparative HPLC eluting 12-100% MeCN/water with 0.1% NH$_3$).

LCMS Method A: Rt=2.39 mins, ES$^+$ MS m/z 1648.0 [M+H]$^+$

Preparation 26

2,2',2'',2'''-((5'-((Benzyloxy)carbonyl)-[1,1':3',1''-terphenyl]-3,3'',5,5''-tetrayl)tetrakis(oxy))tetraacetic acid

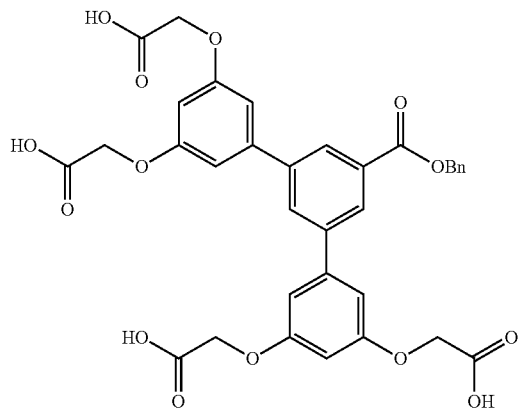 [SMILES: O=C(O)COc1cc(OCC(=O)O)cc(-c2cc(C(=O)OCc3ccccc3)cc(-c3cc(OCC(=O)O)cc(OCC(=O)O)c3)c2)c1]

The following Preparation was prepared according to the methods described by Preparation 6 followed by Preparation 5 using Preparation 27. The title compound was purified using reverse phase chromatography conditions eluting with 5-40% MeCN/water with 0.1% NH$_3$.

LCMS Method B: Rt=1.40 mins, ES$^-$ MS m/z 659.4 [M−H]$^-$ $^1$H NMR (400 MHz, DMSO-d$_6$): δ ppm 8.20 (2H, s), 8.00 (1H, s), 7.50-7.45 (2H, m), 7.40-7.35 (2H, m), 7.35-7.30 (1H, m), 6.75 (4H, s), 6.40 (2H, s), 5.40 (2H, s), 4.45 (8H, s).

Preparation 27

Benzyl 5-(3,5-dihydroxyphenyl)-3',5'-dihydroxy-[1,1'-biphenyl]-3-carboxylate

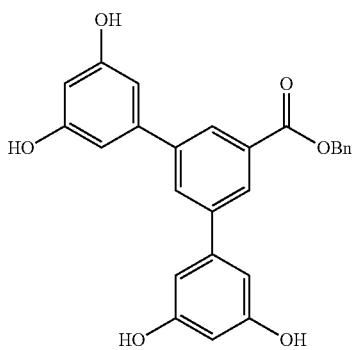 [SMILES: O=C(OCc1ccccc1)c1cc(-c2cc(O)cc(O)c2)cc(-c2cc(O)cc(O)c2)c1]

The title compound was prepared according to the methods described for Preparations 8 and 7 using 2,4-dibromobenzoic acid benzyl ester and ((5-(4,4,5,5-Tetramethyl-1,3,2-dioxaborolan-2-yl)-1,3-phenylene)bis(oxy))bis(tert-butyldimethylsilane) (Preparation 10).

LCMS Method B: Rt=2.73 minutes, ES$^-$ MS m/z 427.3 [M–H]$^-$ $^1$H NMR (400 MHz, DMSO-d$_6$): δ ppm 9.45 (4H, s), 8.02 (2H, s), 7.89 (1H, s), 5.53-5.38 (5H, m), 6.56 (4H, d), 6.28 (2H, s), 5.39 (2H, s).

Preparation 28

Double Cluster 3

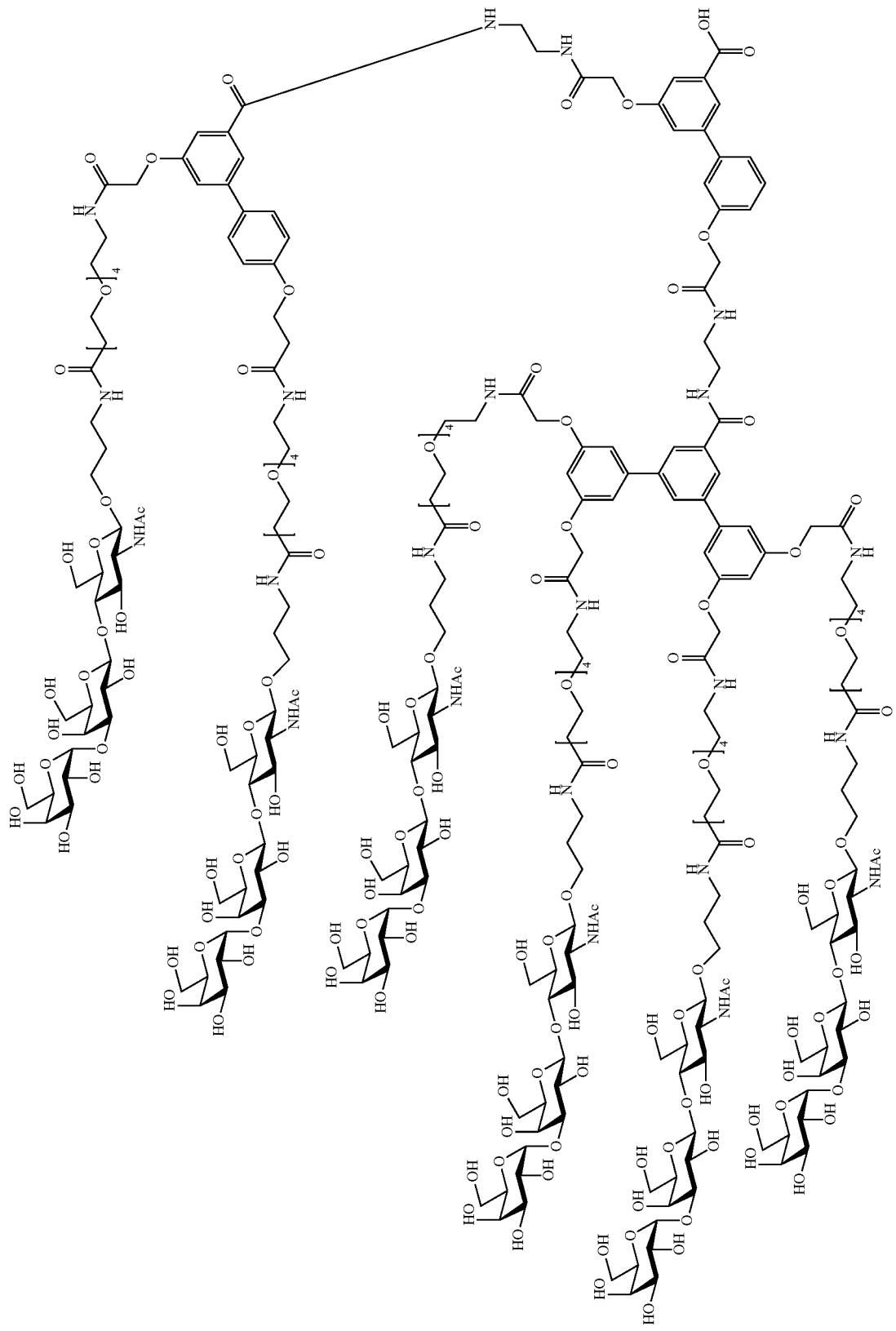

The title compound was prepared according to the method described for Preparation 1 using Preparation 23 and Preparation 29.

LCMS Method B: Rt=1.63 mins, ES+ MS m/z 1577.8 [M+4H]+/4, theoretical mass: 6302.3

Preparation 29

4',5-Bis((22-(((2R,3R,4R,5S,6R)-3-acetamido-5-(((2S,3R,4S,5S,6R)-3,5-di hydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)-2,18-dioxo-6,9,12,15-tetraoxa-3,19-diazadocosyl)oxy)-[1,1'-biphenyl]-3-carboxylic Acid

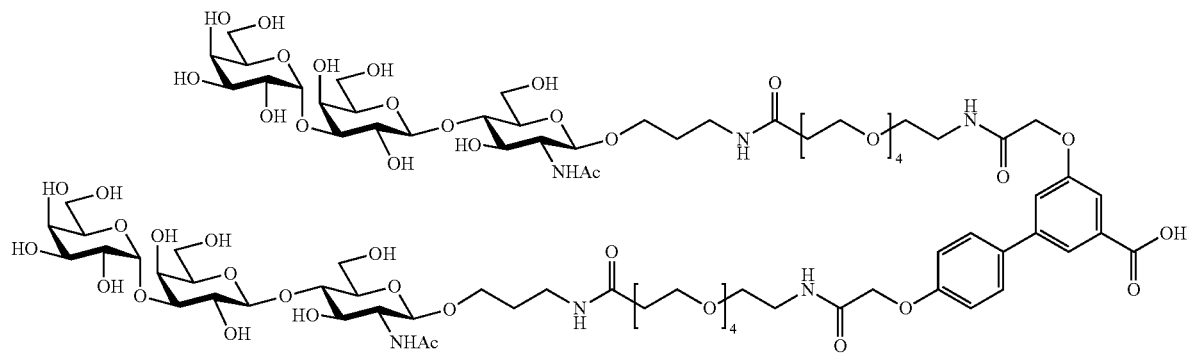

The title compound was prepared according to Preparation 3 using alpha Gal (2.5 eq), TEA (3.5 eq), HATU (2.6 eq) and 1,1'-((5-((benzyloxy)carbonyl)-[1,1'-biphenyl]-3,4'-diyl)bis(oxy))bis(2-oxo-6,9,12,15-tetraoxa-3-azaoctadecan-18-oic acid) (Preparation 30). The intermediate was deprotected according to Method 2.

Purification after Step 1: reverse phase HPLC eluting with 5-70% MeCN in water with 0.1% NH₃.

Purification after Step 2: reverse phase column chromatography eluting with 2-20% MeCN/water with 0.1% NH₃.

LCMS Method B: Rt=1.49 mins, ES+ MS m/z 1006.0 [M+2H]*/2, theoretical mass: 2010.0

Preparation 30

1,1'-((5-((Benzyloxy)carbonyl)-[1,1'-biphenyl]-3,4'-diyl)bis(oxy))bis(2-oxo-6,9,12,15-tetraoxa-3-azaoctadecan-18-oic Acid)

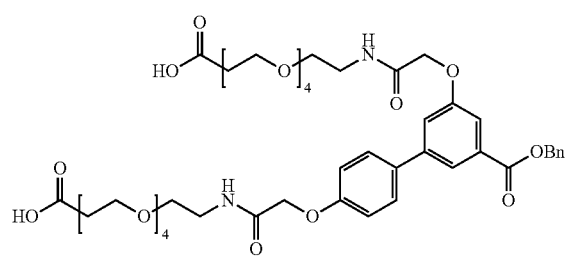

The title compound was prepared according to Preparation 4 using tert-butyl 1-amino-3,6,9,12-tetraoxapentadecan-15-oate (2.5 eq), TEA (6 eq), HATU (2.5 eq) and Preparation 31.

Purification after Step 1: reverse phase preparative HPLC eluting with from between 20-70% MeCN/water with 0.1% NH₃

Purification after Step 2: reverse phase preparative HPLC eluting with from between 0-60% MeCN/water with 0.1% formic acid.

LCMS Method A: Rt=2.32 mins, ES+ MS m/z 931.6 [M+H]+

¹H NMR (400 MHz, DMSO-d₆): δ ppm 12.17 (2H, br s), 8.18 (1H, t), 8.10 (1H, t), 7.78-7.75 (1H, m), 7.64 (2H, d), 7.47-7.46 (4H, m), 7.42-4.32 (3H, m), 7.05 (d, 2H), 5.37 (s, 2H), 4.63 (2H, s), 4.52 (2H, s), 3.57-3.55 (4H, m), 3.49-3.43 (28H, m), 3.30-3.27 (4H, m), 2.41-2.39 (4H, m).

Preparation 31

2,2'-((5-((Benzyloxy)carbonyl)-[1,1'-biphenyl]-3,4'-diyl)bis(oxy))diacetic acid

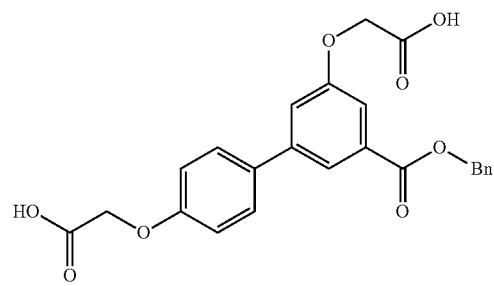 [SMILES: O=C(O)COc1ccc(-c2cc(OCC(=O)O)cc(C(=O)OCc3ccccc3)c2)cc1]

A solution of di-tert-butyl 2,2'-((5-((benzyloxy)carbonyl)-[1,1'-biphenyl]-3,4'-diyl)bis(oxy))diacetate (Preparation 32, 200 mg, 365 μmol) dissolved in DCM/TFA/water (10:10:1 v/v/v, 10 mL) was stirred for 3 hours at room temperature. The reaction was concentrated in vacuo and azeotroped with dioxane/toluene (1:1, v/v, 2×10 mL) before freeze-drying overnight to afford the title compound as a colourless solid (101 mg, 64%).

LCMS Method A: Rt=1.83 mins, ES⁻ MS m/z 435.3 [M−H]⁻

¹H NMR (400 MHz, CD₃OD): δ ppm 7.90 (1H, t), 7.65-7.55 (2H, m), 7.55-7.50 (1H, m), 7.50-7.45 (2H, m) 7.45-7.35 (4H, m), 7.10-7.00 (2H, m), 5.40 (2H, s), 4.80 (2H, s), 4.70 (2H, s).

Preparation 32

Di-tert-butyl 2,2'-((5-((benzyloxy)carbonyl)-[1,1'-biphenyl]-3,4'-diyl)bis(oxy))diacetate

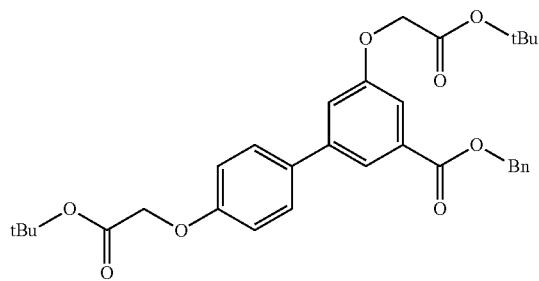 [SMILES: CC(C)(C)OC(=O)COc1ccc(-c2cc(OCC(=O)OC(C)(C)C)cc(C(=O)OCc3ccccc3)c2)cc1]

To benzyl 4',5-dihydroxy-[1,1'-biphenyl]-3-carboxylate (Preparation 33, 815 mg, 2.54 mmol) dissolved in DMF (10 mL) was added tert butyl bromoacetate (752 µL, 5.09 µmol) and potassium carbonate (1.58 g, 11.5 mmol). The resulting suspension was stirred for 5 hours at room temperature under nitrogen. The reaction was concentrated in vacuo and the resulting residue was dissolved in water (30 mL) and extracted with EtOAc (2×30 mL). The combined organic layers were washed with brine (30 mL), 2M aqueous NaOH (30 mL), dried over MgSO$_4$ and concentrated in vacuo to afford the title compound as a yellow oil that solidified over time (1.49 g, >99%) and was used directly in the next step.

LCMS Method C: Rt=4.23 mins, no mass ion observed.
$^1$H NMR (400 MHz, CD$_3$OD): δ ppm 7.85 (1H, t), 7.60-7.55 (2H, m), 7.50-7.35 (7H, m), 7.05-6.95 (2H, m), 5.40 (2H, s), 4.70 (2H, s), 4.65 (2H, s), 1.50 (9H, s), 1.45 (9H, s).

Preparation 33

Benzyl 4',5-dihydroxy-[1,1'-biphenyl]-3-carboxylate

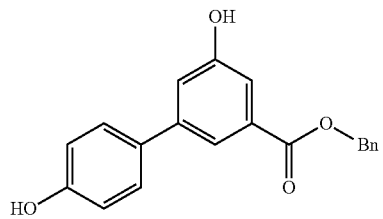 [SMILES: O=C(OCc1ccccc1)c1cc(O)cc(-c2ccc(O)cc2)c1]

A mixture of benzyl 3-bromo-5-hydroxybenzoate (Preparation 9, 1.05 g, 3.42 mmol), sodium carbonate (1.27 g, 12.0 mmol) and (4-hydroxyphenyl)boronic acid (565 mg, 4.10 mmol) dissolved in dioxane/water (3:1 v/v, 30 mL) were deoxygenated for 30 minutes with nitrogen. Pd(PPh$_3$)$_4$ (395 mg, 341 µmol) was added and the reaction was heated to 100° C. for 5 hours under nitrogen. After cooling to room temperature, EtOAc (50 mL) and water (30 mL) were added and the layers were separated. The aqueous layer was extracted with EtOAc (2×50 mL) and the combined organic layers washed with brine (50 mL). The organic layer was dried over MgSO$_4$ and concentrated in vacuo. The residue was purified using silica gel column chromatography eluting with 5-40% EtOAc in heptanes to afford the title compound as a yellow solid (815 mg, 74%).

LCMS Method A: Rt=2.94 mins, ES$^+$ MS m/z 319.3 [M−H]$^−$
$^1$H NMR (400 MHz, CD$_3$OD): δ ppm 7.70 (1H, t), 7.50-7.35 (8H, m), 7.20 (1H, t), 6.85-6.80 (2H, m), 5.35 (2H, s).

Preparation 34

Double Cluster 4

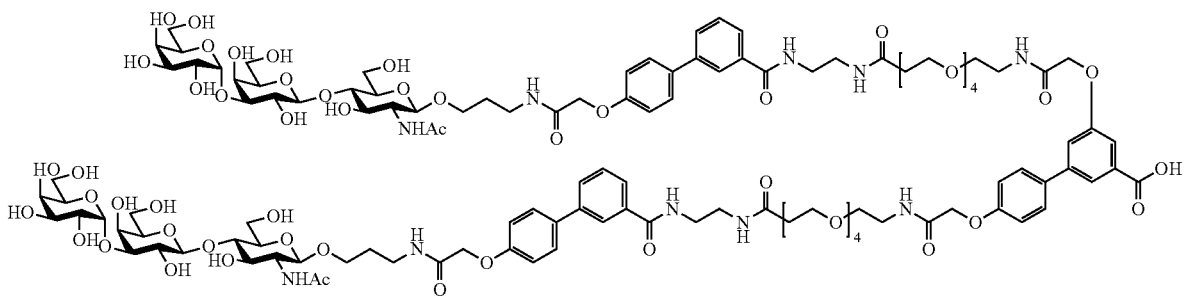

Benzyl 4',5-bis((1-(4'-(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-yl)-1,6,22-trioxo-9,12,15,18-tetraoxa-2,5,21-triazatricosan-23-yl)oxy)-[1,1'-biphenyl]-3-carboxylate (Preparation 35, 9.06 mg, 3.36 µmol) was dissolved in MeOH/water (2 mL, 1:1, v/v) and hydrogenated over palladium on carbon (1 mg) at 50 psi for 3 hours at room temperature. The reaction was filtered and stirred with DMT resin (10 mg) for 30 minutes in MeOH/water (2 mL, 1:1, v/v). The reaction was filtered and concentrated in vacuo to afford the title compound as a colourless solid (5.00 mg, 57%).

LCMS Method A: Rt=1.88 mins, ES$^−$ MS m/z 1300.2 [M−H]$^−$, theoretical mass: 2602.7

Preparation 35

Benzyl 4',5-bis((1-(4'-(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-yl)-1,6,22-trioxo-9,12,15,18-tetraoxa-2,5,21-triazatricosan-23-yl)oxy)-[1,1'-biphenyl]-3-carboxylate

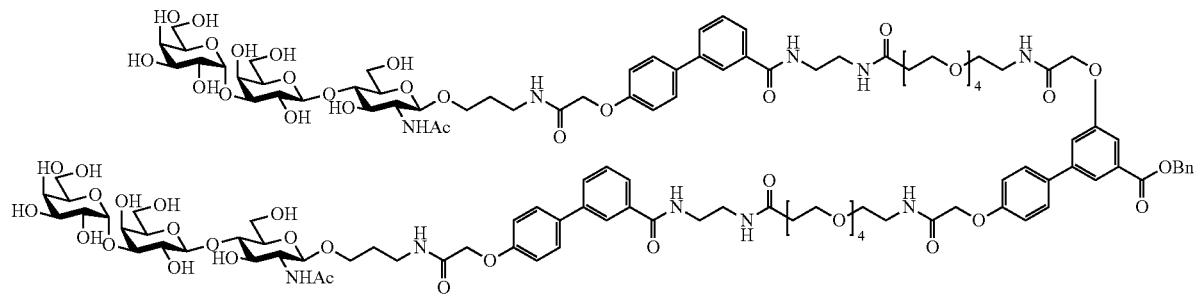

To benzyl 4',5-bis((21-amino-2,18-dioxo-6,9,12,15-tetraoxa-3,19-diazahenicosyl)oxy)-[1,1'-biphenyl]-3-carboxylate (Preparation 36, 15.0 mg, 14.8 μmol), 4'-(2-((3-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylic acid (Preparation 38, 25.7 mg, 30.0 μmol) and TEA (12.5 μL, 88.8 μmol) dissolved in DMF (400 μL) was added HATU (16.7 mg, 44.4 μmol). The mixture was stirred at room temperature for 50 hours and concentrated in vacuo. The residue was purified using reverse phase column chromatography eluting with 7-60% MeCN/water with 0.1% $NH_3$ to afford the title compound as a colourless oil (9.06 mg, 23%). LCMS Method B: Rt=2.19 mins, ES$^+$ MS m/z 1347.3 [M+2H]$^+$/2, theoretical mass: 2692.8

Preparation 36

Benzyl 4',5-bis((21-amino-2,18-dioxo-6,9,12,15-tetraoxa-3,19-diazahenicosyl)oxy)-[1,1'-biphenyl]-3-carboxylate

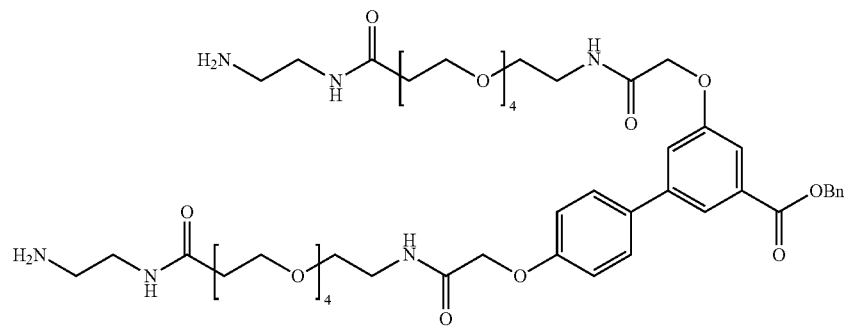

To benzyl 4',5-bis((2,2-dimethyl-4,9,25-trioxo-3,12,15,18,21-pentaoxa-5,8,24-triazahexacosan-26-yl)oxy)-[1,1'-biphenyl]-3-carboxylate (Preparation 37, 620 mg, 0.511 mmol) dissolved in dioxane (3.0 mL) was added 4M HCl in dioxane (1.28 mL, 5.11 mmol). The reaction mixture was stirred at room temperature for 2 hours and the solvent removed under reduced pressure. The resulting oil was purified using reverse phase column chromatography eluting with 7-60% MeCN/water with 0.1% NH₃ to afford the title compound as a colourless oil (332 mg, 64%).

LCMS Method B: Rt=2.18 mins, ES⁺ MS m/z 1015.6 [M+H]⁺

Preparation 37

Benzyl 4',5-bis((2,2-dimethyl-4,9,25-trioxo-3,12,15,18,21-pentaoxa-5,8,24-triazahexacosan-26-yl)oxy)-[1,1'-biphenyl]-3-carboxylate

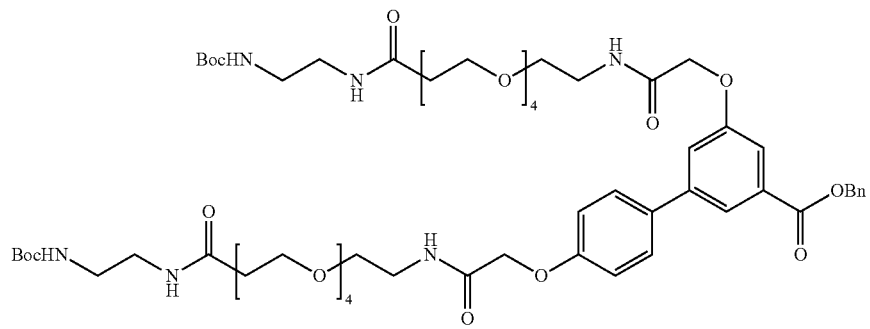

To 1,1'-((5-(((benzyloxy)carbonyl)-[1,1'-biphenyl]-3,4'-diyl)bis(oxy))bis(2-oxo-6,9,12,15-tetraoxa-3-azaoctadecan-18-oic acid) (Preparation 30, 500 mg, 0.538 mmol) dissolved in DMF (5.0 mL) was added tert-butyl (2-aminoethyl)carbamate (207 mg, 1.291 mmol), TEA (450 µL, 3.228 mmol) and HATU (491 mg, 1.291 mmol). The mixture was stirred at room temperature for 18 hours before the addition of water (40 mL). The mixture was extracted with EtOAc (4×30 mL) and the combined extracts were washed with 1M HCl (40 mL), saturated aqueous NaHCO₃ (50 mL), brine (3×50 mL), dried over magnesium sulphate and concentrated in vacuo. The residue was purified using silica gel column chromatography eluting with 5-10% MeOH in DCM to afford the title compound (620 mg, 95%).

LCMS Method B: Rt=2.85 mins, ES⁺ MS m/z 1215.8 [M+H]⁺

¹H NMR (400 MHz, CDCl₃): δ ppm 7.94 (1H, s), 7.60-7.57 (3H, m), 7.49-7.37 (5H, m), 7.26-7.18 (1H, m), 7.02 (2H, d), 6.92-6.83 (2H, m), 5.40 (2H, s), 5.22 (2H, br s), 4.61 (2H, s), 4.59 (2H, s), 3.73-3.66 (4H, m), 3.64-3.57 (30H, m), 3.37-3.29 (4H, m), 3.28-3.20 (4H, m), 2.48-2.42 (4H, m), 1.43 (18H, s).

Preparation 38

4'-(2-((3-(((2R,3R,4R,5S,6R)-3-Acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)propyl)amino)-2-oxoethoxy)-[1,1'-biphenyl]-3-carboxylic Acid

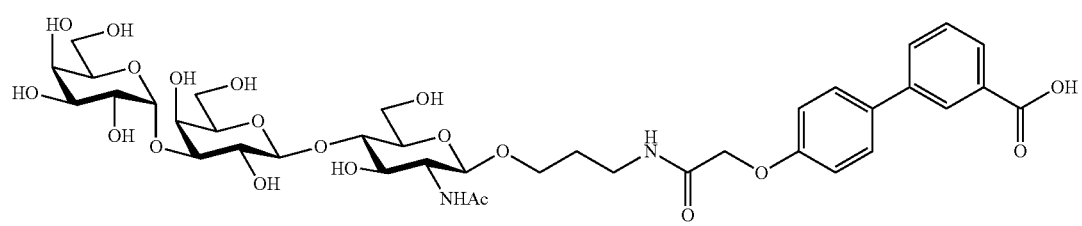

The title compound was prepared according to the method described for Preparation 3 using 1.3 eq alpha-Gal, 3 eq TEA, 1.5 eq HATU and 2-((3'-((Benzyloxy)carbonyl)-[1,1'-biphenyl]-4-yl)oxy)acetic acid (Preparation 39) followed by Step 2 Method 1.

Isolated yield: 55% over 2 steps, purification using preparative HPLC eluting with 7-60% MeCN in water with 0.1% NH$_3$ and following hydrogenation, the residue was purified using reverse phase column chromatography eluting with 5-40% MeCN/water with 0.1% NH$_3$.

LCMS Method A: Rt=1.83 mins, ES$^+$ MS m/z 857.6 [M+H]$^+$

Preparation 39

2-((3'-((Benzyloxy)carbonyl)-[1,1'-biphenyl]-4-yl)oxy)acetic acid

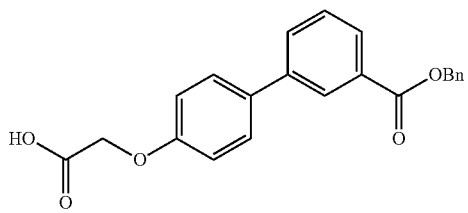 [SMILES: O=C(O)COc1ccc(-c2cccc(C(=O)OCc3ccccc3)c2)cc1]

The title compound was prepared according to the method described for Preparation 31 using benzyl 4'-(2-(tert-butoxy)-2-oxoethoxy)-[1,1'-biphenyl]-3-carboxylate (Preparation 40).

LCMS Method B: Rt=2.43 mins, ES$^+$ MS m/z 363.2 [M+H]$^+$ $^1$H NMR (400 MHz, DMSO-d$_6$): δ ppm 13.00 (1H, s), 8.15 (1H, t), 7.90-7.85 (2H, m), 7.65-55 (3H, m), 7.50-7.45 (2H, m), 7.45-7.30 (3H, m) 7.00-6.95 (2H, m), 5.40 (2H, s), 4.70 (2H, s).

Preparation 40

Benzyl 4'-(2-(tert-butoxy)-2-oxoethoxy)-[1,1'-biphenyl]-3-carboxylate

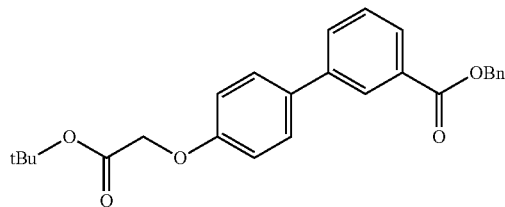 [SMILES: CC(C)(C)OC(=O)COc1ccc(-c2cccc(C(=O)OCc3ccccc3)c2)cc1]

To a solution of benzyl 4'-hydroxy-[1,1'-biphenyl]-3-carboxylate (Preparation 41, 368 mg, 1.21 mmol) and tert-butyl bromoacetate (178 μL, 1.21 mmol) in DMF (5 mL) was added potassium carbonate (200 mg, 1.45 mmol) and the reaction was stirred at room temperature for 20 hours followed by 50° C. for 2 hours. The reaction was concentrated in vacuo and the resulting residue partitioned between water (20 mL) and DCM (20 mL). The organic layer was separated and the aqueous layer extracted again with DCM (20 mL). The combined organic extracts were washed with water (10 mL), dried over sodium sulphate and concentrated in vacuo. The residue was purified by silica gel column chromatography eluting with 0-15% EtOAc in hexane to afford the title compound as an oil (510 mg, 100%).

LCMS Method D: Rt=3.85 mins, no mass ion observed $^1$H NMR (400 MHz, CDCl$_3$): δ ppm 8.25 (1H, t), 8.03-7.99 (1H, dt), 7.76-7.71 (1H, m), 7.58-7.31 (8H, m), 7.06-6.95 (2H, m), 5.39 (2H, s), 4.56 (2H, s), 1.50 (9H, s).

Preparation 41

Benzyl 4'-hydroxy-[1,1'-biphenyl]-3-carboxylate

To a solution of benzyl chloride (295 μL, 2.56 mmol) in DMF (5 mL) was added 4'-hydroxybiphenyl-3-carboxylic acid (500 mg, 2.33 mmol) and potassium carbonate (322 mg, 2.33 mmol). The reaction mixture was stirred at room temperature for 20 hours before concentrating in vacuo. The residue was partitioned between water (20 mL) and diethyl ether (20 mL). The organic layer was separated and the aqueous layer extracted again with diethyl ether (20 mL). The combined organic extracts were washed with water (10 mL), dried over sodium sulfate and concentrated in vacuo. The residue was purified by silica gel column chromatography eluting with 0-30% EtOAc in hexane to afford the title compound as a white solid (378 mg, 53%).

LCMS Method D: Rt=3.48 mins, ES$^+$ MS m/z 305.0 [M+H]$^+$ $^1$H NMR (400 MHz, CDCl$_3$): δ ppm 8.26-8.24 (1H, m), 8.03-7.98 (1H, m), 7.75-7.71 (1H, m), 7.51-7.43 (5H, m), 7.42-7.31 (3H, m), 6.95-6.90 (2H, m), 5.40 (2H, s).

Preparation 42

Double Cluster 5

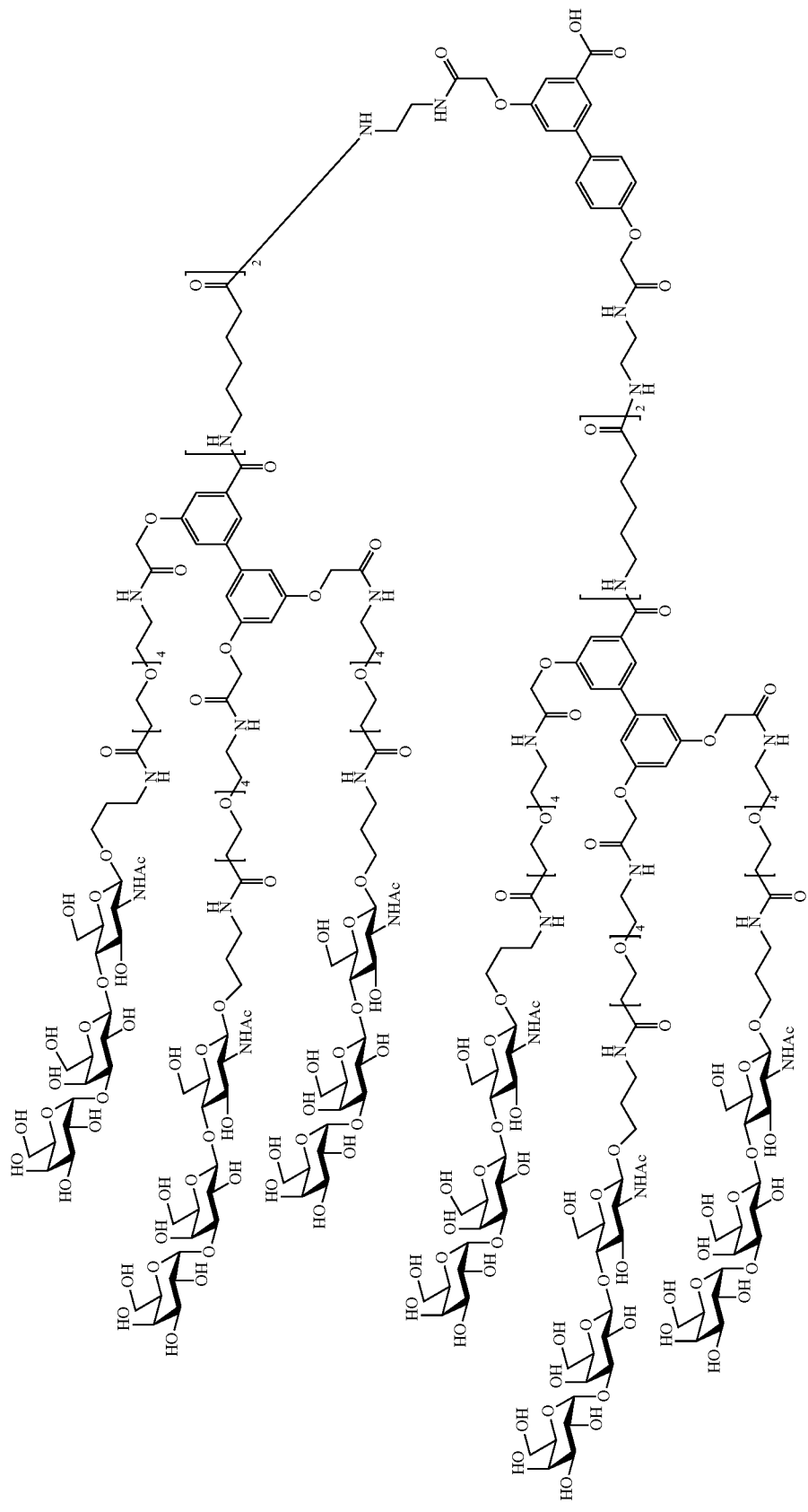

Step 1

To a solution of 6-(6-(3',5,5'-tris((22-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)-2,18-dioxo-6,9,12,15-tetraoxa-3,19-diazadocosyl)oxy)-[1,1'-biphenyl]-3-carboxamido)hexanamido)hexanoic acid (Preparation 44, 5 mg, 3.4 μmol) in a mixture of DMSO (250 μL) and DMF (250 μL) was added triethylamine (1.6 μL, 11.7 μmol) followed by a solution of benzyl 5-(2-((2-aminoethyl)amino)-2-oxoethoxy)-4'-((1,8,15,20-tetraoxo-1-(3',5,5'-tris((22-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)-2,18-dioxo-6,9,12,15-tetraoxa-3,19-diazadocosyl)oxy)-[1,1'-biphenyl]-3-yl)-2,9,16,19-tetraazahenicosan-21-yl)oxy)-[1,1'-biphenyl]-3-carboxylate (Preparation 43, 12.2 mg, 3.4 μmol) in DMSO (500 μL). HATU (1.5 mg, 4.0 μmol) was added and the reaction was stirred at room temperature for 18 hours. The reaction was concentrated in vacuo and purified using reverse phase column chromatography eluting with 5-40% MeCN in water with 0.1% ammonia to afford the benzyl intermediate residue.

LCMS Rt=1.86 minutes, ES$^+$ MS m/z 1691.4 [M+4H]$^+$/4, theoretical mass: 6769.0

Step 2

The residue from Step 1 was dissolved in water (1.0 mL) and treated with triethylamine (1.0 mL). The biphasic mixture was stirred at room temperature for overnight before concentrating to low volume (0.5 mL). The residue was purified using reverse phase column chromatography eluting with 5-40% MeCN in water with 0.1% ammonia to afford the title compound as a colourless solid (11 mg, 49% over 2 steps).

LCMS Rt=1.62 minutes, ES$^+$ MS m/z 1671.0 [M+4H]$^+$/4, theoretical mass: 6678.9

Preparation 43

Precursor to Double Cluster 5

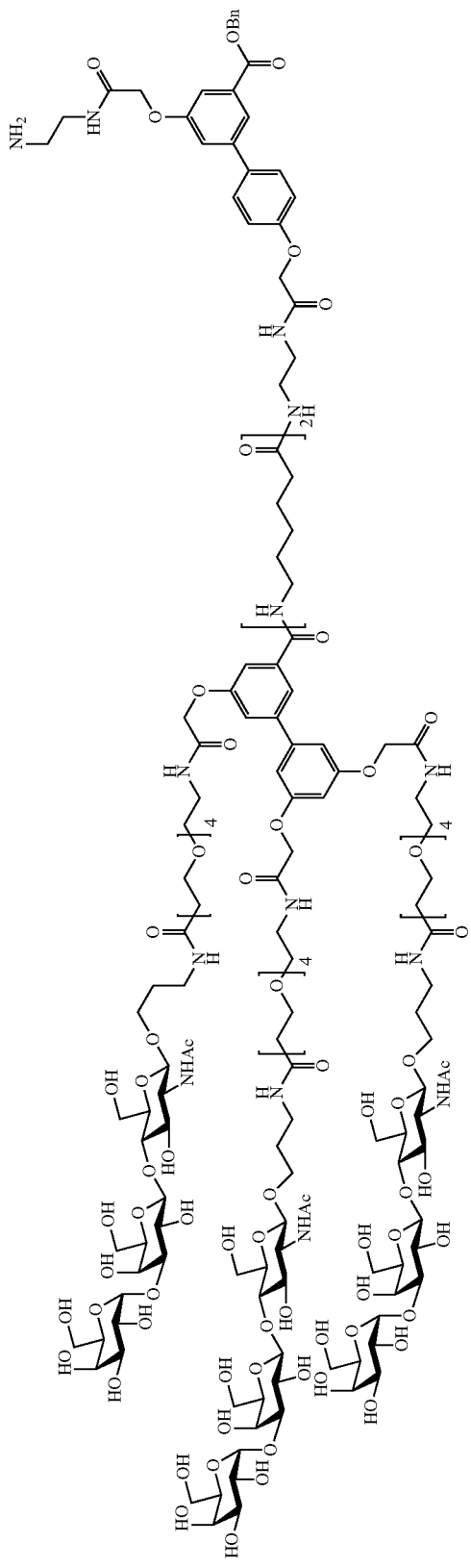

Step 1

To a solution of 6-(6-(3',5,5'-tris((22-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)-2,18-dioxo-6,9,12,15-tetraoxa-3,19-diazadocosyl)oxy)-[1,1'-biphenyl]-3-carboxamido)hexanamido)hexanoic acid (Preparation 44, 10.3 mg, 3.3 µmol) in a mixture of DMSO (500 µL) and DMF (500 µL) was added triethylamine (3.4 µL, 24.5 µmol) followed by a solution of benzyl 4'-(2-((2-aminoethyl)amino)-2-oxoethoxy)-5-(2-((2-(((4-methoxyphenyl)diphenylmethyl)amino)ethyl)amino)-2-oxoethoxy)-[1,1'-biphenyl]-3-carboxylate (Preparation 45, 6.7 mg, 8.4 µmol) in DMF (200 µL). HATU (3.2 mg, 8.4 µmol) was added and the reaction was stirred at room temperature overnight.

The above reaction was repeated with 8.7 mg of 6-(6-(3',5,5'-tris((22-(((2R,3R,4R,5S,6R)-acetamid-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)-2,18-dioxo-6,9,12,15-tetraoxa-3,19-diazadocosyl)oxy)-[1,1'-biphenyl]-3-carboxamido)hexanamido)hexanoic acid (Preparation B).

Step 2

0.2M HCl (aq) was added dropwise to pH 3-4 and the reactions were stirred at room temperature overnight. The reactions were concentrated in vacuo, combined and purified using reverse phase column chromatography eluting with 7-60% MeCN in water to afford the title compound as a colourless solid (12.2 mg, 55%).

LCMS Rt=1.94 minutes, ES$^+$ MS m/z 1215.9 [M+3H]$^+$/3, theoretical mass: 3644.8

Preparation 44

6-(6-(3',5,5'-Tris((22-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)-2,18-dioxo-6,9,12,15-tetraoxa-3,19-diazadocosyl)oxy)-[1,1'-biphenyl]-3-carboxamido)hexanamido) hexanoic Acid

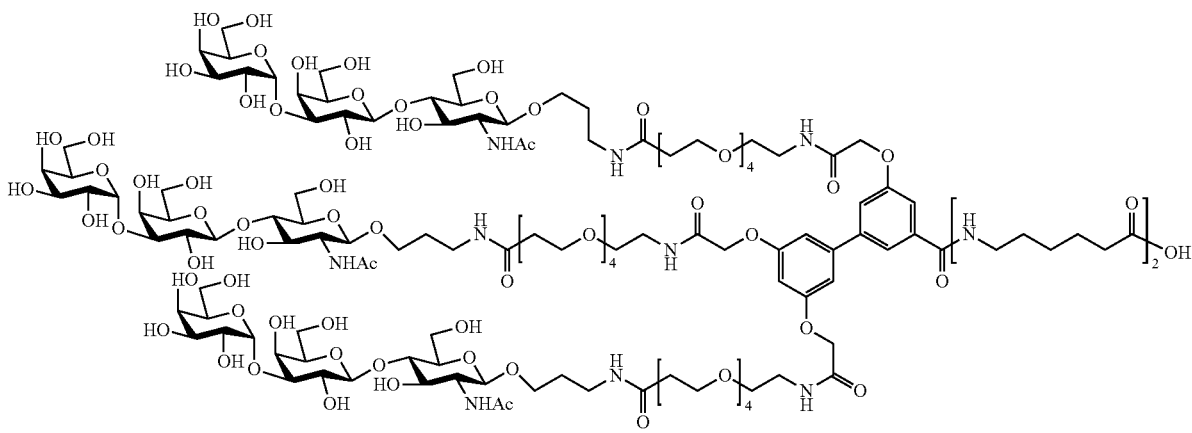

Step 1

To a solution of 3',5,5'-tris((22-(((2R,3R,4R,5S,6R)-3-acetamido-5-(((2S,3R,4S,5S,6R)-3,5-dihydroxy-6-(hydroxymethyl)-4-(((2R,3R,4S,5R,6R)-3,4,5-trihydroxy-6-(hydroxymethyl)tetrahydro-2H-pyran-2-yl)oxy)tetrahydro-2H-pyran-2-yl)oxy)-4-hydroxy-6-(hydroxymethyl)tetrahydro-2H-pyran-2-yl)oxy)-2,18-dioxo-6,9,12,15-tetraoxa-3,19-diazadocosyl)oxy)-[1,1'-biphenyl]-3-carboxylic acid (Preparation 3, 63 mg, 21.61 µmol) in a mixture of DMF (0.5 mL) and DMSO (0.5 mL) was added Et₃N (13.6 µL, 97.3 µmol) and a solution of benzyl 6-(6-aminohexanamido)hexanoate hydrochloride (JACS (2014) 136, 52, 18034-18043, 9.6 mg, 25.9 µmol) in DMF (0.5 mL). HATU (9.9 mg, 25.9 µmol) was added and the reaction was stirred at room temperature overnight. The reaction was concentrated in vacuo and purified using reverse phase column chromatography eluting with 5-40% MeCN in water with 0.1% ammonia to afford the benzyl intermediate residue (50 mg, 72%).

LCMS Rt=1.99 minutes, ES⁺ MS m/z 1615.5 [M+2H]⁺/2, theoretical mass: 3232.4

Step 2

The residue from Step 1 was dissolved in water (1.5 mL) and treated with triethylamine (1.5 mL). The biphasic mixture was stirred at room temperature overnight before concentrating to low volume (0.5 mL). The residue was purified using reverse phase column chromatography eluting with 5-40% MeCN in water with 0.1% ammonia to afford the title compound as a colourless solid (36 mg, 73%).

LCMS Rt=1.56 minutes, ES⁺ MS m/z 1572.6 [M+2H]⁺/2, theoretical mass: 3142.2

Preparation 45

Benzyl 4'-(2-((2-aminoethyl)amino)-2-oxoethoxy)-5-(2-((2-(((4-methoxyphenyl)diphenylmethyl)amino)ethyl)amino)-2-oxoethoxy)-[1,1'-biphenyl]-3-carboxylate

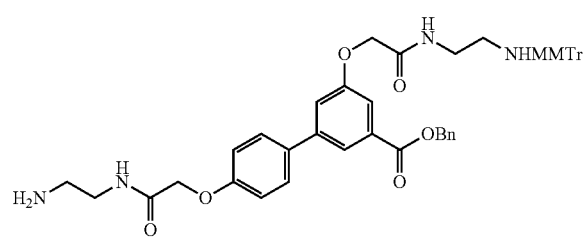

To a solution of benzyl 5-(2-((2-(((4-methoxyphenyl)diphenylmethyl)amino)ethyl)amino)-2-oxoethoxy)-4'-(2-oxo-2-((2-(2,2,2-trifluoroacetamido)ethyl)amino)ethoxy)-[1,1'-biphenyl]-3-carboxylate (Preparation 46, 424 mg, 477.0 µmol) in dioxane (5.0 mL) was added ammonium hydroxide (2.7 mL, 47.7 mmol) and the reaction was stirred at room temperature overnight. A further portion of ammonium hydroxide (2.7 mL, 47.7 mmol) and dioxane (1.5 mL) was added and the reaction was stirred for a further 48 hours. The reaction was concentrated in vacuo and the residue purified using silica gel column chromatography eluting with 5-10% MeOH in DCM to afford the title compound (267 mg, 71%).

LCMS Rt=3.51 mins, ES⁺ MS m/z 793.5 [M+H]⁺

¹H NMR (400 MHz, CDCl₃): δ ppm 7.82-7.80 (1H, m), 7.69-7.58 (1H, br, s), 7.53-7.08 (25H, m), 6.87 (2H, d), 6.72 (2H, d), 5.28 (2H, s), 4.52-4.49 (2H, m), 4.59-4.42 (2H, m), 3.67 (3H, s), 3.59-3.48 (2H, m), 3.37 (2H, m), 3.13-3.01 (2H, m), 2.36-2.27 (2H, m).

Preparation 46

Benzyl 5-(2-((2-(((4-methoxyphenyl)diphenylmethyl)amino)ethyl)amino)-2-oxoethoxy)-4'-(2-oxo-2-((2-(2,2,2-trifluoroacetamido)ethyl)amino)ethoxy)-[1,1'-biphenyl]-3-carboxylate

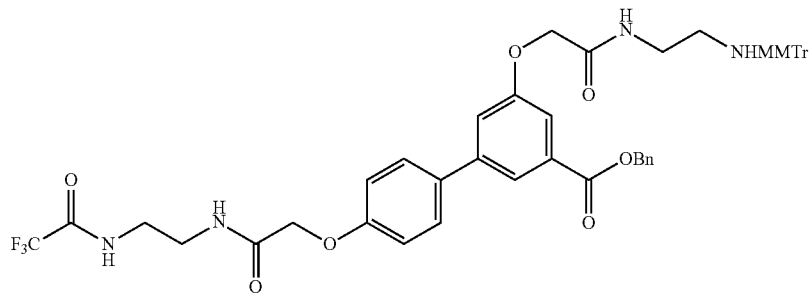

A suspension of benzyl 3-bromo-5-(2-((2-(((4-methoxyphenyl)diphenylmethyl)amino)ethyl)amino)-2-oxoethoxy)benzoate (Preparation 14, 1.00 g, 1.47 mmol), bis(pinacolato)diboron (560 mg, 2.21 mmol) and potassium acetate (433 mg, 4.41 mmol) in dioxane (20 mL) was degassed with nitrogen, and Pd(dppf)Cl₂ (120 mg, 0.15 mmol) was added. The mixture was heated at 100° C. for 18 hours. To the cooled reaction mixture was added N-(2-(2-(4-bromophenoxy)acetamido)ethyl)-2,2,2-trifluoroacetamide (Preparation 47, 543 mg, 1.47 mmol), 1M aq. sodium bicarbonate (4.41 mL, 4.41 mmol) and Pd(dppf)Cl₂ (120 mg 0.15 mmol). The mixture was heated to 100° C. for 21 hours under nitrogen before cooling to room temperature. The reaction mixture was diluted with EtOAc (100 mL) and washed with H₂O (50 mL) and brine (50 mL). The organic layer was dried over magnesium sulphate and concentrated in vacuo. The residue was purified using silica gel column chromatography eluting with 50-75% EtOAc in heptane to afford the title compound as a pale yellow solid (424 mg, 32%).

LCMS Method B: Rt=3.84 mins, ES⁻ MS m/z 887.6 [M−H]⁻

¹H NMR (400 MHz, CDCl₃): δ ppm 7.95-7.92 (1H, m), 7.72 (1H, br, s), 7.08-7.50 (24H, m), 6.91 (2H, d), 6.75 (2H, d), 5.38 (2H, s), 4.65-4.59 (2H, m), 4.59-4.51 (2H, m), 3.73 (3H, s), 3.62-3.49 (4H, m), 3.49-3.41 (2H, m), 2.39-2.31 (2H, m).

Preparation 47

N-(2-(2-(4-Bromophenoxy)acetamido)ethyl)-2,2,2-trifluoroacetamide

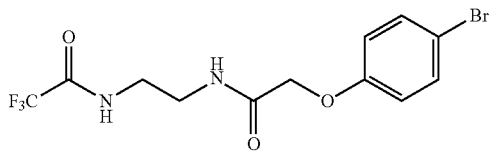 [SMILES: O=C(COc1ccc(Br)cc1)NCCNC(=O)C(F)(F)F]

N-(2-aminoethyl)-2-(4-bromophenoxy)acetamide hydrochloride (Preparation 48, 7.78 g, 25.1 mmol) was suspended in methanol (100 mL). To this was added a solution of NEt₃ (14.0 mL, 100.5 mmol) in methanol (17 mL). The mixture was stirred for 20 minutes, then ethyltrifluoroacetate (7.14 g, 50.3 mmol) was added dropwise. Additional methanol (150 mL) was added and the mixture was stirred at room temperature for 18 hours. The solvent was removed in vacuo and the residue was partitioned between 10% ethanol in ethyl acetate (500 mL) and water (500 mL). The aqueous layer was extracted with additional ethyl acetate (300 mL). The combined organic extracts were dried over MgSO₄ and concentrated in vacuo to afford the title compound as a white solid (8.70 g, 94%).

LCMS Method B: Rt=2.73 mins, ES⁻ MS m/z 369.0 [M–H]⁻

¹H NMR (400 MHz, DMSO): δ ppm 9.43 (1H, br, s), 8.24 (1H, br, s), 7.45 (2H, d), 6.92 (2H, d), 4.44 (2H, s), 3.25-3.20 (4H, m).

Preparation 48

N-(2-Aminoethyl)-2-(4-bromophenoxy)acetamide hydrochloride

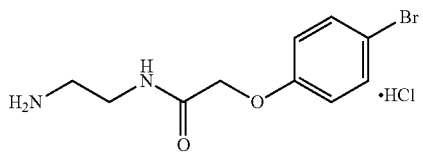 [SMILES: NCCNC(=O)COc1ccc(Br)cc1 ; Cl]

To a solution of tert-butyl (2-(2-(4-bromophenoxy)acetamido)ethyl)carbamate (Preparation 49, 9.00 g, 24.11 mmol) in dioxane (150 mL) was added 4M HCl in dioxane (60 mL) and the reaction was stirred at room temperature for 18 hours. A further portion of 4M HCl in dioxane was added (60 mL) and the mixture was stirred at room temperature for another 18 hours. The solvent was removed in vacuo and the resulting white precipitate was filtered, washed with TBME (300 mL) and dried under vacuum to afford the title compound as the hydrochloride salt in the form of a white solid (7.78 g, <100%).

LCMS Method B: Rt=1.87 mins, no ionization

Preparation 49

Tert-butyl (2-(2-(4-bromophenoxy)acetamido)ethyl)carbamate

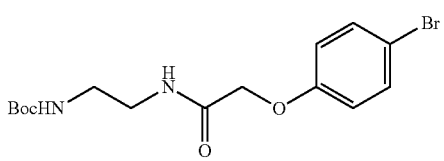 [SMILES: CC(C)(C)OC(=O)NCCNC(=O)COc1ccc(Br)cc1]

To a solution of 2-(4-bromophenoxy)acetic acid (Preparation 50, 7.15 g, 30.9 mmol) in DCM (80 mL) and triethylamine (8.63 mL, 61.9 mmol) was added a solution of Boc-ethylenediamine (5.45 g, 34.0 mmol) in DCM (68 mL) followed by EDC.HCl (8.90 g, 46.4 mmol) and HOBt (7.11 g, 46.4 mmol) and the reaction was stirred at room temperature for 18 hours. The mixture was washed with brine (2×80 mL), dried over MgSO₄ and concentrated in vacuo. The residue was purified using silica gel column chromatography eluting with 40-50% EtOAc in heptane to afford the title compound as a white solid (9.00 g, 78%).

LCMS Method B: Rt=2.94 mins, ES⁺ MS m/z 275.0 [M–Boc+H]⁺, theoretical mass: 373.3

¹H NMR (400 MHz, CDCl₃): δ ppm 7.42 (2H, d), 7.25 (1H, br, s), 6.82 (2H, d), 4.86 (1H, br, s), 4.45 (2H, s), 3.42-3.50 (2H, m), 3.29-3.38 (2H, m), 1.43 (9H, s).

Preparation 50

2-(4-Bromophenoxy)acetic acid

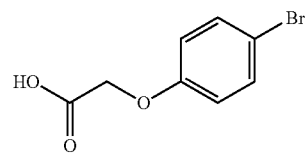 [SMILES: O=C(O)COc1ccc(Br)cc1]

To tert-butyl 2-(4-bromophenoxy)acetate (Preparation 51, 9.84 g, 34.26 mmol) was added a solution of TFA:DCM:H₂O (10:10:1 v/v/v, 98.4 mL) and the resulting mixture was stirred at room temperature for 66 hours. The solvent was removed under vacuo and azeotroped with heptane (2×75 mL) to yield the title compound as a white solid (7.15 g, 91%).

LCMS Method B: Rt=1.59 mins, ES⁻ MS m/z 231.1 [M–H]⁻

¹H NMR (400 MHz, CDCl₃): δ ppm 7.41 (2H, d), 6.81 (2H, d), 4.67 (2H, s).

Preparation 51

Tert-butyl 2-(4-bromophenoxy)acetate

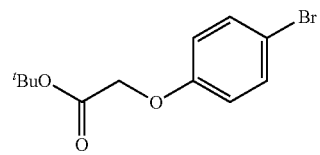 [SMILES: CC(C)(C)OC(=O)COc1ccc(Br)cc1]

To a solution of 4-bromophenol (5.00 g, 28.9 mmol) in DMF (5 mL) was added potassium carbonate (4.79 g, 34.7 mmol). The resulting mixture was stirred for 15 mins then tert-butylbromoacetate (5.12 mL, 34.7 mmol) was added dropwise over 5 mins. The mixture was stirred at room temperature for 2 hours, then diluted with water (75 mL) and ethyl acetate (75 mL). The aqueous layer was extracted with ethyl acetate (60 mL) and the combined organic extracts were washed with water (60 mL) and brine (2×60 mL) then dried over $MgSO_4$. The solvent was removed under vacuo to yield the title compound as a colourless oil (9.78 g, <100%).

LCMS Method B: Rt=3.54 mins, no ionization $^1$H NMR (400 MHz, $CDCl_3$): δ=7.38 (2H, d), 6.77 (2H, d), 4.48 (2H, s), 1.49 (9H, s).

EXAMPLES

Nucleic Acid Aptamer Synthesis

It will be apparent to the skilled person that the nucleic acid aptamers used herein may be synthesised in accordance with techniques within the common general knowledge, such as solid phase nucleotide synthesis (C R Noe, L Kaufhold; Chemistry of Antisense Oligonucleotides in New Trends in Synthetic Medicinal Chemistry, Ed: F Gualtieri; Wiley-VCH, Weinheim, 2000; pp 261-347. ISBN 3527297995).

Aptamer Analysis:

HPLC (XBridge OST C18 column (2.1×50 mm, 2.5 µm) eluting with 1-36% solvent B in solvent A over 30 minutes. (Solvent A=100 mmol HFIP, 16.3 mmol TEA and 1% MeOH in water; solvent B=100 mmol HFIP, 16.3 mmol TEA and 95% MeOH), flow rate 0.25 mL/min.

Synthesis of ($C_6$-amino-linked-SEQ ID PA22 (herein referred to as SEQ ID NO: 3)

The title compound was prepared according to standard solid phase chemistry using standard protocols with commercially available phosphoramidites. To facilitate conjugation to linkers, the nucleotide sequence was terminated with 5'-$NH_2$ using a suitably protected $C_6$-amino-modifier phosphoramidite. Following deprotection the aptamer was HPLC purified. Observed Data: Rt=20.43 minutes; 93.5%; MS 18816.7

Synthesis of ($C_6$-amino-linked-SEQ ID PA23 (herein referred to as SEQ ID NO: 4) The title compound was prepared according to standard solid phase chemistry using standard protocols with commercially available phosphoramidites. To facilitate conjugation to linkers, the nucleotide sequence was terminated with 5'-$NH_2$ using a suitably protected $C_6$-amino-modifier phosphoramidite. Following deprotection the aptamer was HPLC purified. Observed Data: Rt=20.29 minutes; 94.6%; MS 18894.7

General Methods for the Conjugation of Alpha-Gal Clusters and Amino-Linked Aptamers: Method 1

To a solution of the desired carboxylic acid (1 mg, 1 eq) in DMF (30 µL) was added a solution of DMTMM $BF_4$ salt in DMF (2 eq) and the mixture was stirred at room temperature for 40 minutes. 5 eq of the resultant solution was added to a solution of the required $C_6$-amino-linked RNA aptamer (1 eq) in aqueous carbonate buffer and the reaction was stirred for 40 minutes. A further 5 eq of activated acid was added if required and the reaction allowed to stir at room temperature for 1 hour.

The reaction was quenched by the addition of TEAA and purified using reverse phase HPLC using XBridge Prep C18 column (10×50 mm, 5 µm) eluting with a gradient of 5-20% TEAA in MeCN in aqueous TEAA to afford the desired sugar-aptamer conjugate.

General Analytical HPLC Method for Sugar-Aptamer Conjugates:

(XBridge OST C18 column (2.1×50 mm, 2.5 µm) eluting with 1-36% solvent B in solvent A over 30 minutes. (Solvent A=100 mmol HFIP, 16.3 mmol TEA and 1% MeOH in water; solvent B=100 mmol HFIP, 16.3 mmol TEA and 95% MeOH), flow rate 0.25 mL/min.

Method 2

To a solution of the desired carboxylic acid (1 mg, 1 eq) in DMF (30 µL) was added N-hydroxysuccinimide (1.1 eq) followed by diisopropylcarbodiimide (1.05 eq) and the reaction was stirred at room temperature overnight. The resultant mixture was added to a solution of the C6-amino-linked RNA aptamer (1 eq) in aqueous carbonate buffer in two portions separated by 1 hour. The reaction was stirred at room temperature and extra equivalents of NHS-activated acid were added as required to enable formation of the desired reaction product. The resultant solution was purified using preparative reverse phase HPLC as described in Method 1 to afford the desired aptamer-sugar conjugate.

Examples 1-4 may be prepared according to General Methods 1 or 2 using RNA aptamer 1 ($C_6$-amino-linked-SEQ ID NO:79, PCT/GB2015/051812; herein referred to as SEQ ID NO: 1) and the appropriate carboxylic acid as described below:

Example 1

Synthesis of RNA Aptamer Conjugate 1

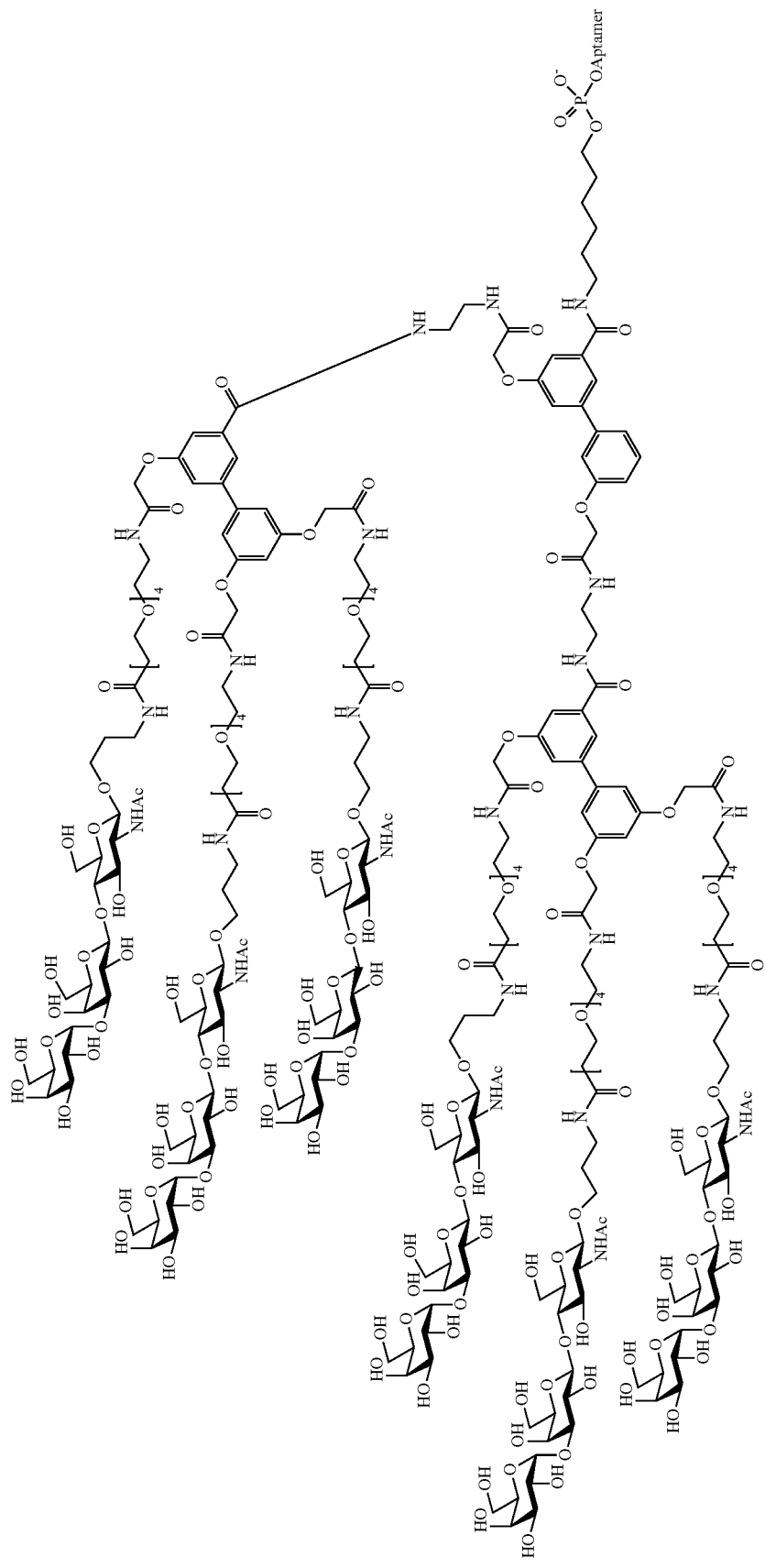

Precursor: Preparation 1
Calculated MWt: 20516.7
Observed Data: Rt=23.50 minutes; 85%; MS 20517.2

Example 2

Synthesis of RNA Aptamer Conjugate 2

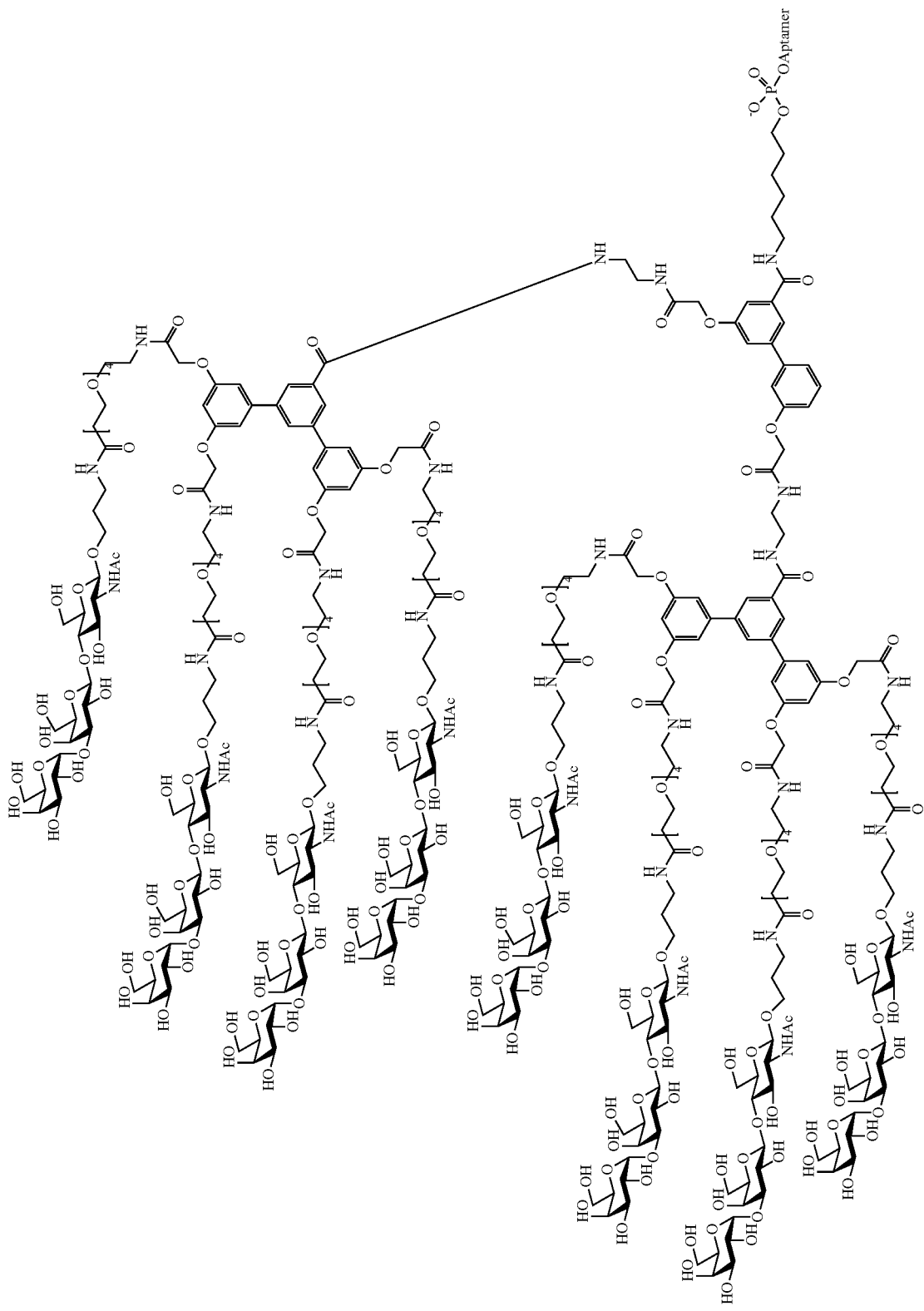

Precursor: Preparation 22
Calculated MWt: 22481.1
Observed Data: Rt=25.94 minutes; 82.7%; MS 22480.0

Example 4

Synthesis of RNA Aptamer Conjugate 4

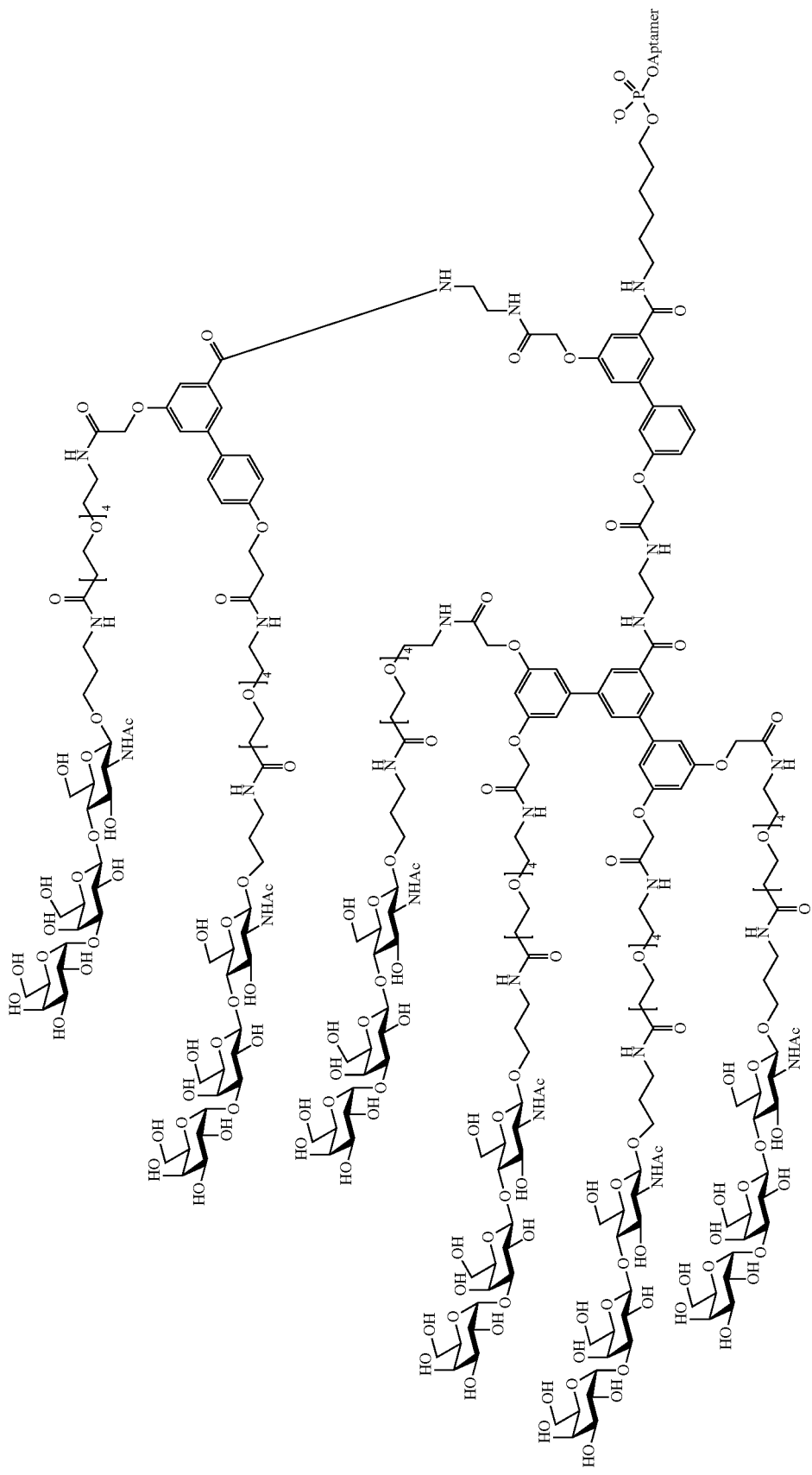

Precursor: Preparation 28
Calculated MWt: 20593.7
Observed Data: Rt=25.52 minutes; 86.9%; MS 20592.7

Example 4

Synthesis of RNA Aptamer Conjugate 4

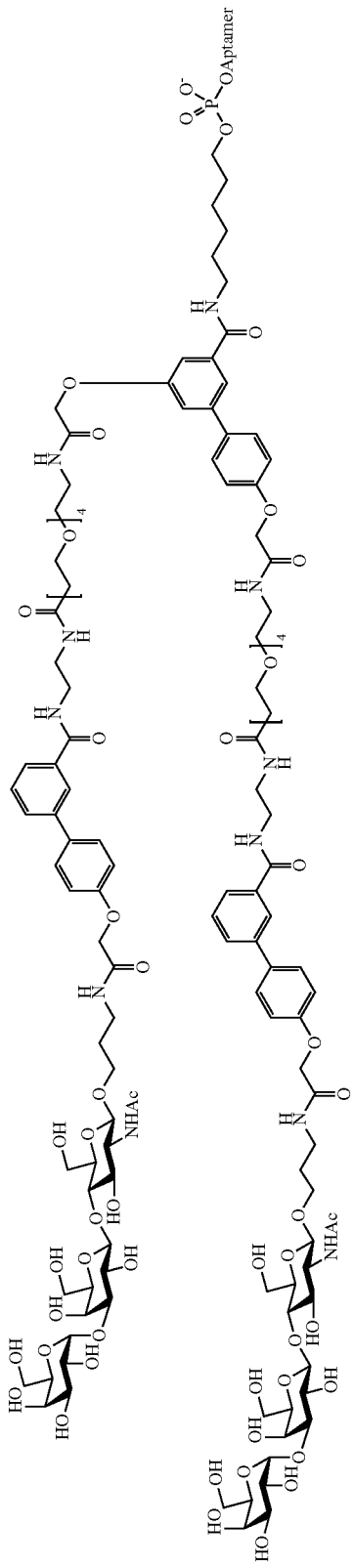

Precursor: Preparation 34
Calculated MWt: 16894.0
Observed Data: Rt=25.56 minutes; 80.3%; MS 16894.5

Examples 5-7 may be prepared according to the General Methods 1 or 2 using RNA aptamer 2 ($C_6$-amino-linked-SEQ ID A9g; herein referred to as SEQ ID NO: 2) and the appropriate carboxylic acid as described below:

Example 5

Synthesis of RNA Aptamer Conjugate 5

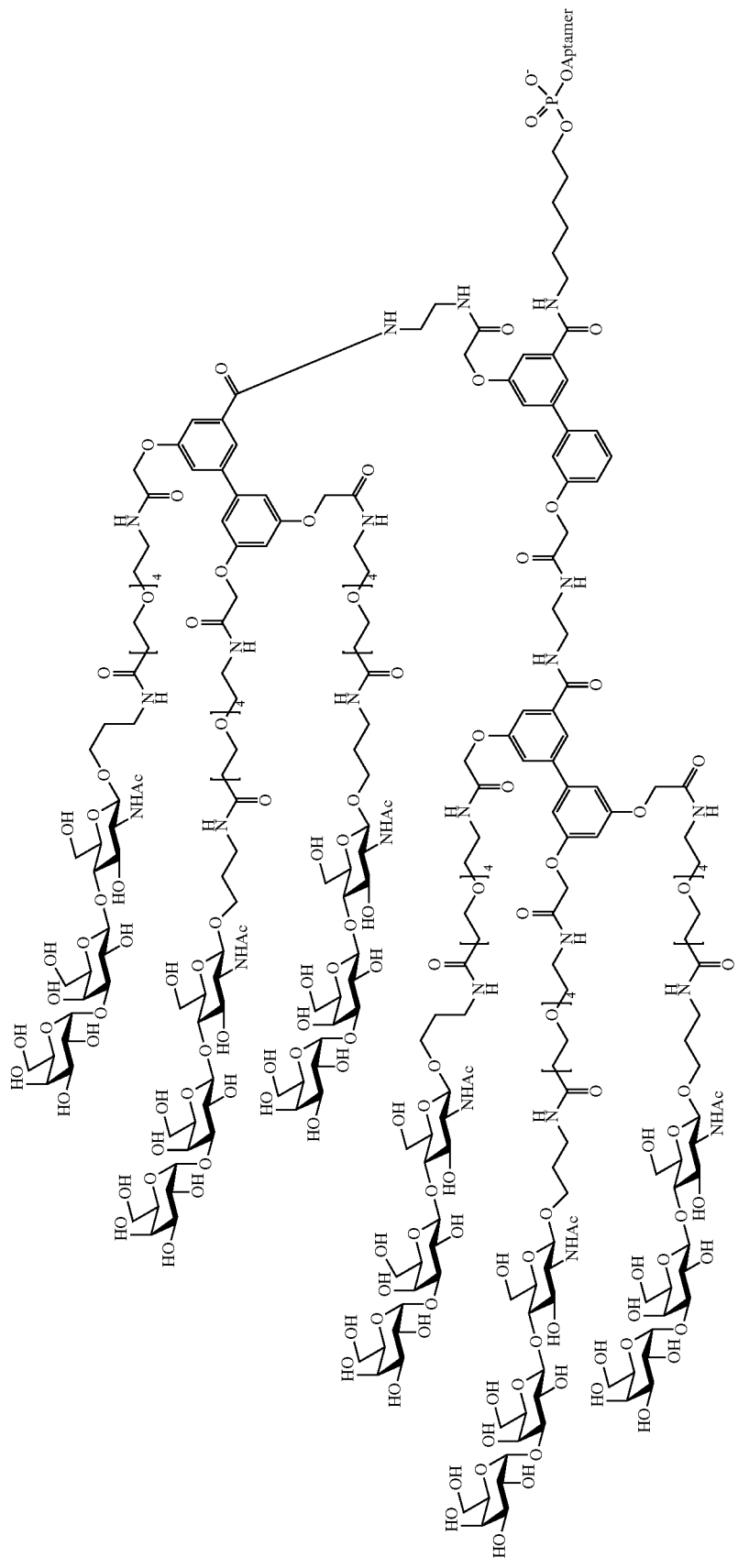

Precursor: Preparation 1
Calculated MWt: 20438
Observed Data: Rt=22.88 minutes; 89.10%; MS 20438.1

Example 6

Synthesis of RNA Aptamer Conjugate 6

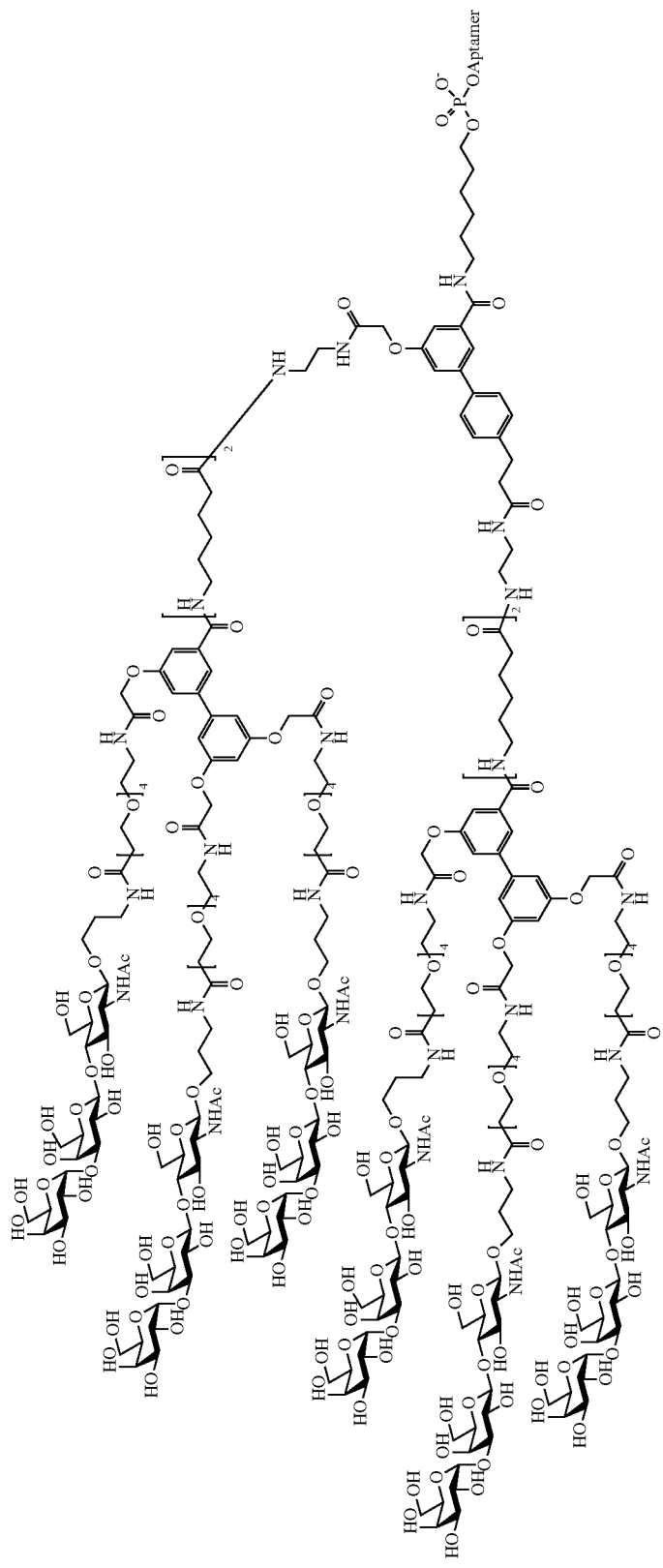

Precursor: Preparation 42
Calculated MWt: 20891.7
Observed Data: Rt=26.51 minutes; 93.9%; MS 20893.5

Example 7

Synthesis of RNA Aptamer Conjugate 7

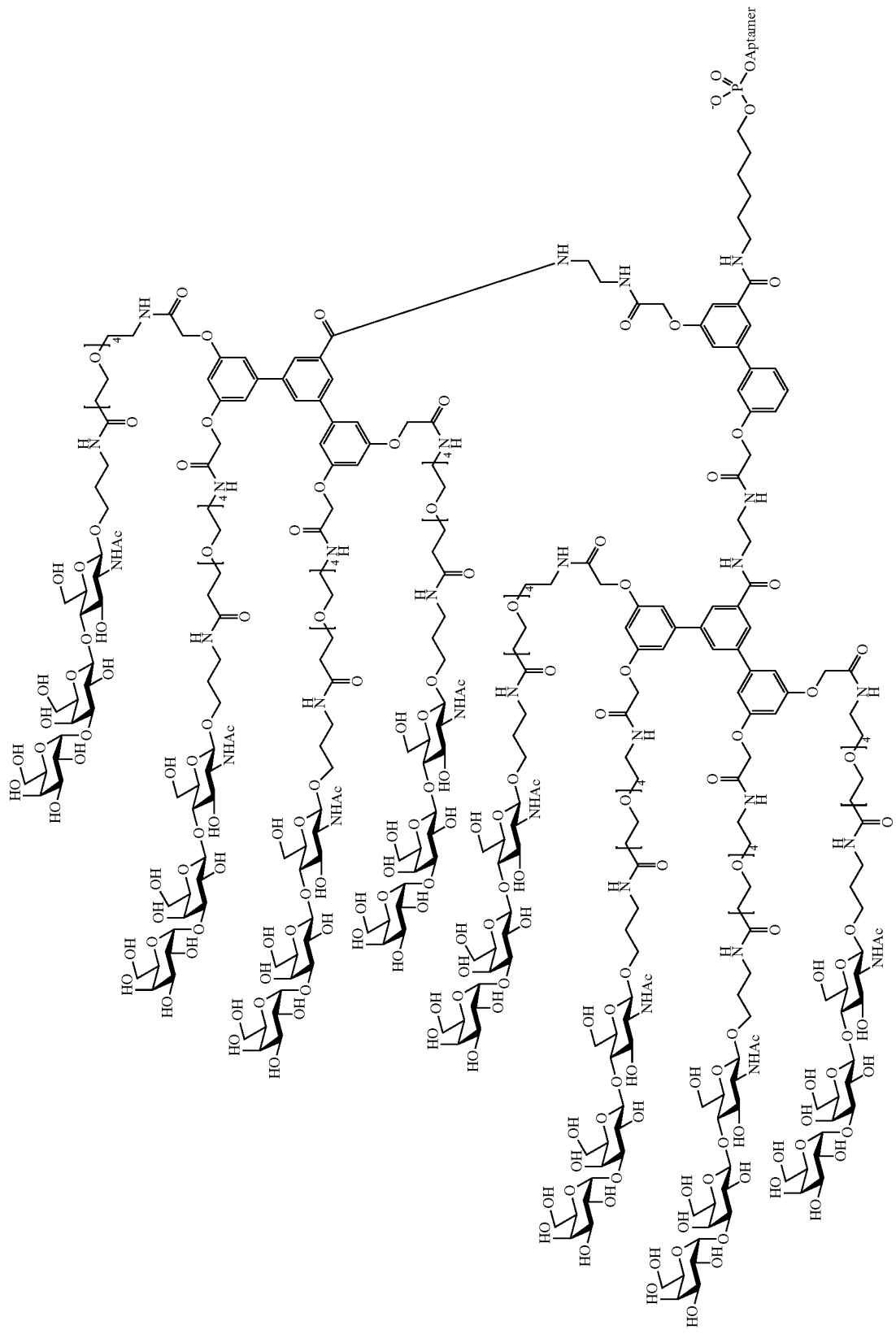

Precursor: Preparation 22
Calculated MWt: 22403.6
Observed Data: Rt=24.93 minutes; 69.7%; MS 22404.3

Example 8

Example 8 may be prepared according to General Method 1 using RNA aptamer 3, $C_6$-amino-linked-SEQ ID PA22 (herein referred to as SEQ ID NO: 3) and the appropriate carboxylic acid as described below:

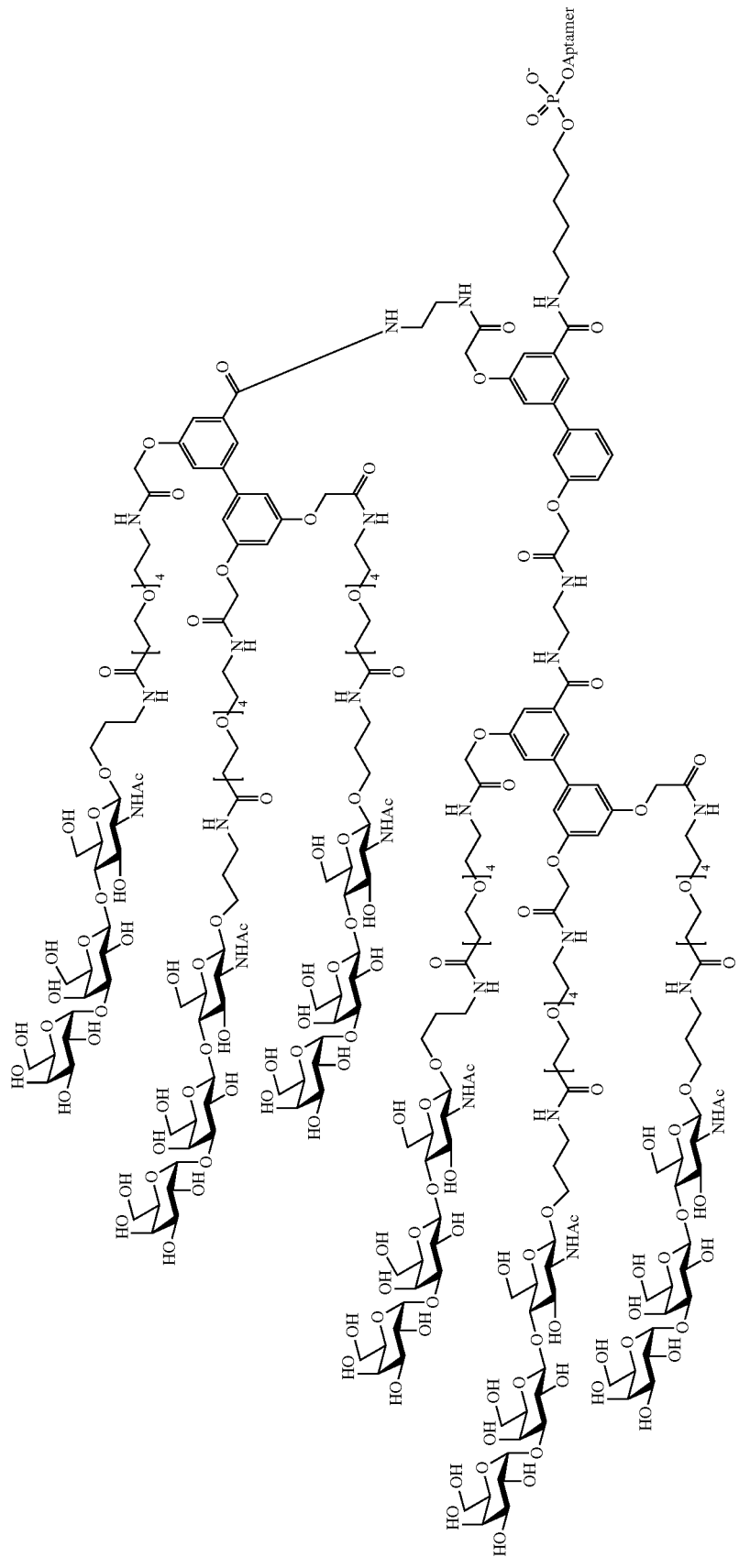

Precursor: Preparation 1
Calculated MWt: 25025.5
Observed Data: Rt=23.94 minutes; 85.9%; MS 25026.2

Example 9

Example 9 may be prepared according to General Method 1 using RNA aptamer 4, C amino-linked-SEQ ID PA23 (herein referred to as SEQ ID NO: 4) and the appropriate

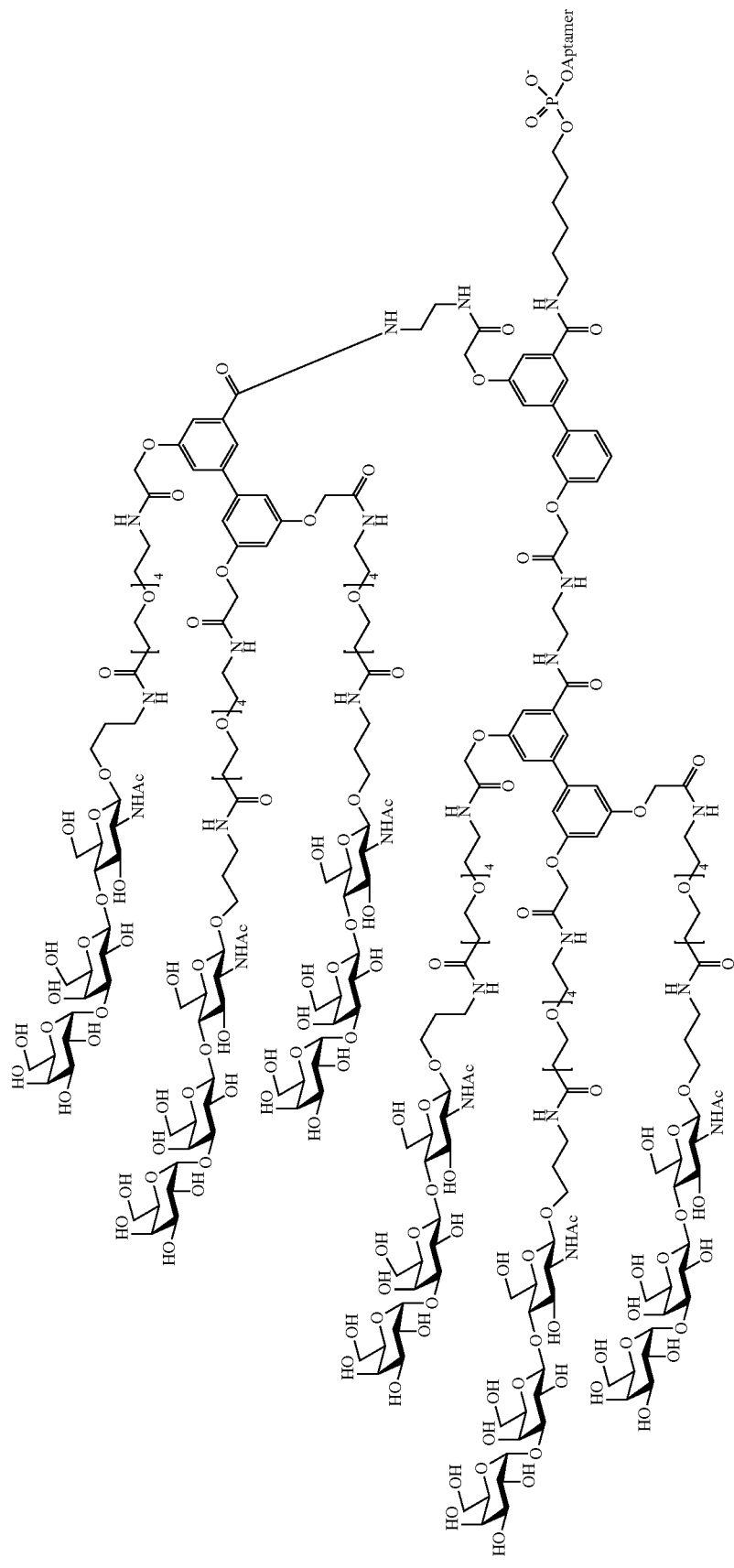

Precursor: Preparation 1
Calculated MWt: 25103.5
Observed Data: Rt=23.86 minutes; 88.3%; MS 25104.2

Assays

Flow Cytometry Assay Using Alpha-Galactosyl IgG Antibody for Examples Prepared Using RNA Aptamer 1, $C_6$-Amino-Linked-SEQ ID NO:79, PCT/GB2015/051812; Herein Referred to as SEQ ID NO: 1)

Flow cytometry was used to demonstrate binding of L (as an EGFR nucleic acid aptamer, RNA aptamer 1, $C_6$-amino-linked-SEQ ID NO:79, PCT/GB2015/051812; herein referred to as SEQ ID NO: 1) to a receptor on a human cell line and F (as the carbohydrate molecule capable of binding to a human anti-alpha-galactosyl antibody). A431 cells are used to capture the EGFR nucleic acid aptamer as it is well known that the cells significantly over-express the EGFR receptor. A secondary phycoerythrin labelled anti-human IgG antibody was used to detect binding of alpha-galactosyl IgG antibody to the compound.

The compounds were heated to 70° C. for 10 minutes and cooled to room temperature for 10 minutes prior to use in the assay.

A431 cells (ATCC CRL-1555) were harvested and resuspended at $5 \times 10^6$ cells/mL in phosphate buffered saline (PBS) (Sigma D8662)+0.1% BSA (Bovine Serum Albumin—Sigma A2153)+0.1 mg/mL Yeast t-RNA (Invitrogen 15401-011)+5 mM $MgCl_2$ (Sigma M1028) and incubated on ice for 30 minutes to block. $5 \times 10^5$ cells were then incubated with compound at various concentrations as described below or buffer alone at room temperature, shaking at 450 rpm for 1 hour. The cells were washed with 3×200 μL PBS+0.1% BSA, prior to adding 50 μL of Anti-alpha galactosyl IgG antibody (custom purification from human IVIG, Rockland Immunochemicals, Inc.) at 35 μg/mL in PBS+0.1% BSA and incubating at 4° C. for 1 hour. The cells were further washed with 3×200 μL PBS+0.1% BSA before being treated with 100 μL 1:40 dilution of Anti-Human IgG-PE (phycoerythrin) (Biolegend 409303) at 4° C. for 1 hour. After a final wash of 3×200 μL PBS+0.1% BSA the cells were resuspended in 200 μL PBS+0.1% BSA and evaluated on a flow cytometer (FC500 Beckman Coulter). Data from all samples were analysed in the Kaluza software package (Beckman Coulter).

FIG. 1 demonstrates the capture of anti-alpha galactosyl IgG antibodies to the cell surface using Example 1 (FIG. 1A), Example 2 (FIG. 1B), Example 3 (FIG. 1C) and Example 4 (FIG. 1D). The shift in fluorescence intensity (PE) occurs due to the binding event at each end of the molecule.

Figure 2:
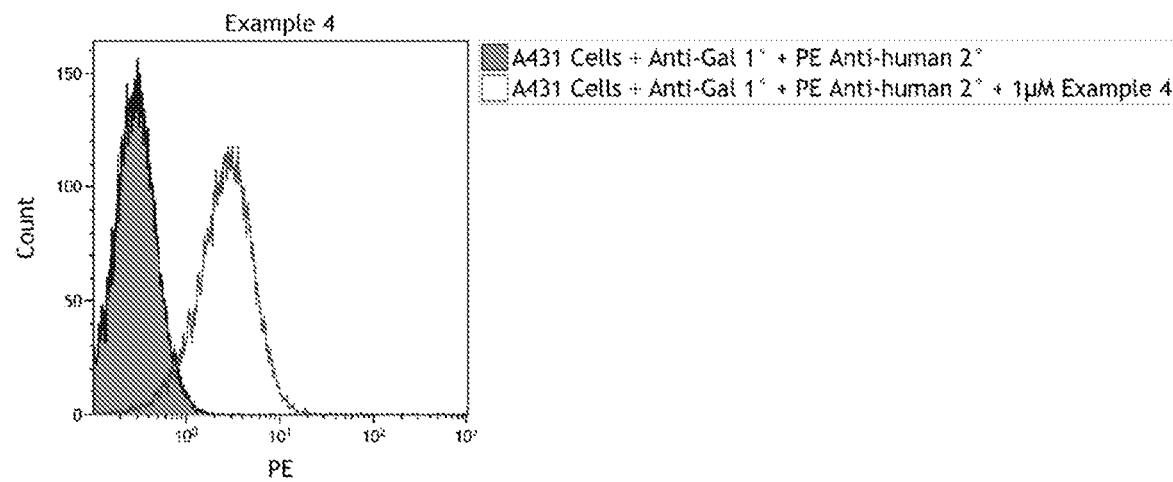
FIG. 2: is a dose titration of Examples 2-4 using the Flow Cytometry assay described.
Figure 2:
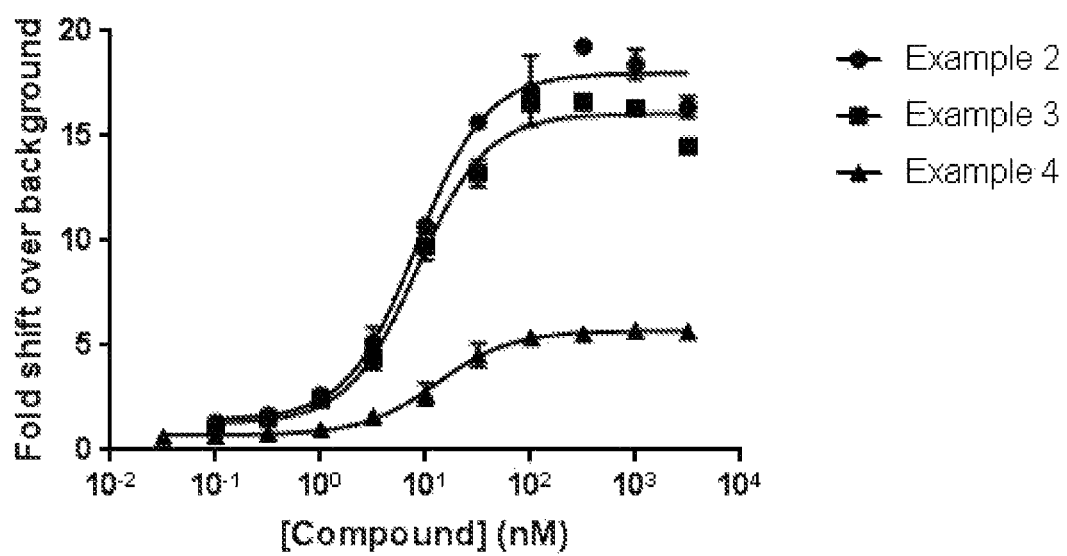

FIG. 2 is a dose titration of Examples 2-4 using the Flow Cytometry assay described. FIG. 2 demonstrates a difference in recruitment of anti-galactosyl antibodies to the human cancer cell line A431 by Examples 2-4. Increasing recruitment is reported by an increase in fold shift over background.

Figure 11:
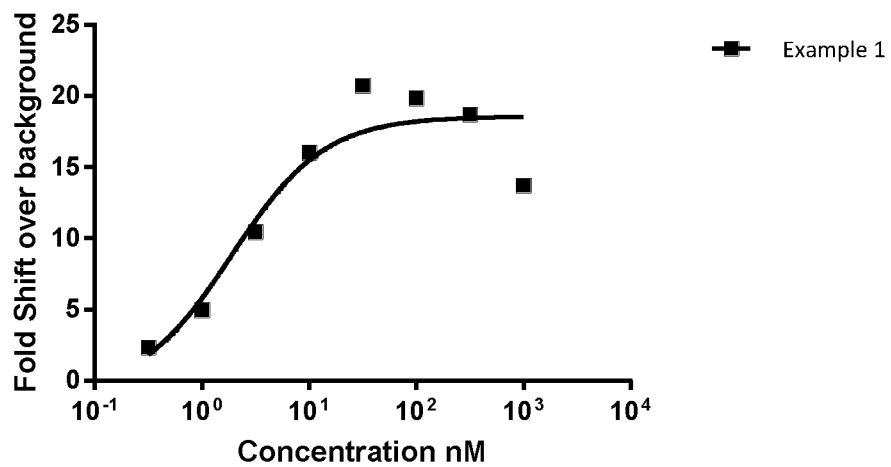
FIG. 11: is a dose titration of Example 1 using the Flow Cytometry assay using alpha-galactosyl IgG antibody.

FIG. 11 is a dose titration of Example 1 using the IgG flow cytometry assay described.

Table 3 demonstrates binding activity of Examples 1-4 using the flow cytometry assay described above. The fold shift over background was calculated by dividing the Mean Fluorescence Intensity (MFI) obtained in the presence of 10 nM or 1 μM alphamer by the Mean Fluorescence Intensity (MFI) obtained in the absence of alphamer. The fold shift over background is reported as a geometric mean with standard error in brackets. The number of independent experiments is also reported. In order to achieve a signal both ends of the molecule are required to bind (aptamer to EGFR on the cell surface of the A431 cells and alpha-galactosyl to anti-alpha galactosyl antibodies).

TABLE 3

| Compound | Fold Shift in Binding Assay at 10 nm | Fold Shift in Binding Assay at 1 μM | Number of Tests (n) |
| --- | --- | --- | --- |
| Example 1 | 7.7 (2.3) | 9.8 (3.3) | n = 2 |
| Example 2 | 10.7 | 18.4 | n = 1 |
| Example 3 | 9.7 | 16.3 | n = 1 |
| Example 4 | 3.4 (0.9) | 7.5 (1.2) | n = 4 |

Flow Cytometry Assay Using Alpha-Galactosyl IgM Antibodies for Examples Prepared Using RNA Aptamer 1, $C_6$-Amino-Linked-SEQ ID NO:79, PCT/GB2015/051812; Herein Referred to as SEQ ID NO: 1)

Flow cytometry was used to demonstrate binding of L (as an EGFR nucleic acid aptamer, RNA aptamer 1, C6-amino-linked-SEQ ID NO:79, PCT/GB2015/051812; herein referred to as SEQ ID NO: 1) to a receptor on a human cell line and F (as the carbohydrate molecule capable of binding to a human anti-alpha-galactosyl antibody). A431 cells significantly over-express EGFR so are used to capture the EGFR nucleic acid aptamer. A secondary phycoerythrin labelled anti-human IgM antibody was used to detect binding of the alpha-galactosyl IgM antibody to the compound.

A431 cells (ATCC CRL-1555) were harvested and resuspended at 5×106 cells/mL in Binding Buffer (BB) which made of phosphate buffered saline (PBS+/+) (Sigma D8662)+0.1% BSA (Bovine Serum Albumin—Sigma A2153), 0.1 mg/ml salmon sperm DNA+5 mM MgCl2.

$5 \times 10^5$ cells were then incubated with compound at a range of concentrations or binding buffer alone at room temperature, shaking at 450 rpm for 1 hour.

The cells were washed with 2×200 μL PBS+0.1% BSA, prior to adding 50 μL of anti-Gal M86 IgM (Absolute Ab) (31.25 μg/ml) in PBS+0.1% BSA and incubating at 4° C. for 1 hour. The cells were washed with 2×200 μL PBS+0.1% BSA, prior to adding 100 μL of secondary anti-IgM-PE Ab (Biolegend 314508). The cells were incubated at 4° C. for 30 minutes in dark. After a final wash of 2×200 μL PBS+0.1% BSA the cells were resuspended in 200 μL PBS+0.1% BSA and evaluated on a flow cytometer (FC500 Beckman Coulter). Data from all samples were analysed in the Kaluza software package (Version 1.5a, Beckman Coulter).

Figure 12:
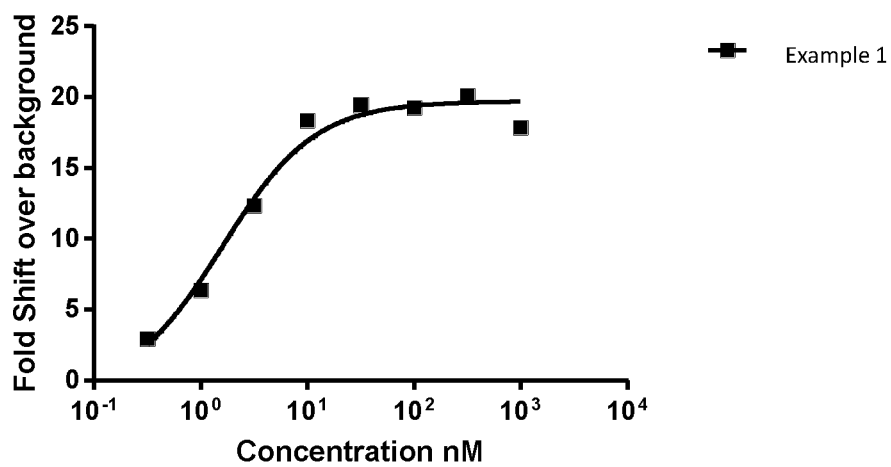
FIG. 12: is a dose titration of Example 1 using the Flow Cytometry assay using alpha-galactosyl IgM antibody.

FIG. 12 is a dose titration of Example 1 using the IgM flow cytometry assay described.

Flow Cytometry Assay Using C3b Antibodies for Examples Prepared Using RNA Aptamer 1, $C_6$-Amino-Linked-SEQ ID NO:79, PCT/GB2015/051812; Herein Referred to as SEQ ID NO: 1)

Flow cytometry was used to demonstrate binding of the compounds to a cell line of interest and recruitment of the C3b complement component to the cell.

A431 cells were used to capture the EGFR binding nucleic acid aptamer, RNA aptamer 1, SEQ ID No: 1, as it is well known that the cells significantly over-express the EGFR receptor. Anti-C3b antibody conjugated to phycoerythrin (PE) was used to detect recruitment of C3b molecules to cells after addition of compound at varying concentrations.

A431 cells (ATCC CRL-1555) were harvested and resuspended at $5 \times 10^6$ cells/mL in Binding Buffer (BB) which made of phosphate buffered saline (PBS+/+) (Sigma D8662)+0.1% BSA (Bovine Serum Albumin—Sigma A2153), 0.1 mg/ml salmon sperm DNA+5 mM MgCl2.

5×10⁵ cells were then incubated with compound at a range of concentrations, or binding buffer alone at room temperature, shaking at 450 rpm for 1 hour. The cells were washed with 2×200 μL PBS+0.1% BSA, prior to adding 100 μL PBS and 100 μL 20% Human Serum (HS) (Patricell 23590) or Heat Inactivated Human Serum (HIHS) with 25 μg/ml M86 IgM (Absolute Antibody) and incubating at 37° C. for 25 minutes.

Figure 13:
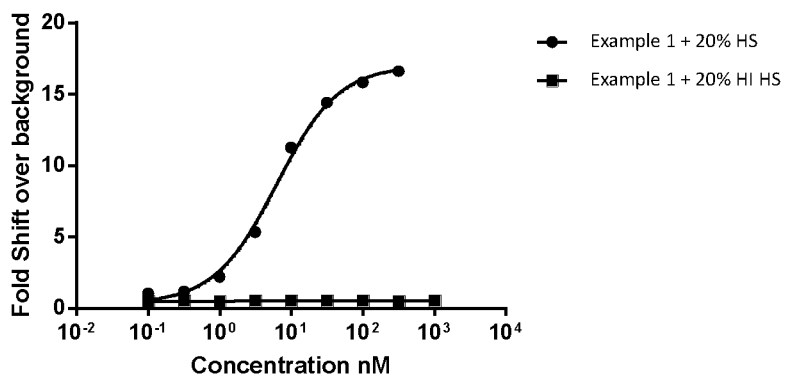
FIG. 13: is a dose titration of Example 1 using the C3b deposition assay described.

The cells were washed with 2×200 μL PBS+0.1% BSA, prior to adding 100 μL of anti-C3b-PE (3E7/C3b, Biolegend 846104). The cells were incubated at 4° C. for 30 minutes in dark. After a final wash of 2×200 μL PBS+0.1% BSA the cells were resuspended in 200 μL PBS+0.1% BSA and evaluated on a flow cytometer (FC500 Beckman Coulter). Data from all samples were analysed in the Kaluza software package (Version 1.5a, Beckman Coulter). FIG. 13 demonstrates the level of C3b deposition on A431 cells with varying concentrations of Example 1+20% HS compared to Example 1+20% HI HS.

Phagocytosis of Target Cells by Macrophages for Examples Prepared Using RNA Aptamer 1, $C_6$-Amino-Linked-SEQ ID NO:79, PCT/GB2015/051812; Herein Referred to as SEQ ID NO: 1)

Phagocytosis was used to demonstrate the functional effect of the binding of L (as an EGFR nucleic acid aptamer, RNA aptamer 1, herein referred to as SEQ ID NO: 1) to a receptor on a cell line and F (as the carbohydrate molecule capable of binding to a human anti-alpha-galactosyl antibody). eHap cells, engineered to overexpress EGFR were used as target cells. Monocyte derived macrophages were used as effector cells. Purified hIVIG was used a source of anti-Gal antibodies. The measured increase in integrated intensity occurs due to the phagocytosis of the target cells. No such increase is observed under control conditions (cells alone or in the absence of compound).

Effector cells were differentiated in situ in 96-well-plates (Corning 3603). Briefly, blood from each healthy donor retained in a leukoreduction system chamber was purchased from the National Health Service (Addenbrooke's Hospital, Cambridge, UK). Peripheral blood mononuclear cells (PBMCs) were isolated using the Lymphoprep™ system following manufacturer's instructions (STEMCELL Technologies 07861). Monocytes were isolated from PBMCs by positive selection using the EasySep™ Human CD14 Positive Selection Kit II (STEMCELL Technologies 17858), re-suspended in ImmunoCult™-SF Macrophage Medium (STEMCELL Technologies 10961) supplemented with Recombinant human GM-CSF (Peprotech 300-03) at 100 ng/ml and plated at 20,000 cells/well in a cell culture incubator (5% $CO_2$, 37° C.). After 5 days of differentiation, macrophages were polarised towards the M1 phenotype with 100 ng/ml IFN-γ (Peprotech 300-02) and 1 ng/ml lipopolysaccharide (Invitrogen tlrl-eblps) for a further two days. eHAP cells (C669) were engineered to overexpress the human Epidermal Growth Factor Receptor (EGFR) by Horizon Discovery and cultured in Iscove's Modified Dulbecco's Medium (Gibco® 21980-032) supplemented with 10% Fetal Bovine Serum (Gibco® 10500-064), and used as target cells. Target cells were harvested using a Cell Dissociation Buffer (Gibco® 13151014), counted and labelled 10 mM pHrodo Green STP ester (Thermo Fisher Scientific P35369) at 1 μl per 1.0×10⁶ cells of for 30 mins at 37° C. Cells were washed in complete medium, counted and then treated with varying concentrations of Example 1 or Example 3 for 1 hour at room temperature with shaking. Cells were then washed in serum free medium. Incubate with 70 μg/ml anti-alpha galactosyl IgG antibody (custom purification from human IVIG) for 30 mins on ice, washed in Dulbecco's Phosphate Solution (Gibco® 14190-094) and co-cultured with effector cells (target:effector ratio 5:1) for up to 12 hours at 37° C. in the IncuCyte® (Sartorius). Images were acquired every two hours. Data were analysed using the IncuCyte®ZOOM software (Version 2016A, Sartorius). Graphs were produced with GraphPad Prism (Version 6).

Figure 14A:
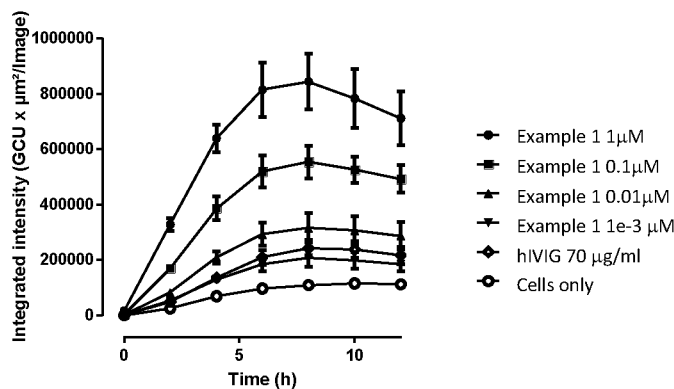
FIG. 14: demonstrates compound mediated phagocytosis in the presence of Example 1 (FIG. 14A) and Example 3
(FIG. 14B). The target cells (EGFR expressing eHAP cells) were phagocytosed by the effector cells (macrophages) in a manner dependent on the compound dose, over a period of 12 hours. The increase in the integrated intensity occurs due to the compound driven phagocytosis of the target cells.
Figure 14B:
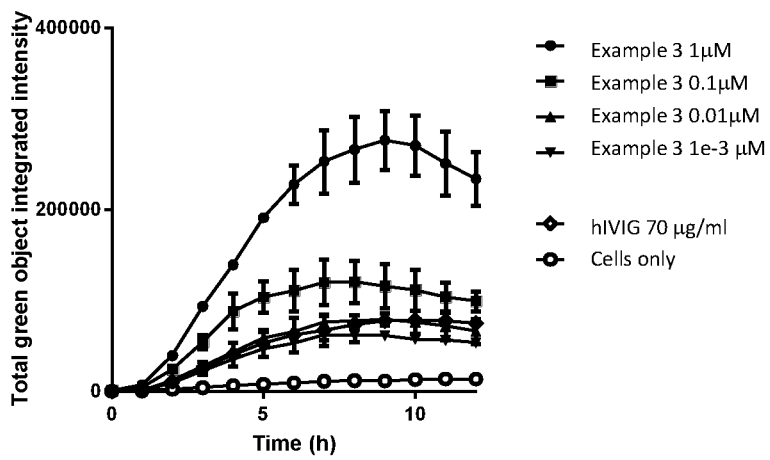

FIG. 14A demonstrates dose dependent phagocytosis due to Example 1. FIG. 14B demonstrates dose dependent phagocytosis due to Example 3.

Flow Cytometry Assay Using Alpha-Galactosyl IgG Antibody for Examples Prepared Using RNA Aptamer 2 $C_6$-Amino-Linked-SEQ ID NO:8, WO 2013 012921; Herein Referred to as SEQ ID NO: 2)

Flow cytometry was used to demonstrate binding of L (as a PSMA nucleic acid aptamer, RNA aptamer 2, $C_6$-amino-linked-SEQ ID NO:8, WO 2013 012921; herein referred to as SEQ ID NO: 2) to a receptor on a human cell line and F (as the carbohydrate molecule capable of binding to a human anti-alpha-galactosyl antibody). LNCaP cells are used to capture the PSMA nucleic acid aptamer as it is well known that the cells significantly over-express the PSMA receptor. A secondary phycoerythrin labelled anti-human IgG antibody was used to detect binding of alpha-galactosyl IgG antibody to the compound.

The compounds were heated to 70° C. for 10 minutes and cooled to room temperature for 10 minutes prior to use in the assay.

LNCaP cells (ATCC CRL-1740) were harvested and resuspended at 5×10⁶ cells/mL in phosphate buffered saline (PBS) (Sigma D8662)+0.1% BSA (Bovine Serum Albumin—Sigma A2153)+0.1 mg/mL Yeast t-RNA (Invitrogen 15401-011)+5 mM $MgCl_2$ (Sigma M1028) and incubated on ice for 30 minutes to block. 5×10⁵ cells were then incubated with compound at various concentrations as described below or buffer alone at room temperature, shaking at 450 rpm for 1 hour. The cells were washed with 3×200 μL PBS+0.1% BSA, prior to adding 50 μL of Anti-alpha galactosyl IgG antibody (Anti-alpha-galactosyl antibody was purified from human IVIG (Gammagard) by affinity purification using an alpha-galactosyl-HSA (Human Serum Albumin) sepharose column by Rockland Immunochemicals Inc.) at 35 μg/mL in PBS+0.1% BSA and incubating at 4° C. for 1 hour. The cells were further washed with 3×200 μL PBS+0.1% BSA before being treated with 100 μL 1:40 dilution of Anti-Human IgG-PE (phycoerythrin) (Biolegend 409303) at 4° C. for 1 hour. After a final wash of 3×200 μL PBS+0.1% BSA the cells were resuspended in 200 μL PBS+0.1% BSA and evaluated on a flow cytometer (FC500 Beckman Coulter). Data from all samples were analysed in the Kaluza software package (Beckman Coulter).

Figure 3:
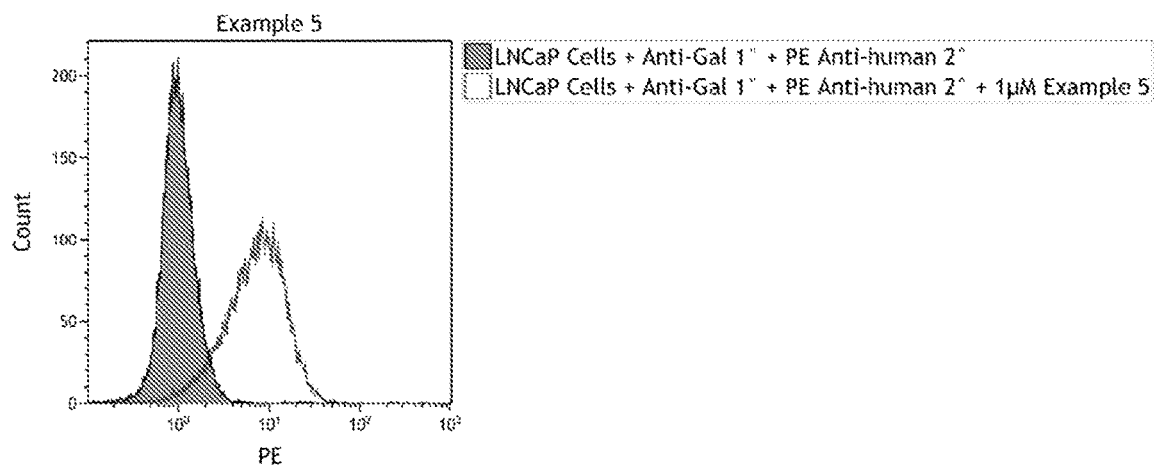
FIG. 3: demonstrates the capture of anti-alpha galactosyl IgG antibodies to the cell surface using Example 5 (FIG. 3A), Example 6 (FIG. 3B) and Example 7 (FIG. 3C).
Figure 3:
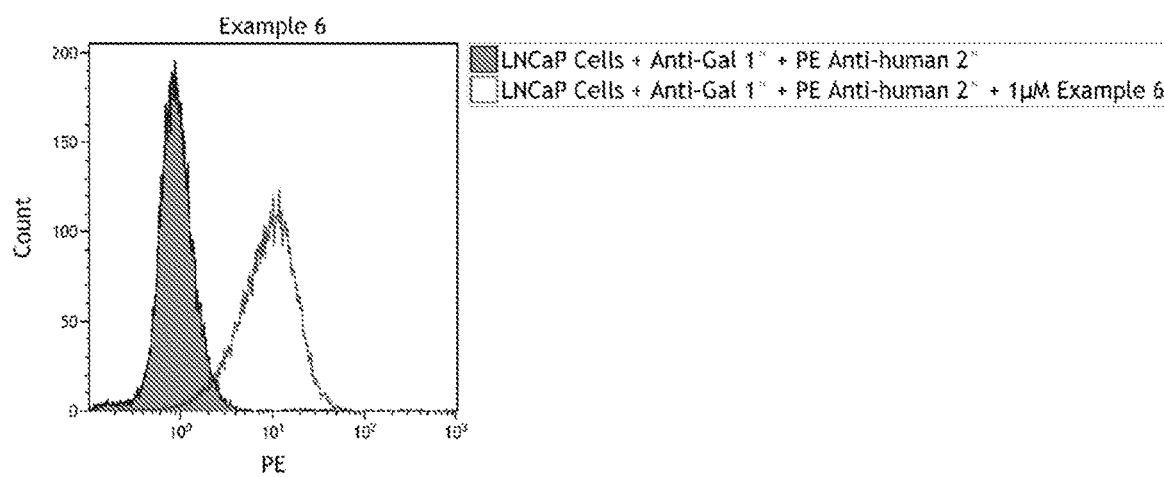
Figure 3:
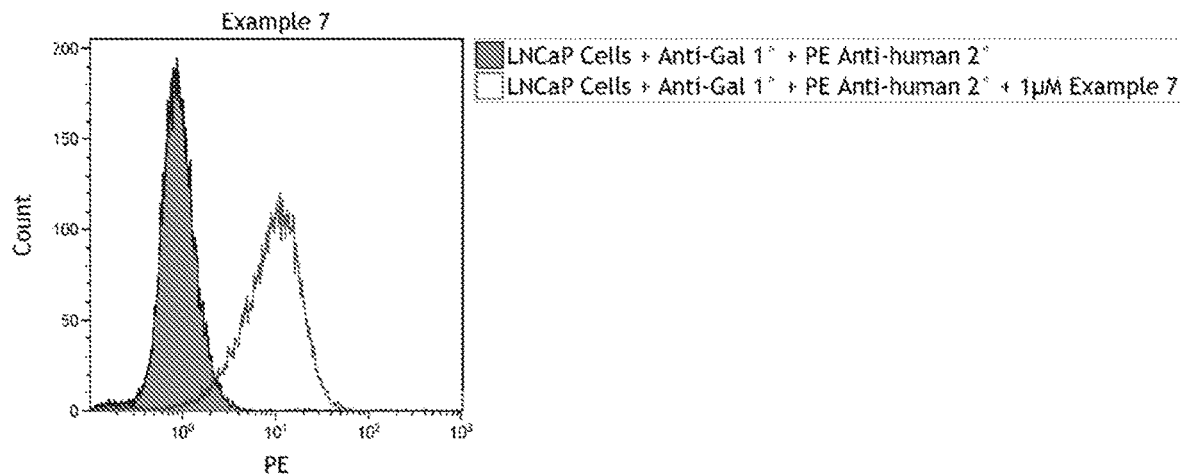

FIG. 3 demonstrates the capture of anti-alpha galactosyl IgG antibodies to the cell surface using Example 5 (FIG. 3A), Example 6 (FIG. 3B) and Example 7 (FIG. 3C). The shift in fluorescence intensity (PE) occurs due to the binding event at each end of the molecule.

Figure 4:
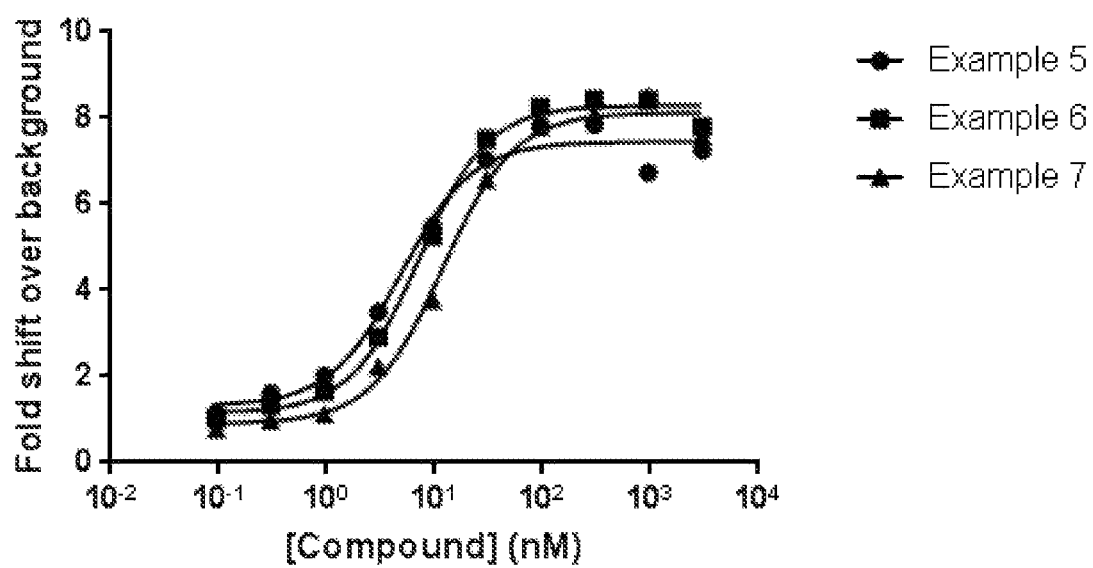
FIG. 4: is a dose titration of Examples 5-7 using the Flow Cytometry assay described.

FIG. 4 is a dose titration of Examples 5-7 using the Flow Cytometry assay described. Increasing recruitment of anti-galactosyl IgG antibodies is reported by an increase in fold shift over background.

Table 4 demonstrates binding activity of Examples 5-7 using the flow cytometry assay described above (Assay 2). The fold shift over background was calculated by dividing the Mean Fluorescence Intensity (MFI) obtained in the presence of 10 nM or 1 μM alphamer by the Mean Fluorescence Intensity (MFI) obtained in the absence of alphamer. The fold shift over background is reported as a geometric mean with standard error in brackets. The number of independent experiments is also reported. In order to achieve a signal both ends of the molecule are required to bind (aptamer to PSMA on the cell surface of the LNCaP cells and alpha-galactosyl to anti-alpha galactosyl antibodies).

TABLE 4

| Compound | Fold Shift in Binding Assay at 10 nm | Fold Shift in Binding Assay at 1 µM | Number of Tests (n) |
|---|---|---|---|
| Example 5 | 7.8 (2.3) | 11.1 (4.3) | n = 2 |
| Example 6 | 5.33 | 8.5 | n = 1 |
| Example 7 | 3.82 | 8.6 | n = 1 |

Fluorescein Amidite (FAM) Labelled Aptamer Binding to *P. aeruginosa*

Flow cytometry was used to demonstrate the binding of fluorescein labelled oligonucleotides to *P. aeruginosa*. A generalised method is presented below:

Oligonucleotides were made to 500 µM in molecular biology grade Tris EDTA buffer, pH 8.0 (VWR E112) and held at 85° C. for 5 minutes, 4° C. 3 min, 37° C. 10 min. Oligonucleotides were then held on ice prior to use in the assay. The assays were carried out in polystyrene 96-well U bottom plates (Costar). The 96-well plates were pre-blocked with casein blocking buffer (Thermo Fisher 37528) and then washed three times with (PBS$^{-/-}$) (Sigma D8537) prior to assay. *P. aeruginosa* (ATCC 27853, NCTC12903) were grown in LB broth (Fisher BP1426-500) to late exponential phase, as measured by Optical Density at 595 nM of 0.6 absorbance units. *P. aeruginosa* cultures were frozen in assay ready aliquots in PBS/30% glycerol stocks and stored at −80° C. Bacteria were prepared for assay by centrifugation at 10 000 rpm for 5 minutes and washed twice in an equivalent volume of PBS+0.1% BSA (Sigma A2153), after the final wash pellets were resuspended in a PBS/0.1% BSA/0.1 mg/ml salmon sperm DNA) to a bacterial density of approximately $3 \times 10^9$ CFU/mL. Bacterial samples (1.5× $10^8$ CFU) were then incubated with various concentrations of FAM labelled oligonucleotide or buffer alone, at room temperature, shaking at 450 rpm for 45 minutes. Samples were washed with 3×200 µL PBS$^{-/-}$ (centrifuged at 4000 rpm, 5 minutes) and finally resuspended in 150 µL PBS$^{-/-}$. Aptamer binding to *P. aeruginosa* bacteria was defined by an increase in Median Fluorescence Intensity (MFI) following profiling on a CytoFlex FACS machine (Beckman Coulter). Data from all samples were analysed using the CytExpert software package (Beckman Coulter). The fold shift over background was calculated by dividing the MFI obtained in the presence of oligonucleotide by the MFI obtained in the absence of oligonucleotide.

Figure 5:
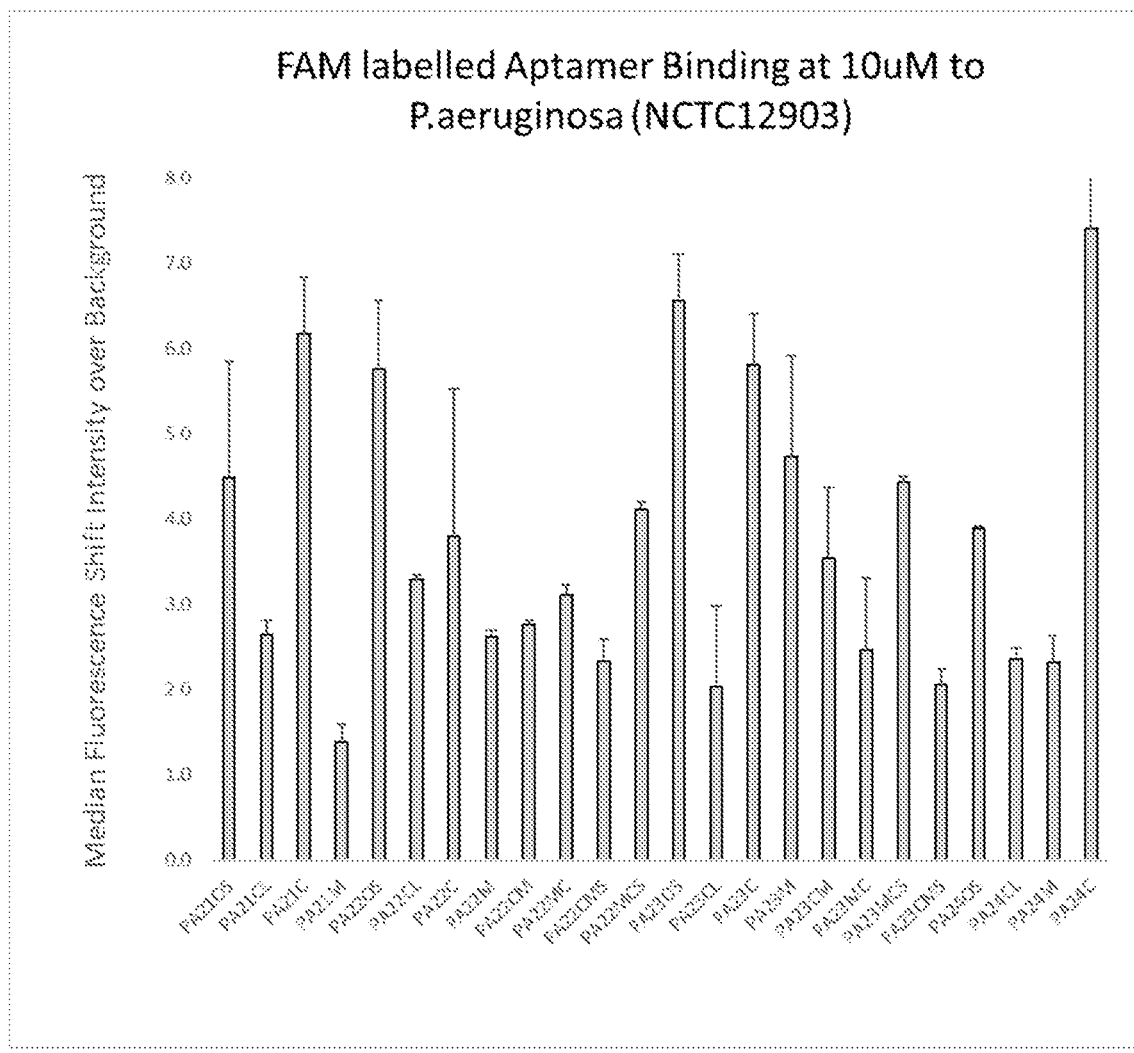
FIG. 5: Representative Fixed Dose Data (10 µM) for Aptamer Binding to *P. aeruginosa*.

FIG. 5: illustrates representative binding for SEQ ID NO: 9-SEQ ID NO: 32 at a fixed dose of 10 µM to *P. aeruginosa* (ATCC 27853, NCTC12903). The shift in fluorescence intensity occurs due to the binding event of the molecule to the bacterial surface. The fold shift over background was calculated by dividing the MFI obtained in the presence of oligonucleotide by the MFI obtained in the absence of oligonucleotide. Samples were run in duplicates. The data illustrates that differences in oligonucleotide sequence result in differences in the magnitude of binding to the *P. aeruginosa* bacteria.

Figure 6:
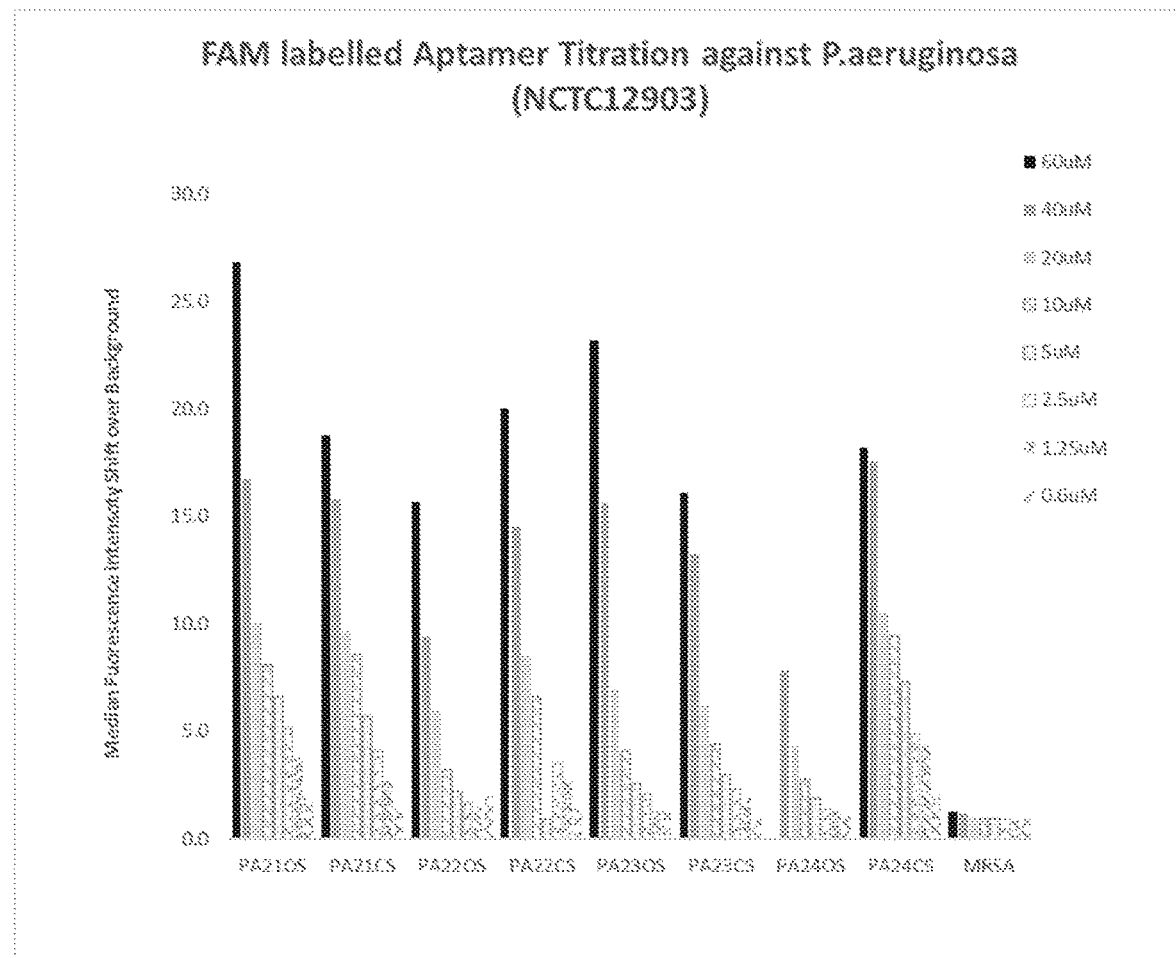
FIG. 6: Representative Dose Response Data for Selected Aptamer Binding to *P. aeruginosa*, quantified by MFI shift over background. MRSA aptamer is a negative control aptamer raised to *S. aureus*: (UGAGUGCCAUUGGUUA-CAGGAUGUUUCUGGUUGAAUCUGGAAUGCAUUG-CAUCACG UCGCU (SEQ ID NO: 37). Composition; 2'F Guanine, 2'methoxy Cytosine, 2'methoxy Uracil, 2'methoxy Adenine. 5' labelled with Fluorescein amidite (FAM) and 3' capped with inverted dT).

FIG. 6: illustrates representative dose response data for aptamer binding, over a concentration range from 0.6 µM to 60 µM, to *P. aeruginosa* (ATCC 27853, NCTC12903). The shift in fluorescence intensity occurs due to the binding event of the molecule to the bacterial surface. The fold shift over background was calculated by dividing the MFI obtained in the presence of oligonucleotide by the MFI obtained in the absence of oligonucleotide. PA21OS=SEQ ID NO: 11, PA21C=SEQ ID NO: 13, PA22OS=SEQ ID NO: 9, PA22C=SEQ ID NO: 16, PA23OS=SEQ ID NO: 10, PA23C=SEQ ID NO: 23, PA24OS=SEQ ID NO: 29, PA24C=SEQ ID NO: 32. The MRSA oligonucleotide sequence is a negative control aptamer raised to *S. aureus*: (UGAGUGCCAUUGGUUACAGGAUGUUUCUG-GUUGAAUCUGGAAUGCAUUGCAUCACG UCGCU (SEQ ID NO:37). Composition; 2'F Guanine, 2'methoxy Cytosine, 2'methoxy Uracil, 2'methoxy Adenine. 5' labelled with Fluorescein amidite (FAM) and 3' capped with inverted dT).

Figure 7:
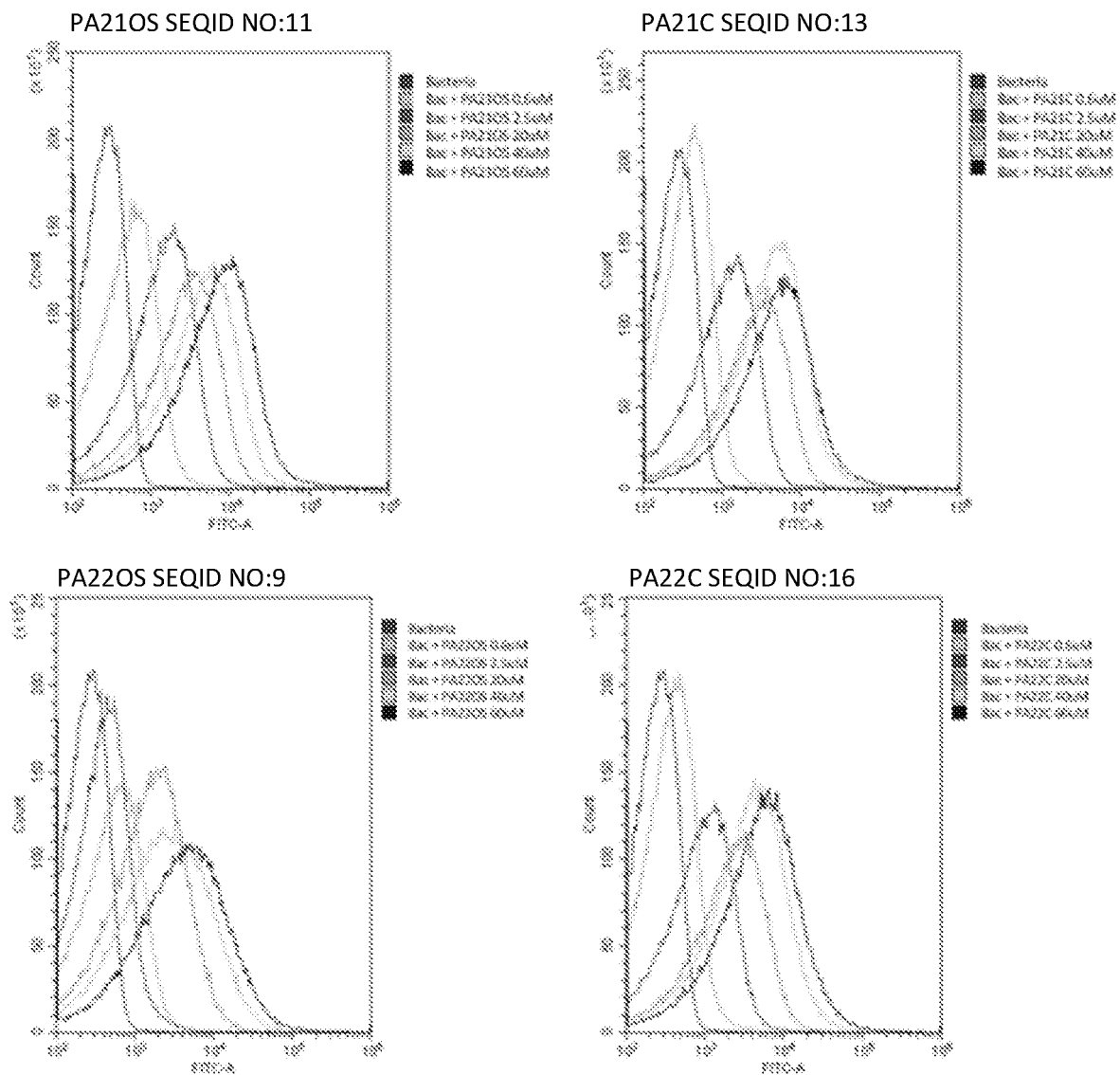
FIG. 7: Representative Dose Response Data for Individual Aptamer Binding to *P. aeruginosa*, visualised by fluorescence histogram.

FIG. 7: illustrates representative dose response data for aptamer binding, over a concentration range from 0.6 µM to 60 µM, to *P. aeruginosa* (ATCC 27853, NCTC12903); visualised by histograms of fluorescence intensity. The shift in fluorescence intensity occurs due to the binding event of the molecule to the bacterial surface. The fluorescence histograms were generated using the CytExpert software package (Beckman Coulter).

Flow Cytometry Assay—Aptamer Binding to Bacteria

Flow cytometry was used to demonstrate the specific binding of fluorescein labelled oligonucleotides to *P. aeruginosa*. A generalised method is presented below:

The compounds were dissolved in nuclease-free $dH_2O$ and used directly in the assay or heated to 70° C. for 10 minutes and cooled to room temperature for 10 minutes prior to use in the assay.

The assays were carried out in polystyrene 96-well U bottom plates (Costar). The 96-well plates were pre-blocked with casein blocking buffer (Thermo Fisher 37528) and then washed three times with (HBSS+/+) (Life Technologies 14025-050) prior to assay. *P. aeruginosa* (ATCC 27853), *E. coli* (NCTC 10583) or *S. aureus* (NCTC 10833) were grown in LB broth (Fisher BP1426-500) to late exponential growth phase. For growth-dependent binding studies, the bacteria were grown to various growth stages, determined by measuring $OD_{595}$, as shown in FIG. 9. Subsequently, the bacteria were centrifuged at 10 000 rpm for 5 minutes and resuspended in HBSS+/+ at a bacterial density of $2 \times 10^9$ CFU/mL. Baclight Red bacterial stain (Thermo Fisher B-35001) or Celltrace Far Red Cell staining kit (Thermo Fisher C34564) was added to the bacteria to a final concentration of 1 µM. For Baclight red stain the bacteria were incubated at room temperature in the dark for 10 minutes followed by two washes with HBSS+/+. For the Celltrace Far Red cell staining, the bacteria were incubated at room temperature in the dark for 20 minutes. PBS (Sigma D8662)+1% BSA (Sigma A2153) was added to the bacteria (5 times the volume of the original bacteria suspension) and was incubated for 10 minutes at room temperature in the dark. Bacteria were centrifuged (10 000 rpm, 5 minutes) and resuspended in HBSS+/+ at a concentration of $2 \times 10^9$ CFU/mL. $1 \times 10^8$ CFU were then incubated with various concentrations (see FIG. 8) of SEQ ID NO: 10 or buffer alone, at room temperature, shaking at 450 rpm for 1 hour. The bacteria were washed with 3×200 µL HBSS+/+(centrifuged at 4000 rpm, 5 minutes) and finally resuspended in 200 µL HBSS+/+ and evaluated on a FC500 (Beckman Coulter). Data from all samples were analysed in the Kaluza software package (Beckman Coulter). Samples were run in duplicates and experiment was repeated twice.

Flow Cytometry Assay—Binding of Aptamers to Mammalian Cell Line

The compounds were dissolved in nuclease-free $dH_2O$ and used directly in the assay or heated to 70° C. for 10 minutes and cooled to room temperature for 10 minutes prior to use in the assay.

The assays were carried out in polystyrene 96-well U bottom plates (Costar). The 96-well plates were pre-blocked with casein blocking buffer (Thermo Fisher 37528) and then washed three times with (HBSS+/+) (Life Technologies 14025-050) prior to assay.

A431 cells (ATCC CRL-1555) were harvested and resuspended at $1 \times 10^7$ cells/mL in phosphate buffered saline (PBS) (Sigma D8662) $4.5 \times 10^5$ cells were then incubated with compound at various concentrations (see FIG. 4) of SEQ ID NO: 10 or buffer alone at room temperature, shaking at 450 rpm for 1 hour. The cells were washed with $3 \times 200$ µL HBSS+/+(centrifuged at 4000 rpm, 5 minutes) and finally resuspended in 200 µL HBSS+/+ and evaluated on a FC500 (Beckman Coulter). Data from all samples were analysed in the Kaluza software package (Beckman Coulter). Samples were run in duplicates and experiment was repeated twice.

Figure 8:
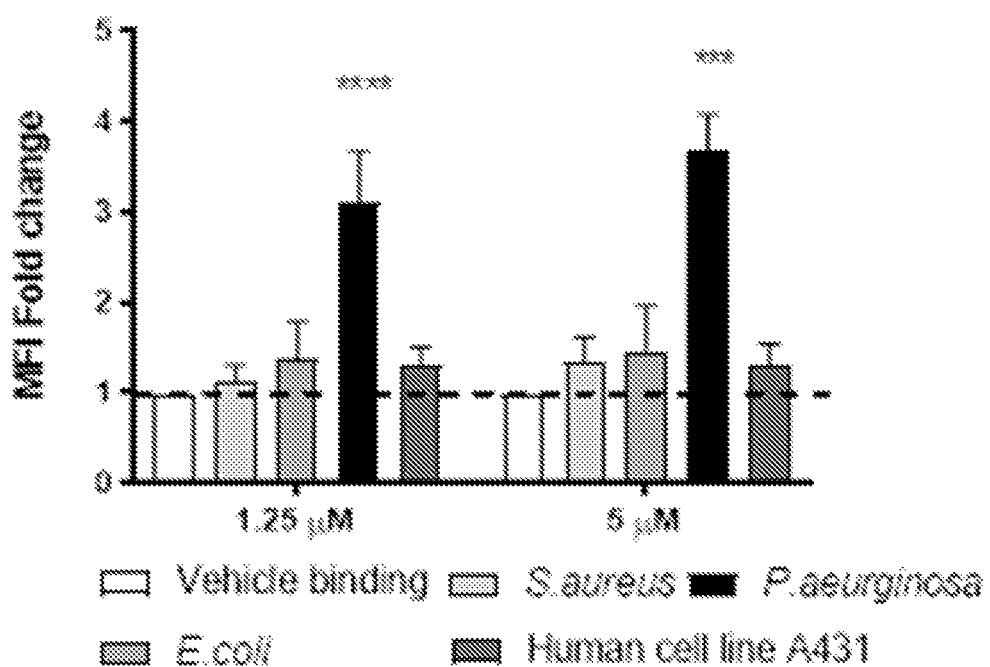
FIGS. 8 to 10: Results of flow cytometry assay demonstrating aptamer binding to bacteria and mammalian cell line.
Figure 9:
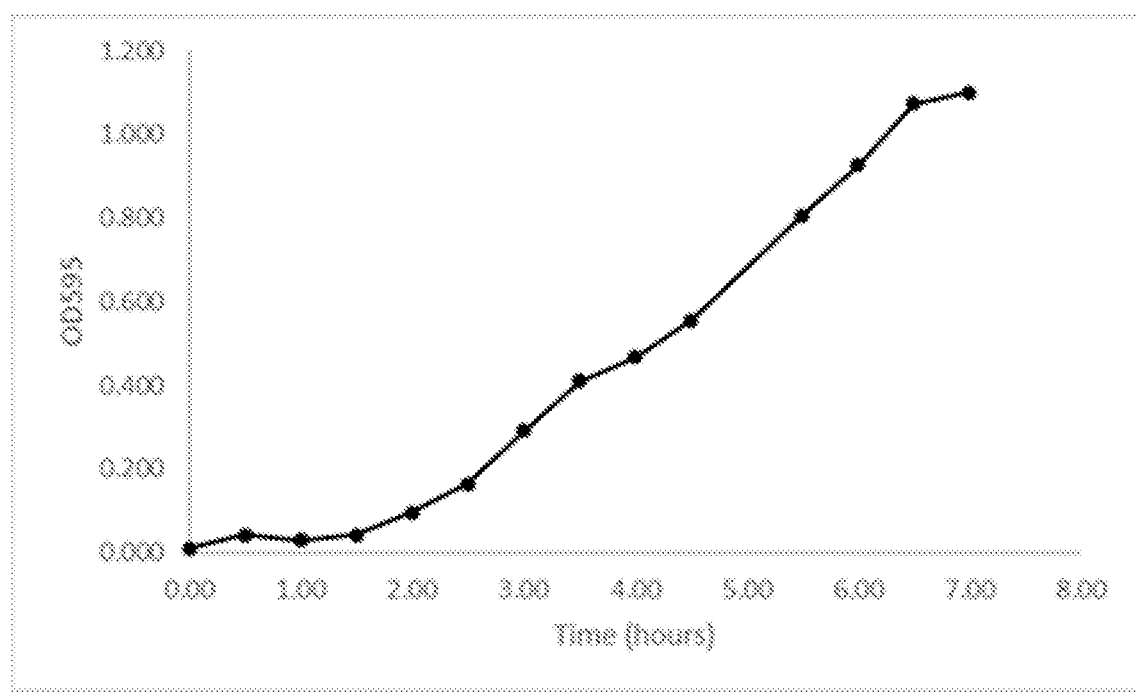

FIG. 8 demonstrates the specific binding of SEQ ID NO: 10 to *P. aeruginosa* ATCC 27853, over *E. coli* NCTC 10583, *S. aureus* NCTC 10833 and human cell line A431 concentrations 5 µM and 1.25 µM. The shift in fluorescence intensity (FITC) occurs due to the binding event of the molecule to the cell or bacterial surface. Increased binding of SEQ ID NO: 10 reported by an increase in MFI emanating from the fluorescently labelled molecule. The fold shift over background was calculated by dividing the MFI obtained in the presence of compound by the MFI obtained in the absence of compound, and is reported with standard error in brackets. The data was analysed with one-way ANOVA in GraphPad Prism 7.02 (GraphPad Software Inc, US). ***$p \leq 0.001$).

Figure 10:
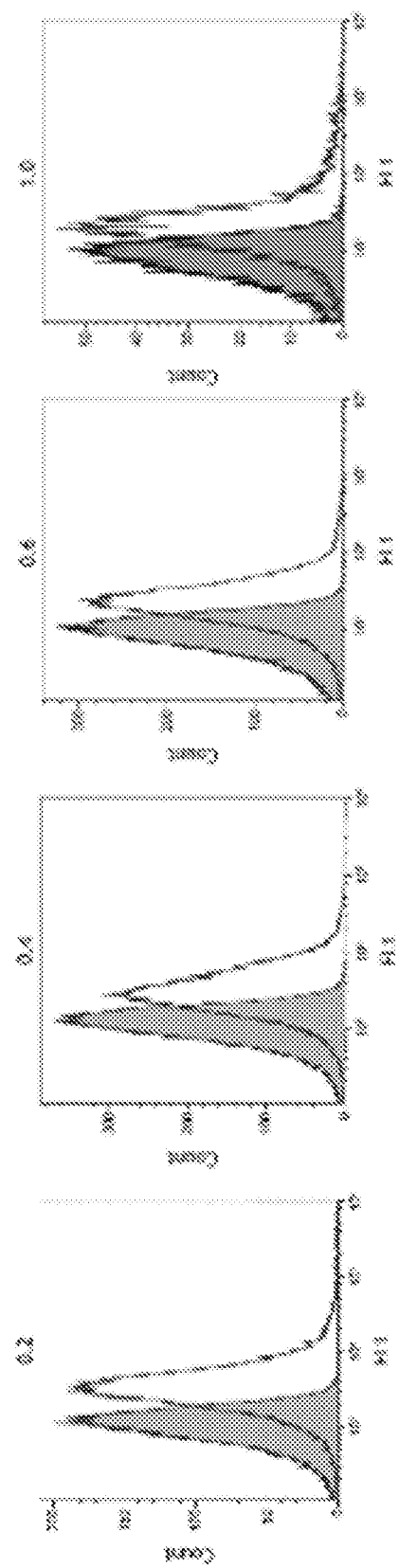

FIGS. 9 and 10 are representative data of the binding of SEQ ID NO: 10 (10 µM) to *P. aeruginosa* ATCC 27853 at various bacterial growth. The growth stages *P. aeruginosa* ATCC 27853 as measured by $OD_{595}$ on Envision plate reader, is shown in FIG. 9. The binding of SEQ ID NO: 10 is exemplified in FIG. 10 with *P. aeruginosa* ATCC 27853 at bacteria $OD_{595}=0.2$, $OD_{595}=0.4$, $OD_{595}=0.6$ and $OD_{595}=1.0$. The shift in fluorescence intensity (FITC) occurs due to the binding event of the molecule to the bacterial surface.

Flow Cytometry Assay Using Alpha-Galactosyl IM Antibodies for Examples 8 and 9 Prepared Using SEQ ID NO: 3 and SEQ ID NO: 4 Respectively)

Flow cytometry was used to screen for binding of Example 8 and Example 9 to *P. aeruginosa* bacteria. A generalised method is presented below.

Test compounds were dissolved to 200 µM in TE buffer (10 mM Tris, 0.1 EDTA, pH 8.0) and heated to 70° C. for 10 minutes and cooled to room temperature for 10 minutes prior to use in the assay.

The assays were carried out in polystyrene 96-well U bottom plates (Costar). The 96-well plates were pre-blocked with casein blocking buffer (Thermo Fisher 37528) and then washed three times with (HBSS+/+) (Life Technologies 14025-050) prior to assay. *P. aeruginosa* (ATCC BAA-47 and ATCC 27853) were grown in LB broth (Fisher BP1426-500) to late exponential growth phase. Subsequently, the bacteria were centrifuged at 10 000 rpm for 5 minutes and resuspended in HBSS+/+ at a bacterial density of $2 \times 10^9$ CFU/mL. Baclight Red bacterial stain (Thermo Fisher B-35001) was added to the bacteria to a final concentration of 1 µM, the bacteria were incubated at room temperature in the dark for 10 minutes, washed and resuspended in HBSS+/+. Bacteria ($1 \times 10^8$ CFU) were then incubated with various concentrations of test compound or buffer alone, at room temperature, shaking at 450 rpm for 1 hour. The bacteria were washed with $3 \times 200$ µL HBSS+/+(centrifuged at 4000 rpm, 5 minutes). Alpha-galactosyl IgM antibody (Absolute Ab) was added (1.12 µg in 50 ul HBSS+/+) to the bacteria and incubated at room temp shaking at 450 rpm for 1 hour in the dark. The bacteria were washed with $3 \times 200$ µL HBSS+/+(centrifuged at 4000 rpm, 5 minutes). A secondary anti-IgM-FITC Ab (Biolegend 314506) was added (1 µg in 100 ul HBSS+/+) to the bacteria and incubated at room temp shaking at 450 rpm for 1 hour in the dark. The bacteria were washed with $3 \times 200$ µL HBSS+/+(centrifuged at 4000 rpm, 5 minutes) and finally resuspended in 200 µL HBSS+/+ and evaluated on a FC500 (Beckman Coulter). Data from all samples were analysed in the Kaluza software package (Beckman Coulter). Samples were run in duplicates.

Table 5 demonstrates that no recruitment of alpha-galactosyl IgM antibody to *P. aeruginosa* (ATCC BAA-47 and ATCC 27853) is observed with Example 8 and Example 9 using the flow cytometry assay described above. The fold shift over background was calculated by dividing the Mean Fluorescence Intensity (MFI) obtained in the presence of 20 µM compound by the Mean Fluorescence Intensity (MFI) obtained in the absence of compound. This data demonstrates that Examples 8 and 9 did not show the expected level of recruitment of anti-galactosyl antibodies to bacteria expected from the good levels of aptamer affinity reported in FIG. 6.

TABLE 5

| Compound | Fold Shift for IgM recruitment at 20 µM alphamer |
|---|---|
| Example 8 | 1.1 (*P. aeruginosa* ATCC BAA-47) |
| Example 8 | 1.1 (*P. aeruginosa* ATCC 27853) |
| Example 9 | 1.0 (*P. aeruginosa* ATCC BAA-47) |
| Example 9 | 1.0 (*P. aeruginosa* ATCC 27853) |

The invention claimed is:

1. A compound of formula (I) or a pharmaceutically acceptable salt thereof:

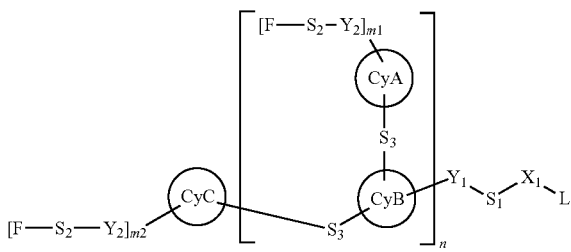

(I)

wherein:

L represents a binding moiety selected from a nucleic acid aptamer;

S1 represents a spacer selected from a (CH2)a- or (CH2)b-(CH2-CH2-O)c- (CH2)d- group, wherein one to five of said —CH2- groups may optionally be substituted by one or more groups selected from —O—, —C(O)NH— and —NHC(O)— and phenyl;

a represents an integer selected from 1 to 35;
b represents an integer selected from 0 to 5;
c represents an integer selected from 1 to 20;
d represents an integer selected from 1 to 20;

S2 represents a spacer selected from a —(CH2)e- or —(CH2)f-(CH2-CH2-O)g- (CH2)h- group, wherein one to three of said —CH2- groups may optionally be substituted by one or more groups selected from —N(H)—, —C(O)NH— and —NHC(O)—;

e represents an integer selected from 1 to 15;
f represents an integer selected from 1 to 10;
g represents an integer selected from 1 to 20;
h represents an integer selected from 1 to 5;

S3 represents a spacer selected from a —(CH2)q- or —(CH2)r-(CH2-CH2-O)s- (CH2)t- group, wherein one to ten of said —CH2- groups may optionally be substituted by one or more groups selected from —N(H)—, —C(O)NH—, —NHC(O)— and —O—;

q represents an integer selected from 1 to 25;
r represents an integer selected from 1 to 10;
s represents an integer selected from 1 to 20;
t represents an integer selected from 1 to 10;

X1 represents —O—;

Y1 and Y2 independently represent a bond, —O—, —S—, —NH—, —NHC(O)—, —C(O)NH—, —OC(O)—, —C(O)O—, —SC(O)—, —C(O)S—, —NHSO2-, —SO2NH— or —NHC(O)NH— group;

F represents a carbohydrate molecule capable of binding to a human anti-alpha-galactosyl antibody;

m1 and m2 independently represent an integer selected from 1 to 5;

n represents an integer selected from 1 or 2; and

CyA, CyB and CyC independently represent biphenyl or triphenyl.

2. The compound as defined in claim 1 or a pharmaceutically acceptable salt thereof, wherein S1 represents a spacer selected from:

—(CH2)2-, —CH2-CONH—(CH2)2-, —CH2-NHCO—(CH2)4-CONH—(CH2)2-, —(CH2)6-, —(CH2)5-CONH—(CH2)5-CONH—(CH2)6-, —(CH2)5-CONH—(CH2)5-CONH—(CH2)5-CONH—(CH2)5-CONH— (CH2)6-),

—(CH2)2-NHCO—(CH2CH2O)12-(CH2)2-, —(CH2)2-NHCO—(CH2CH2O)4-(CH2)2-NHCO—CH2-O-phenyl-CONH—(CH2)6-, —(CH2)2-NHCO—(CH2CH2O)12-(CH2)2-NHCO—CH2-O-phenyl-CONH—(CH2)6-, or —(CH2CH2O)4-(CH2)2-CONH—(CH2)2-).

3. The compound as defined in claim 1 or a pharmaceutically acceptable salt thereof, wherein a represents an integer selected from: 1 to 30; and/or wherein b represents an integer selected from 0 to 3 and/or wherein c represents an integer selected from 1 to 15; and/or wherein d represents an integer selected from 1 to 15.

4. The compound as defined claim 1 or a pharmaceutically acceptable salt thereof, wherein $Y_1$ represents a bond, —C(O)NH— or —O—.

5. The compound as defined claim 1 or a pharmaceutically acceptable salt thereof, wherein $S_2$ represents a spacer selected from:

—$(CH_2)_3$—NHCO—$CH_2$—, —$(CH_2)_3$—, —$(CH_2)_3$—NHCO—$(CH_2)_4$—CONH—$CH_2$—, —$(CH_2)_3$—NH—$CH_2$—, —$(CH_2)_3$—NHCO—$(CH_2)_3$—NHCO—$CH_2$—)

—$(CH_2)_3$—NHCO—$(CH_2CH_2O)_4$—$(CH_2)_2$—NHCO—$CH_2$—, —$(CH_2)_3$—NHCO—$(CH_2CH_2O)_{12}$—$(CH_2)_2$—NHCO—$CH_2$—, or —$(CH_2)_3$—NHCO—$(CH_2)_3$—NHCO—$(CH_2CH_2O)_4$—$(CH_2)_2$—NHCO—$CH_2$—).

6. The compound as defined claim 1 or a pharmaceutically acceptable salt thereof, wherein e represents an integer selected from 1 to 10; and/or wherein f represents an integer selected from 1 to 8; and/or wherein g represents an integer selected from 1 to 15; and/or wherein h represents an integer selected from 1 to 4.

7. The compound as defined in claim 1 or a pharmaceutically acceptable salt thereof, wherein $Y_2$ represents a bond, —O— or —NHC(O)—.

8. The compound as defined in claim 1 or a pharmaceutically acceptable salt thereof, wherein $S_3$ represents a spacer selected from:
—CONH—$(CH_2)_2$—NHCO—$CH_2$—O—, —CONH—$(CH_2)_5$—CONH—$(CH_2)_5$—CONH—$(CH_2)_2$—NHCO—$CH_2$—O—), or
—CONH—$(CH_2)_2$—NHCO—$(CH_2CH_2O)_4$—$(CH_2)_2$—NHCO—$CH_2$—O—).

9. The compound as defined in claim 1 or a pharmaceutically acceptable salt thereof, wherein q represents an integer selected from 1 to 20; and/or
wherein r represents an integer selected from 1 to 8; and/or
wherein s represents an integer selected from 1 to 15; and/or
wherein t represents an integer selected from 1 to 5; and/or
wherein m1 represents an integer selected from 1 to 4; and/or
wherein m2 represents an integer selected from 1 to 4; and/or
wherein n represents an integer selected from 1.

10. The compound as defined in claim 1 or a pharmaceutically acceptable salt thereof, wherein CyA, CyB and CyC each represent biphenyl; or CyA and CyC both represent triphenyl and CyB represents biphenyl; or CyA and CyB both represent biphenyl and CyC represents triphenyl; or CyA and CyB both represent triphenyl and CyC represents biphenyl.

11. A compound of formula (I)a or a pharmaceutically acceptable salt thereof:

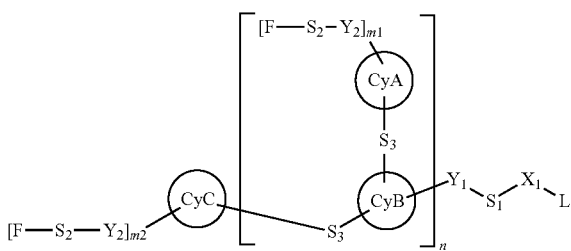

wherein:
L represents a binding moiety selected from a nucleic acid aptamer;
$S_1$ represents a spacer selected from a —$(CH_2)_a$— group;
a represents an integer selected from 6;
$S_2$ represents a spacer selected from a —$(CH_2)_e$— or —$(CH_2)_f$—$(CH_2$—$CH_2$—$O)_g$—$(CH_2)_h$— group, wherein one or two of said —$CH_2$— groups may optionally be substituted by one or two —NHC(O)— groups;
e represents an integer selected from 5;
f represents an integer selected from 4;
g represents an integer selected from 4;
h represents an integer selected from 4;
$S_3$ represents a spacer selected from a —$(CH_2)_q$— or —$(CH_2)_r$—$(CH_2$—$CH_2$—$O)_s$—$(CH_2)_t$— group, wherein one to five of said —$CH_2$— groups may optionally be substituted by one to five groups selected from —C(O)NH—, —NHC(O)— and —O—;
q represents an integer selected from 6 or 18;
r represents an integer selected from 4;
s represents an integer selected from 4;
t represents an integer selected from 5;
$X_1$ represents —O—;
$Y_1$ and $Y_2$ independently represent a —O— or —C(O)NH— group;
F represents a carbohydrate molecule capable of binding to a human anti-alpha-galactosyl antibody;
m1 and m2 independently represent an integer selected from 1 to 4;
n represents an integer selected from 1; and
CyA, CyB and CyC independently represent biphenyl or triphenyl.

12. The compound as defined in claim 1 or a pharmaceutically acceptable salt thereof, wherein F is selected from galactosyl-alpha-1,3-galactosyl-beta-1,4-N-acetylglucosamine, alpha1-3 galactobiose, alpha1-3-beta1-4-galactotriose or galilipentasaccharide.

13. The compound as defined in claim 1, wherein the nucleic acid aptamer is an EGFR binding nucleic acid aptamer selected from the nucleic acid aptamer of SEQ ID NO: 1.

14. The compound as defined in claim 1, wherein the nucleic acid aptamer is a PSMA binding nucleic acid nucleic acid aptamer selected from the nucleic acid aptamer of SEQ ID NO: 2.

15. The compound as defined in claim 1 or a pharmaceutically acceptable salt thereof, which is selected from any one of Examples 1-9.

16. A pharmaceutical composition comprising a compound as defined claim 1 or a pharmaceutically acceptable salt thereof.

17. A method of treating cancer which comprises administering to an individual in need thereof a compound as defined in claim 13 or a pharmaceutically acceptable salt thereof, for use in the treatment of cancer.

18. A method of treating a disease or disorder mediated by PSMA which comprises administering to an individual in need thereof a compound as defined in claim 14 or a pharmaceutically acceptable salt thereof.

19. A process for preparing a compound of formula (I) as defined in claim 1 which comprises:
(a) preparing a compound of formula (I) wherein $Y_1$ represents —CONH— (i.e. a compound of formula (IA)) by reacting a compound of formula (II) with a compound of formula (III):

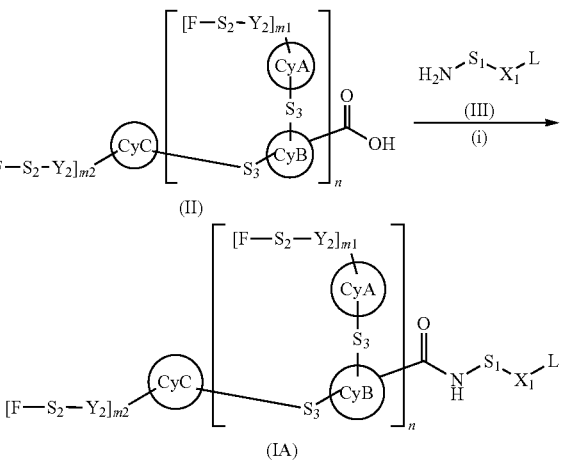

wherein $S_2$, $S_3$, $Y_2$, m1, m2, n, CyA, CyB, CyC, $S_1$, $X_1$, L and F are as defined in claim 1; and/or
(b) interconversion of a compound of formula (I) or protected derivative thereof to a further compound of formula (I) or protected derivative thereof.

20. A compound of formula (II):

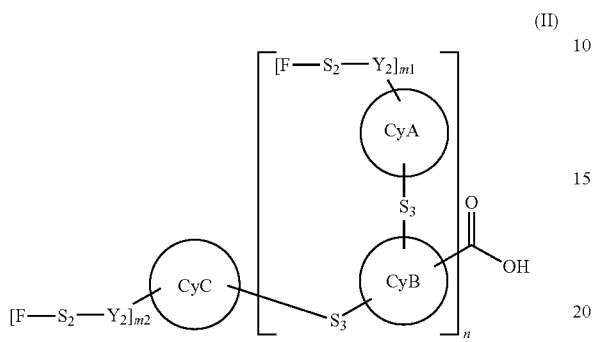

(II)

wherein
- S2 represents a spacer selected from a —(CH2)e- or —(CH2)f-(CH2-CH2-O)g- (CH2)h- group, wherein one to three of said —CH2- groups may optionally be substituted by one or more groups selected from —N(H)—, —C(O)NH— and —NHC(O)—;
- e represents an integer selected from 1 to 15;
- f represents an integer selected from 1 to 10;
- g represents an integer selected from 1 to 20;
- h represents an integer selected from 1 to 5;
- S3 represents a spacer selected from a —(CH2)q- or —(CH2)r-(CH2-CH2-O)s- (CH2)t- group, wherein one to ten of said —CH2- groups may optionally be substituted by one or more groups selected from —N(H)—, —C(O)NH—, —NHC(O)— and —O—;
- q represents an integer selected from 1 to 25;
- r represents an integer selected from 1 to 10;
- s represents an integer selected from 1 to 20;
- t represents an integer selected from 1 to 10;
- Y2 represents a bond, —O—, —S—, —NH—, —NHC(O)—, —C(O)NH—, —OC(O)—, —C(O)O—, —SC(O)—, —C(O)S—, —NHSO2-, —SO2NH— or —NHC(O)NH— group;
- m1 and m2 independently represent an integer selected from 1 to 5;
- n represents an integer selected from 1 or 2;
- CyA, CyB and CyC independently represent biphenyl or triphenyl; and
- F represents a carbohydrate molecule capable of binding to a human anti-alpha-galactosyl antibody or a compound of formula (VII):

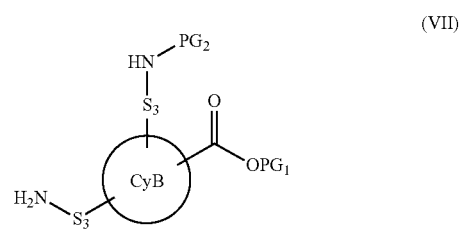

(VII)

wherein
- CyB represents biphenyl or triphenyl;
- S3 represents a spacer selected from a —(CH2)q- or —(CH2)r-(CH2-CH2-O)s- (CH2)t- group, wherein one to ten of said —CH2- groups may optionally be substituted by one or more groups selected from —N(H)—, —C(O)NH—, —NHC(O)— and —O—;
- q represents an integer selected from 1 to 25;
- r represents an integer selected from 1 to 10;
- s represents an integer selected from 1 to 20;
- t represents an integer selected from 1 to 10;
- $PG_1$ is a protecting group comprising benzyl; and
- $PG_2$ is a protecting group comprising monomethoxytrityl (MMTr).

* * * * *

SEQUENCE LISTING

<160> NUMBER OF SEQ ID NOS: 37

<210> SEQ ID NO 1
<211> LENGTH: 43
<212> TYPE: RNA
<213> ORGANISM: Artificial
<220> FEATURE:
<223> OTHER INFORMATION: Synthetic Aptamer
<220> FEATURE:
<221> NAME/KEY: misc_feature

```
<222> LOCATION: (1)..(4)
<223> OTHER INFORMATION: 2'OMe substituted nucleotide
<220> FEATURE:
<221> NAME/KEY: misc_feature
<222> LOCATION: (5)..(7)
<223> OTHER INFORMATION: 2'-F substituted nucleotide
<220> FEATURE:
<221> NAME/KEY: misc_feature
<222> LOCATION: (10)..(11)
<223> OTHER INFORMATION: 2'-F substituted nucleotide
<220> FEATURE:
<221> NAME/KEY: misc_feature
<222> LOCATION: (12)..(12)
<223> OTHER INFORMATION: 2'OMe substituted nucleotide
<220> FEATURE:
<221> NAME/KEY: misc_feature
<222> LOCATION: (13)..(14)
<223> OTHER INFORMATION: 2'-F substituted nucleotide
<220> FEATURE:
<221> NAME/KEY: misc_feature
<222> LOCATION: (15)..(15)
<223> OTHER INFORMATION: 2'OMe substituted nucleotide
<220> FEATURE:
<221> NAME/KEY: misc_feature
<222> LOCATION: (16)..(16)
<223> OTHER INFORMATION: 2'-F substituted nucleotide
<220> FEATURE:
<221> NAME/KEY: misc_feature
<222> LOCATION: (17)..(18)
<223> OTHER INFORMATION: 2'OMe substituted nucleotide
<220> FEATURE:
<221> NAME/KEY: misc_feature
<222> LOCATION: (20)..(21)
<223> OTHER INFORMATION: 2'OMe substituted nucleotide
<220> FEATURE:
<221> NAME/KEY: misc_feature
<222> LOCATION: (23)..(23)
<223> OTHER INFORMATION: 2'OMe substituted nucleotide
<220> FEATURE:
<221> NAME/KEY: misc_feature
<222> LOCATION: (24)..(24)
<223> OTHER INFORMATION: 2'-F substituted nucleotide
<220> FEATURE:
<221> NAME/KEY: misc_feature
<222> LOCATION: (25)..(25)
<223> OTHER INFORMATION: 2'OMe substituted nucleotide
<220> FEATURE:
<221> NAME/KEY: misc_feature
<222> LOCATION: (26)..(26)
<223> OTHER INFORMATION: 2'-F substituted nucleotide
<220> FEATURE:
<221> NAME/KEY: misc_feature
<222> LOCATION: (27)..(27)
<223> OTHER INFORMATION: 2'OMe substituted nucleotide
<220> FEATURE:
<221> NAME/KEY: misc_feature
<222> LOCATION: (28)..(29)
<223> OTHER INFORMATION: 2'-F substituted nucleotide
<220> FEATURE:
<221> NAME/KEY: misc_feature
<222> LOCATION: (30)..(30)
<223> OTHER INFORMATION: 2'OMe substituted nucleotide
<220> FEATURE:
<221> NAME/KEY: misc_feature
<222> LOCATION: (33)..(33)
<223> OTHER INFORMATION: 2'OMe substituted nucleotide
<220> FEATURE:
<221> NAME/KEY: misc_feature
<222> LOCATION: (34)..(35)
<223> OTHER INFORMATION: 2'-F substituted nucleotide
<220> FEATURE:
<221> NAME/KEY: misc_feature
<222> LOCATION: (36)..(38)
<223> OTHER INFORMATION: 2'OMe substituted nucleotide
<220> FEATURE:
<221> NAME/KEY: misc_feature
<222> LOCATION: (40)..(42)
<223> OTHER INFORMATION: 2'-F substituted nucleotide
<220> FEATURE:
```

-continued

```
<221> NAME/KEY: misc_feature
<222> LOCATION: (43)..(43)
<223> OTHER INFORMATION: idT

<400> SEQUENCE: 1
gggauuuaau cgccguagaa aagcauguca aagccggaac ccn            43

<210> SEQ ID NO 2
<211> LENGTH: 44
<212> TYPE: RNA
<213> ORGANISM: Artificial
<220> FEATURE:
<223> OTHER INFORMATION: Synthetic Aptamer
<220> FEATURE:
<221> NAME/KEY: misc_feature
<222> LOCATION: (5)..(6)
<223> OTHER INFORMATION: modified 2'-fluoro nucleotide
<220> FEATURE:
<221> NAME/KEY: misc_feature
<222> LOCATION: (15)..(17)
<223> OTHER INFORMATION: modified 2'-fluoro nucleotide
<220> FEATURE:
<221> NAME/KEY: misc_feature
<222> LOCATION: (20)..(24)
<223> OTHER INFORMATION: modified 2'-fluoro nucleotide
<220> FEATURE:
<221> NAME/KEY: misc_feature
<222> LOCATION: (26)..(26)
<223> OTHER INFORMATION: modified 2'-fluoro nucleotide
<220> FEATURE:
<221> NAME/KEY: misc_feature
<222> LOCATION: (28)..(29)
<223> OTHER INFORMATION: modified 2'-fluoro nucleotide
<220> FEATURE:
<221> NAME/KEY: misc_feature
<222> LOCATION: (33)..(35)
<223> OTHER INFORMATION: modified 2'-fluoro nucleotide
<220> FEATURE:
<221> NAME/KEY: misc_feature
<222> LOCATION: (37)..(37)
<223> OTHER INFORMATION: modified 2'-fluoro nucleotide
<220> FEATURE:
<221> NAME/KEY: misc_feature
<222> LOCATION: (39)..(43)
<223> OTHER INFORMATION: modified 2'-fluoro nucleotide
<220> FEATURE:
<221> NAME/KEY: misc_feature
<222> LOCATION: (44)..(44)
<223> OTHER INFORMATION: idT

<400> SEQUENCE: 2
gggaccgaaa aagaccugac uucuauacua agucuacguu cccn           44

<210> SEQ ID NO 3
<211> LENGTH: 56
<212> TYPE: RNA
<213> ORGANISM: Artificial
<220> FEATURE:
<223> OTHER INFORMATION: Synthetic Aptamer
<220> FEATURE:
<221> NAME/KEY: misc_feature
<222> LOCATION: (1)..(1)
<223> OTHER INFORMATION: modified 2'-fluoro nucleotide
<220> FEATURE:
<221> NAME/KEY: misc_feature
<222> LOCATION: (2)..(2)
<223> OTHER INFORMATION: modified 2'-methoxy nucleotide
<220> FEATURE:
<221> NAME/KEY: misc_feature
<222> LOCATION: (3)..(3)
<223> OTHER INFORMATION: modified 2'-fluoro nucleotide
<220> FEATURE:
<221> NAME/KEY: misc_feature
<222> LOCATION: (4)..(5)
<223> OTHER INFORMATION: modified 2'-methoxy nucleotide
```

```
<220> FEATURE:
<221> NAME/KEY: misc_feature
<222> LOCATION: (6)..(6)
<223> OTHER INFORMATION: modified 2'-fluoro nucleotide
<220> FEATURE:
<221> NAME/KEY: misc_feature
<222> LOCATION: (7)..(10)
<223> OTHER INFORMATION: modified 2'-methoxy nucleotide
<220> FEATURE:
<221> NAME/KEY: misc_feature
<222> LOCATION: (11)..(13)
<223> OTHER INFORMATION: modified 2'-fluoro nucleotide
<220> FEATURE:
<221> NAME/KEY: misc_feature
<222> LOCATION: (14)..(19)
<223> OTHER INFORMATION: modified 2'-methoxy nucleotide
<220> FEATURE:
<221> NAME/KEY: misc_feature
<222> LOCATION: (20)..(22)
<223> OTHER INFORMATION: modified 2'-fluoro nucleotide
<220> FEATURE:
<221> NAME/KEY: misc_feature
<222> LOCATION: (23)..(24)
<223> OTHER INFORMATION: modified 2'-methoxy nucleotide
<220> FEATURE:
<221> NAME/KEY: misc_feature
<222> LOCATION: (25)..(25)
<223> OTHER INFORMATION: modified 2'-fluoro nucleotide
<220> FEATURE:
<221> NAME/KEY: misc_feature
<222> LOCATION: (26)..(26)
<223> OTHER INFORMATION: modified 2'-methoxy nucleotide
<220> FEATURE:
<221> NAME/KEY: misc_feature
<222> LOCATION: (27)..(28)
<223> OTHER INFORMATION: modified 2'-fluoro nucleotide
<220> FEATURE:
<221> NAME/KEY: misc_feature
<222> LOCATION: (29)..(29)
<223> OTHER INFORMATION: modified 2'-methoxy nucleotide
<220> FEATURE:
<221> NAME/KEY: misc_feature
<222> LOCATION: (30)..(32)
<223> OTHER INFORMATION: modified 2'-fluoro nucleotide
<220> FEATURE:
<221> NAME/KEY: misc_feature
<222> LOCATION: (33)..(36)
<223> OTHER INFORMATION: modified 2'-methoxy nucleotide
<220> FEATURE:
<221> NAME/KEY: misc_feature
<222> LOCATION: (37)..(39)
<223> OTHER INFORMATION: modified 2'-fluoro nucleotide
<220> FEATURE:
<221> NAME/KEY: misc_feature
<222> LOCATION: (40)..(47)
<223> OTHER INFORMATION: modified 2'-methoxy nucleotide
<220> FEATURE:
<221> NAME/KEY: misc_feature
<222> LOCATION: (48)..(48)
<223> OTHER INFORMATION: modified 2'-fluoro nucleotide
<220> FEATURE:
<221> NAME/KEY: misc_feature
<222> LOCATION: (49)..(53)
<223> OTHER INFORMATION: modified 2'-methoxy nucleotide
<220> FEATURE:
<221> NAME/KEY: misc_feature
<222> LOCATION: (54)..(54)
<223> OTHER INFORMATION: modified 2'-fluoro nucleotide
<220> FEATURE:
<221> NAME/KEY: misc_feature
<222> LOCATION: (55)..(55)
<223> OTHER INFORMATION: modified 2'-methoxy nucleotide
<220> FEATURE:
<221> NAME/KEY: misc_feature
<222> LOCATION: (56)..(56)
<223> OTHER INFORMATION: idT

<400> SEQUENCE: 3
```
gugcagaucc gggauauaaug gguaguggag gguuucgggc uauaccagau cuugun     56

```
<210> SEQ ID NO 4
<211> LENGTH: 56
<212> TYPE: RNA
<213> ORGANISM: Artificial
<220> FEATURE:
<223> OTHER INFORMATION: Synthetic Aptamer
<220> FEATURE:
<221> NAME/KEY: misc_feature
<222> LOCATION: (1)..(1)
<223> OTHER INFORMATION: modified 2'-fluoro nucleotide
<220> FEATURE:
<221> NAME/KEY: misc_feature
<222> LOCATION: (2)..(2)
<223> OTHER INFORMATION: modified 2'-methoxy nucleotide
<220> FEATURE:
<221> NAME/KEY: misc_feature
<222> LOCATION: (3)..(3)
<223> OTHER INFORMATION: modified 2'-fluoro nucleotide
<220> FEATURE:
<221> NAME/KEY: misc_feature
<222> LOCATION: (3)..(3)
<223> OTHER INFORMATION: modified 2'-fluoro nucleotide
<220> FEATURE:
<221> NAME/KEY: misc_feature
<222> LOCATION: (4)..(5)
<223> OTHER INFORMATION: modified 2'-methoxy nucleotide
<220> FEATURE:
<221> NAME/KEY: misc_feature
<222> LOCATION: (6)..(6)
<223> OTHER INFORMATION: modified 2'-fluoro nucleotide
<220> FEATURE:
<221> NAME/KEY: misc_feature
<222> LOCATION: (7)..(9)
<223> OTHER INFORMATION: modified 2'-methoxy nucleotide
<220> FEATURE:
<221> NAME/KEY: misc_feature
<222> LOCATION: (10)..(11)
<223> OTHER INFORMATION: modified 2'-fluoro nucleotide
<220> FEATURE:
<221> NAME/KEY: misc_feature
<222> LOCATION: (12)..(15)
<223> OTHER INFORMATION: modified 2'-methoxy nucleotide
<220> FEATURE:
<221> NAME/KEY: misc_feature
<222> LOCATION: (16)..(18)
<223> OTHER INFORMATION: modified 2'-fluoro nucleotide
<220> FEATURE:
<221> NAME/KEY: misc_feature
<222> LOCATION: (19)..(20)
<223> OTHER INFORMATION: modified 2'-methoxy nucleotide
<220> FEATURE:
<221> NAME/KEY: misc_feature
<222> LOCATION: (21)..(21)
<223> OTHER INFORMATION: modified 2'-fluoro nucleotide
<220> FEATURE:
<221> NAME/KEY: misc_feature
<222> LOCATION: (22)..(22)
<223> OTHER INFORMATION: modified 2'-methoxy nucleotide
<220> FEATURE:
<221> NAME/KEY: misc_feature
<222> LOCATION: (23)..(24)
<223> OTHER INFORMATION: modified 2'-fluoro nucleotide
<220> FEATURE:
<221> NAME/KEY: misc_feature
<222> LOCATION: (25)..(28)
<223> OTHER INFORMATION: modified 2'-methoxy nucleotide
<220> FEATURE:
<221> NAME/KEY: misc_feature
<222> LOCATION: (29)..(31)
<223> OTHER INFORMATION: modified 2'-fluoro nucleotide
<220> FEATURE:
<221> NAME/KEY: misc_feature
<222> LOCATION: (32)..(33)
<223> OTHER INFORMATION: modified 2'-methoxy nucleotide
<220> FEATURE:
<221> NAME/KEY: misc_feature
```

-continued

```
<222> LOCATION: (34)..(36)
<223> OTHER INFORMATION: modified 2'-fluoro nucleotide
<220> FEATURE:
<221> NAME/KEY: misc_feature
<222> LOCATION: (37)..(40)
<223> OTHER INFORMATION: modified 2'-methoxy nucleotide
<220> FEATURE:
<221> NAME/KEY: misc_feature
<222> LOCATION: (41)..(43)
<223> OTHER INFORMATION: modified 2'-fluoro nucleotide
<220> FEATURE:
<221> NAME/KEY: misc_feature
<222> LOCATION: (44)..(53)
<223> OTHER INFORMATION: modified 2'-methoxy nucleotide
<220> FEATURE:
<221> NAME/KEY: misc_feature
<222> LOCATION: (54)..(54)
<223> OTHER INFORMATION: modified 2'-fluoro nucleotide
<220> FEATURE:
<221> NAME/KEY: misc_feature
<222> LOCATION: (55)..(55)
<223> OTHER INFORMATION: modified 2'-methoxy nucleotide
<220> FEATURE:
<221> NAME/KEY: misc_feature
<222> LOCATION: (56)..(56)
<223> OTHER INFORMATION: idT

<400> SEQUENCE: 4
gugcagauug gaaaagggua guggauuugg gaagggguuua ggguuucaau cuugun      56

<210> SEQ ID NO 5
<211> LENGTH: 48
<212> TYPE: RNA
<213> ORGANISM: Artificial
<220> FEATURE:
<223> OTHER INFORMATION: Synthetic Aptamer
<220> FEATURE:
<221> NAME/KEY: misc_feature
<222> LOCATION: (4)..(4)
<223> OTHER INFORMATION: modified 2'-fluoro nucleotide
<220> FEATURE:
<221> NAME/KEY: misc_feature
<222> LOCATION: (8)..(10)
<223> OTHER INFORMATION: modified 2'-fluoro nucleotide
<220> FEATURE:
<221> NAME/KEY: misc_feature
<222> LOCATION: (13)..(14)
<223> OTHER INFORMATION: modified 2'-fluoro nucleotide
<220> FEATURE:
<221> NAME/KEY: misc_feature
<222> LOCATION: (16)..(17)
<223> OTHER INFORMATION: modified 2'-fluoro nucleotide
<220> FEATURE:
<221> NAME/KEY: misc_feature
<222> LOCATION: (19)..(19)
<223> OTHER INFORMATION: modified 2'-fluoro nucleotide
<220> FEATURE:
<221> NAME/KEY: misc_feature
<222> LOCATION: (27)..(27)
<223> OTHER INFORMATION: modified 2'-fluoro nucleotide
<220> FEATURE:
<221> NAME/KEY: misc_feature
<222> LOCATION: (29)..(29)
<223> OTHER INFORMATION: modified 2'-fluoro nucleotide
<220> FEATURE:
<221> NAME/KEY: misc_feature
<222> LOCATION: (31)..(32)
<223> OTHER INFORMATION: modified 2'-fluoro nucleotide
<220> FEATURE:
<221> NAME/KEY: misc_feature
<222> LOCATION: (37)..(38)
<223> OTHER INFORMATION: modified 2'-fluoro nucleotide
<220> FEATURE:
<221> NAME/KEY: misc_feature
<222> LOCATION: (43)..(44)
<223> OTHER INFORMATION: modified 2'-fluoro nucleotide
<220> FEATURE:
```

```
<221> NAME/KEY: misc_feature
<222> LOCATION: (46)..(48)
<223> OTHER INFORMATION: modified 2'-fluoro nucleotide

<400> SEQUENCE: 5
ggacggauuu aaucgccgua gaaaagcaug ucaaagccgg aaccgucc            48

<210> SEQ ID NO 6
<211> LENGTH: 42
<212> TYPE: RNA
<213> ORGANISM: Artificial
<220> FEATURE:
<223> OTHER INFORMATION: Synthetic Aptamer
<220> FEATURE:
<221> NAME/KEY: misc_feature
<222> LOCATION: (1)..(4)
<223> OTHER INFORMATION: modified 2'-methoxy nucleotide
<220> FEATURE:
<221> NAME/KEY: misc_feature
<222> LOCATION: (5)..(7)
<223> OTHER INFORMATION: modified 2'-fluoro nucleotide
<220> FEATURE:
<221> NAME/KEY: misc_feature
<222> LOCATION: (10)..(11)
<223> OTHER INFORMATION: modified 2'-fluoro nucleotide
<220> FEATURE:
<221> NAME/KEY: misc_feature
<222> LOCATION: (12)..(12)
<223> OTHER INFORMATION: modified 2'-methoxy nucleotide
<220> FEATURE:
<221> NAME/KEY: misc_feature
<222> LOCATION: (13)..(14)
<223> OTHER INFORMATION: modified 2'-fluoro nucleotide
<220> FEATURE:
<221> NAME/KEY: misc_feature
<222> LOCATION: (15)..(15)
<223> OTHER INFORMATION: modified 2'-methoxy nucleotide
<220> FEATURE:
<221> NAME/KEY: misc_feature
<222> LOCATION: (16)..(16)
<223> OTHER INFORMATION: modified 2'-fluoro nucleotide
<220> FEATURE:
<221> NAME/KEY: misc_feature
<222> LOCATION: (17)..(18)
<223> OTHER INFORMATION: modified 2'-methoxy nucleotide
<220> FEATURE:
<221> NAME/KEY: misc_feature
<222> LOCATION: (20)..(21)
<223> OTHER INFORMATION: modified 2'-methoxy nucleotide
<220> FEATURE:
<221> NAME/KEY: misc_feature
<222> LOCATION: (23)..(23)
<223> OTHER INFORMATION: modified 2'-methoxy nucleotide
<220> FEATURE:
<221> NAME/KEY: misc_feature
<222> LOCATION: (24)..(24)
<223> OTHER INFORMATION: modified 2'-fluoro nucleotide
<220> FEATURE:
<221> NAME/KEY: misc_feature
<222> LOCATION: (25)..(25)
<223> OTHER INFORMATION: modified 2'-methoxy nucleotide
<220> FEATURE:
<221> NAME/KEY: misc_feature
<222> LOCATION: (26)..(26)
<223> OTHER INFORMATION: modified 2'-fluoro nucleotide
<220> FEATURE:
<221> NAME/KEY: misc_feature
<222> LOCATION: (27)..(27)
<223> OTHER INFORMATION: modified 2'-methoxy nucleotide
<220> FEATURE:
<221> NAME/KEY: misc_feature
<222> LOCATION: (28)..(29)
<223> OTHER INFORMATION: modified 2'-fluoro nucleotide
<220> FEATURE:
<221> NAME/KEY: misc_feature
<222> LOCATION: (30)..(30)
<223> OTHER INFORMATION: modified 2'-methoxy nucleotide
```

<220> FEATURE:
<221> NAME/KEY: misc_feature
<222> LOCATION: (33)..(33)
<223> OTHER INFORMATION: modified 2'-methoxy nucleotide
<220> FEATURE:
<221> NAME/KEY: misc_feature
<222> LOCATION: (34)..(35)
<223> OTHER INFORMATION: modified 2'-fluoro nucleotide
<220> FEATURE:
<221> NAME/KEY: misc_feature
<222> LOCATION: (36)..(38)
<223> OTHER INFORMATION: modified 2'-methoxy nucleotide
<220> FEATURE:
<221> NAME/KEY: misc_feature
<222> LOCATION: (40)..(42)
<223> OTHER INFORMATION: modified 2'-fluoro nucleotide

<400> SEQUENCE: 6
gggauuuaau cgccguagaa aagcauguca aagccggaac cc       42

<210> SEQ ID NO 7
<211> LENGTH: 43
<212> TYPE: RNA
<213> ORGANISM: Artificial
<220> FEATURE:
<223> OTHER INFORMATION: Synthetic Aptamer
<220> FEATURE:
<221> NAME/KEY: misc_feature
<222> LOCATION: (5)..(6)
<223> OTHER INFORMATION: modified 2'-fluoro nucleotide
<220> FEATURE:
<221> NAME/KEY: misc_feature
<222> LOCATION: (15)..(17)
<223> OTHER INFORMATION: modified 2'-fluoro nucleotide
<220> FEATURE:
<221> NAME/KEY: misc_feature
<222> LOCATION: (20)..(24)
<223> OTHER INFORMATION: modified 2'-fluoro nucleotide
<220> FEATURE:
<221> NAME/KEY: misc_feature
<222> LOCATION: (26)..(26)
<223> OTHER INFORMATION: modified 2'-fluoro nucleotide
<220> FEATURE:
<221> NAME/KEY: misc_feature
<222> LOCATION: (28)..(29)
<223> OTHER INFORMATION: modified 2'-fluoro nucleotide
<220> FEATURE:
<221> NAME/KEY: misc_feature
<222> LOCATION: (33)..(35)
<223> OTHER INFORMATION: modified 2'-fluoro nucleotide
<220> FEATURE:
<221> NAME/KEY: misc_feature
<222> LOCATION: (37)..(37)
<223> OTHER INFORMATION: modified 2'-fluoro nucleotide
<220> FEATURE:
<221> NAME/KEY: misc_feature
<222> LOCATION: (39)..(43)
<223> OTHER INFORMATION: modified 2'-fluoro nucleotide

<400> SEQUENCE: 7
gggaccgaaa aagaccugac uucuauacua agucuacguu ccc       43

<210> SEQ ID NO 8
<211> LENGTH: 43
<212> TYPE: RNA
<213> ORGANISM: Artificial
<220> FEATURE:
<223> OTHER INFORMATION: Synthetic Aptamer
<220> FEATURE:
<221> NAME/KEY: misc_feature
<222> LOCATION: (1)..(4)
<223> OTHER INFORMATION: modified 2'-methoxy nucleotide
<220> FEATURE:
<221> NAME/KEY: misc_feature
<222> LOCATION: (5)..(6)

```
<223> OTHER INFORMATION: modified 2'-fluoro nucleotide
<220> FEATURE:
<221> NAME/KEY: misc_feature
<222> LOCATION: (7)..(7)
<223> OTHER INFORMATION: modified 2'-methoxy nucleotide
<220> FEATURE:
<221> NAME/KEY: misc_feature
<222> LOCATION: (12)..(15)
<223> OTHER INFORMATION: modified 2'-methoxy nucleotide
<220> FEATURE:
<221> NAME/KEY: misc_feature
<222> LOCATION: (16)..(17)
<223> OTHER INFORMATION: modified 2'-fluoro nucleotide
<220> FEATURE:
<221> NAME/KEY: misc_feature
<222> LOCATION: (20)..(24)
<223> OTHER INFORMATION: modified 2'-fluoro nucleotide
<220> FEATURE:
<221> NAME/KEY: misc_feature
<222> LOCATION: (26)..(26)
<223> OTHER INFORMATION: modified 2'-fluoro nucleotide
<220> FEATURE:
<221> NAME/KEY: misc_feature
<222> LOCATION: (28)..(29)
<223> OTHER INFORMATION: modified 2'-fluoro nucleotide
<220> FEATURE:
<221> NAME/KEY: misc_feature
<222> LOCATION: (32)..(35)
<223> OTHER INFORMATION: modified 2'-methoxy nucleotide
<220> FEATURE:
<221> NAME/KEY: misc_feature
<222> LOCATION: (37)..(37)
<223> OTHER INFORMATION: modified 2'-fluoro nucleotide
<220> FEATURE:
<221> NAME/KEY: misc_feature
<222> LOCATION: (38)..(38)
<223> OTHER INFORMATION: modified 2'-methoxy nucleotide
<220> FEATURE:
<221> NAME/KEY: misc_feature
<222> LOCATION: (39)..(39)
<223> OTHER INFORMATION: modified 2'-fluoro nucleotide
<220> FEATURE:
<221> NAME/KEY: misc_feature
<222> LOCATION: (40)..(43)
<223> OTHER INFORMATION: modified 2'-methoxy nucleotide

<400> SEQUENCE: 8
cggaccgaaa aagaccugac uucuauacua agucuacguu ccg                43

<210> SEQ ID NO 9
<211> LENGTH: 55
<212> TYPE: RNA
<213> ORGANISM: Artificial
<220> FEATURE:
<223> OTHER INFORMATION: Synthetic Aptamer

<400> SEQUENCE: 9
gugcagaucc ggguauaaug gguaguggag gguuucgggc uauaccagau cuugu      55

<210> SEQ ID NO 10
<211> LENGTH: 55
<212> TYPE: RNA
<213> ORGANISM: Artificial
<220> FEATURE:
<223> OTHER INFORMATION: Synthetic Aptamer

<400> SEQUENCE: 10
gugcagauug gaaaagggua guggauuugg gaaggguuua ggguuucaau cuugu      55

<210> SEQ ID NO 11
<211> LENGTH: 55
<212> TYPE: RNA
<213> ORGANISM: Artificial
```

```
<220> FEATURE:
<223> OTHER INFORMATION: Synthetic Aptamer

<400> SEQUENCE: 11
gugcagauaa acgggaaggg gucgggaaaa agggcaauau caagcgcaau cuugu        55

<210> SEQ ID NO 12
<211> LENGTH: 59
<212> TYPE: RNA
<213> ORGANISM: Artificial
<220> FEATURE:
<223> OTHER INFORMATION: Synthetic Aptamer

<400> SEQUENCE: 12
ggggcagaua aacgggaagg ggucgggaaa aagggcaaua ucaagcgcaa ucuuguccc    59

<210> SEQ ID NO 13
<211> LENGTH: 45
<212> TYPE: RNA
<213> ORGANISM: Artificial
<220> FEATURE:
<223> OTHER INFORMATION: Synthetic Aptamer

<400> SEQUENCE: 13
gugcagaucg ggaaggucgg gaaaagggcu aucgcgcaau cuugu                  45

<210> SEQ ID NO 14
<211> LENGTH: 55
<212> TYPE: RNA
<213> ORGANISM: Artificial
<220> FEATURE:
<223> OTHER INFORMATION: Synthetic Aptamer

<400> SEQUENCE: 14
gugcagauaa gcgggaaggg uucgggaaau ugggccuuau cccgcucuau cucgc        55

<210> SEQ ID NO 15
<211> LENGTH: 59
<212> TYPE: RNA
<213> ORGANISM: Artificial
<220> FEATURE:
<223> OTHER INFORMATION: Synthetic Aptamer

<400> SEQUENCE: 15
ggggcagauc cggguauaau ggguagugga ggguuucggg cuauaccaga ucuuguccc    59

<210> SEQ ID NO 16
<211> LENGTH: 45
<212> TYPE: RNA
<213> ORGANISM: Artificial
<220> FEATURE:
<223> OTHER INFORMATION: Synthetic Aptamer

<400> SEQUENCE: 16
gugcagccgg gauaauguag uggagggmuu cggcauccag cuugu                  45

<210> SEQ ID NO 17
<211> LENGTH: 55
<212> TYPE: RNA
<213> ORGANISM: Artificial
<220> FEATURE:
<223> OTHER INFORMATION: Synthetic Aptamer

<400> SEQUENCE: 17
gugcugaucc ggguaucaug gguggucgag gguuuggcgc gauacccgau cgugc        55
```

```
<210> SEQ ID NO 18
<211> LENGTH: 45
<212> TYPE: RNA
<213> ORGANISM: Artificial
<220> FEATURE:
<223> OTHER INFORMATION: Synthetic Aptamer

<400> SEQUENCE: 18
gugcagccgg gauaauggaa acgugggaau gaucauccag cuugc          45

<210> SEQ ID NO 19
<211> LENGTH: 45
<212> TYPE: RNA
<213> ORGANISM: Artificial
<220> FEATURE:
<223> OTHER INFORMATION: Synthetic Aptamer

<400> SEQUENCE: 19
gugcugccgg gaucaugugg ucgagggUuu cgggaucccg cgugc          45

<210> SEQ ID NO 20
<211> LENGTH: 36
<212> TYPE: RNA
<213> ORGANISM: Artificial
<220> FEATURE:
<223> OTHER INFORMATION: Synthetic Aptamer

<400> SEQUENCE: 20
gccgggauaa uggaaacgug ggaaugauca uccagc                    36

<210> SEQ ID NO 21
<211> LENGTH: 36
<212> TYPE: RNA
<213> ORGANISM: Artificial
<220> FEATURE:
<223> OTHER INFORMATION: Synthetic Aptamer

<400> SEQUENCE: 21
gccgggauca ugguucgag gguucggga ucccgc                      36

<210> SEQ ID NO 22
<211> LENGTH: 59
<212> TYPE: RNA
<213> ORGANISM: Artificial
<220> FEATURE:
<223> OTHER INFORMATION: Synthetic Aptamer

<400> SEQUENCE: 22
ggggcagauu ggaaaagggu aguggauuug ggaagggUuu agggUuucaa ucuugUccc    59

<210> SEQ ID NO 23
<211> LENGTH: 45
<212> TYPE: RNA
<213> ORGANISM: Artificial
<220> FEATURE:
<223> OTHER INFORMATION: Synthetic Aptamer

<400> SEQUENCE: 23
gugcagauga aagggUagu auugggaagg uagggUucau cuugu           45

<210> SEQ ID NO 24
<211> LENGTH: 55
<212> TYPE: RNA
<213> ORGANISM: Artificial
<220> FEATURE:
<223> OTHER INFORMATION: Synthetic Aptamer
```

```
<400> SEQUENCE: 24
gugcggauug gaacaggguc uaggauuugg gaagguuuua ggguuucaau ccugc       55

<210> SEQ ID NO 25
<211> LENGTH: 45
<212> TYPE: RNA
<213> ORGANISM: Artificial
<220> FEATURE:
<223> OTHER INFORMATION: Synthetic Aptamer

<400> SEQUENCE: 25
gugcagauga aagggguagu guugggaagg caggguucau cuugc                 45

<210> SEQ ID NO 26
<211> LENGTH: 45
<212> TYPE: RNA
<213> ORGANISM: Artificial
<220> FEATURE:
<223> OTHER INFORMATION: Synthetic Aptamer

<400> SEQUENCE: 26
gugcggauga acagggucua auugggaagg uaggguucau cuugc                 45

<210> SEQ ID NO 27
<211> LENGTH: 36
<212> TYPE: RNA
<213> ORGANISM: Artificial
<220> FEATURE:
<223> OTHER INFORMATION: Synthetic Aptamer

<400> SEQUENCE: 27
gaugaaaagg guaguguugg gaaggcaggg uucauc                           36

<210> SEQ ID NO 28
<211> LENGTH: 36
<212> TYPE: RNA
<213> ORGANISM: Artificial
<220> FEATURE:
<223> OTHER INFORMATION: Synthetic Aptamer

<400> SEQUENCE: 28
gaugaacagg gucuaauugg gaagguaggg uucauc                           36

<210> SEQ ID NO 29
<211> LENGTH: 56
<212> TYPE: RNA
<213> ORGANISM: Artificial
<220> FEATURE:
<223> OTHER INFORMATION: Synthetic Aptamer

<400> SEQUENCE: 29
gugcagaguu acacgccaug ggauuuaggg gaaggaagug ggggucgugu ucuugu     56

<210> SEQ ID NO 30
<211> LENGTH: 60
<212> TYPE: RNA
<213> ORGANISM: Artificial
<220> FEATURE:
<223> OTHER INFORMATION: Synthetic Aptamer

<400> SEQUENCE: 30
ggggcagagu uacacgccau gggauuuagg ggaaggaagu ggggucgug uucuugucc  60

<210> SEQ ID NO 31
```

```
<211> LENGTH: 56
<212> TYPE: RNA
<213> ORGANISM: Artificial
<220> FEATURE:
<223> OTHER INFORMATION: Synthetic Aptamer

<400> SEQUENCE: 31
gugcucuguu acacgccacg ggauugaagg caagaaagug gaggacgugu ucaagc        56

<210> SEQ ID NO 32
<211> LENGTH: 48
<212> TYPE: RNA
<213> ORGANISM: Artificial
<220> FEATURE:
<223> OTHER INFORMATION: Synthetic Aptamer

<400> SEQUENCE: 32
gugcagaguu acgcauggga uuaggggaag gaaugggguc guucuugu                 48

<210> SEQ ID NO 33
<211> LENGTH: 85
<212> TYPE: RNA
<213> ORGANISM: Artificial
<220> FEATURE:
<223> OTHER INFORMATION: Synthetic Aptamer

<400> SEQUENCE: 33
ggaagaggaa agaagugcag auaaacggga aggggucggg aaaaagggca auaucaagcg    60
caaucuugug cucgcgaggc aauca                                          85

<210> SEQ ID NO 34
<211> LENGTH: 85
<212> TYPE: RNA
<213> ORGANISM: Artificial
<220> FEATURE:
<223> OTHER INFORMATION: Synthetic Aptamer

<400> SEQUENCE: 34
ggaagaggaa agaagugcag auccggguau aauggguagu ggaggguuuc gggcuauacc    60
agaucuugug cucgcgaggc aauca                                          85

<210> SEQ ID NO 35
<211> LENGTH: 85
<212> TYPE: RNA
<213> ORGANISM: Artificial
<220> FEATURE:
<223> OTHER INFORMATION: Synthetic Aptamer

<400> SEQUENCE: 35
ggaagaggaa agaagugcag auuggaaaag gguaguggau uugggaaggg uuuaggguuu    60
caaucuugug cucgcgaggc aauca                                          85

<210> SEQ ID NO 36
<211> LENGTH: 86
<212> TYPE: RNA
<213> ORGANISM: Artificial
<220> FEATURE:
<223> OTHER INFORMATION: Synthetic Aptamer

<400> SEQUENCE: 36
ggaagaggaa agaagugcag aguuacacgc caugggauuu aggggaagga agugggguc    60 guguucuugu gcucgcgagg caauca                                         86
```

```
<210> SEQ ID NO 37
<211> LENGTH: 61
<212> TYPE: RNA
<213> ORGANISM: Artificial
<220> FEATURE:
<223> OTHER INFORMATION: Synthetic Aptamer

<400> SEQUENCE: 37
ugagugccau ugguuacagg auguuucugg uugaaucugg aaugcauugc aucacgucgc    60
u                                                                    61
```